United States Patent
Dunn et al.

(10) Patent No.: US 11,331,051 B2
(45) Date of Patent: May 17, 2022

(54) ANALYSIS OF GLUCOSE MEDIAN, VARIABILITY, AND HYPOGLYCEMIA RISK FOR THERAPY GUIDANCE

(71) Applicant: ABBOTT DIABETES CARE INC., Alameda, CA (US)

(72) Inventors: Timothy C. Dunn, San Francisco, CA (US); Kenneth J. Doniger, Menlo Park, CA (US); Glenn Berman, Alameda, CA (US); Gary A. Hayter, Oakland, CA (US); Erwin S. Budiman, Fremont, CA (US); Daniel M. Bernstein, El Granada, CA (US); Nathan Crouther, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 17/122,990

(22) Filed: Dec. 15, 2020

(65) Prior Publication Data
US 2021/0100515 A1 Apr. 8, 2021

Related U.S. Application Data

(63) Continuation of application No. 16/459,203, filed on Jul. 1, 2019, which is a continuation of application
(Continued)

(51) Int. Cl.
*A61B 5/145* (2006.01)
*A61B 5/00* (2006.01)
(Continued)

(52) U.S. Cl.
CPC ........ *A61B 5/7275* (2013.01); *A61B 5/14532* (2013.01); *G16H 50/20* (2018.01); *A61B 5/743* (2013.01); *G16H 50/30* (2018.01)

(58) Field of Classification Search
None
See application file for complete search history.

(56) References Cited

U.S. PATENT DOCUMENTS

| | | |
|---|---|---|
| 4,695,954 A | 9/1987 | Rose et al. |
| 4,731,726 A | 3/1988 | Allen, III |

(Continued)

FOREIGN PATENT DOCUMENTS

| | | |
|---|---|---|
| GB | 2443434 | 5/2008 |
| JP | 2001-245900 | 9/2001 |

(Continued)

OTHER PUBLICATIONS

Feig et al, "Continuous glucose monitoring in pregnant women with type 1 diabetes (CONCEPTT): a multicenter international randomised controlled trial," Sep. 15, 2017, www.thelancet.com, vol. 390, pp. 2347-2359 (Year: 2017).*

(Continued)

*Primary Examiner* — Alex M Valvis
*Assistant Examiner* — Aurelie H Tu
(74) *Attorney, Agent, or Firm* — Sterne, Kessler, Goldstein & Fox P.L.L.C.

(57) ABSTRACT

A system and method to provide guidance for diabetes therapy includes determining glycemic risks based on an analysis of glucose data. The analysis includes visualization of a glucose median, the variability of glucose in a patient, and the risk of hypoglycemia. An Advanced Daily Patterns report includes a visualization of an ambulatory glucose profile and a glucose control measure. The glucose control measure provides a highly visible and understandable display of the glucose condition of a patient visually expressed in the categories of low glucose, median glucose, and glucose variability.

18 Claims, 49 Drawing Sheets

Related U.S. Application Data

No. 14/145,554, filed on Dec. 31, 2013, now Pat. No. 10,383,580, which is a continuation-in-part of application No. 13/732,184, filed on Dec. 31, 2012, now Pat. No. 9,351,670.

(51) Int. Cl.
  *G16H 50/20*   (2018.01)
  *G16H 50/30*   (2018.01)

(56) References Cited

U.S. PATENT DOCUMENTS

| | | |
|---|---|---|
| 4,779,199 A | 10/1988 | Yoneda et al. |
| 4,817,044 A | 3/1989 | Ogren |
| 5,019,974 A | 5/1991 | Beckers |
| 5,216,597 A | 6/1993 | Beckers et al. |
| 5,251,126 A | 10/1993 | Kahn et al. |
| 5,307,263 A | 4/1994 | Brown |
| 5,319,363 A | 6/1994 | Welch et al. |
| 5,341,291 A | 8/1994 | Roizen et al. |
| 5,376,070 A | 12/1994 | Purvis et al. |
| 5,500,854 A | 3/1996 | Uotila |
| 5,558,638 A | 9/1996 | Evers et al. |
| 5,590,648 A | 1/1997 | Mitchell et al. |
| 5,626,144 A | 5/1997 | Tacklind et al. |
| 5,704,366 A | 1/1998 | Tacklind et al. |
| 5,713,856 A | 2/1998 | Eggers et al. |
| 5,772,586 A | 6/1998 | Heinonen et al. |
| 5,822,715 A | 10/1998 | Worthington et al. |
| 5,878,384 A | 3/1999 | Johnson et al. |
| 5,925,021 A | 7/1999 | Castellano et al. |
| 5,946,659 A | 8/1999 | Lancelot et al. |
| 5,960,403 A | 9/1999 | Brown |
| 5,974,389 A | 10/1999 | Clark et al. |
| 5,997,476 A | 12/1999 | Brown |
| 6,022,315 A | 2/2000 | Iliff |
| 6,024,699 A | 2/2000 | Surwit et al. |
| 6,049,764 A | 4/2000 | Stahl |
| 6,081,786 A | 6/2000 | Barry et al. |
| 6,134,504 A | 10/2000 | Douglas et al. |
| 6,144,922 A | 11/2000 | Douglas et al. |
| 6,188,988 B1 | 2/2001 | Barry et al. |
| 6,206,829 B1* | 3/2001 | Iliff ................... A61B 5/411 600/300 |
| 6,225,901 B1 | 5/2001 | Kail, IV |
| 6,234,964 B1 | 5/2001 | Iliff |
| 6,270,455 B1 | 8/2001 | Brown |
| 6,277,071 B1 | 8/2001 | Hennessy et al. |
| 6,336,900 B1 | 1/2002 | Alleckson et al. |
| 6,338,713 B1 | 1/2002 | Chamoun et al. |
| 6,352,505 B1 | 3/2002 | Bortz |
| 6,368,273 B1 | 4/2002 | Brown |
| 6,379,301 B1 | 4/2002 | Worthington et al. |
| 6,390,986 B1 | 5/2002 | Curcie et al. |
| 6,406,426 B1 | 6/2002 | Reuss et al. |
| 6,418,346 B1 | 7/2002 | Nelson et al. |
| 6,422,061 B1 | 7/2002 | Sunshine et al. |
| 6,450,956 B1 | 9/2002 | Rappaport et al. |
| 6,524,240 B1 | 2/2003 | Thede |
| 6,540,672 B1 | 4/2003 | Simonsen et al. |
| 6,544,174 B2 | 4/2003 | West et al. |
| 6,544,212 B2 | 4/2003 | Galley et al. |
| 6,551,243 B2 | 4/2003 | Bocionek et al. |
| 6,558,351 B1 | 5/2003 | Steil et al. |
| 6,575,900 B1 | 6/2003 | Zweig et al. |
| 6,579,231 B1 | 6/2003 | Phipps |
| 6,604,050 B2 | 8/2003 | Trippel et al. |
| 6,611,846 B1 | 8/2003 | Stoodley |
| 6,635,016 B2 | 10/2003 | Finkelshteins |
| 6,635,167 B1 | 10/2003 | Batman et al. |
| 6,645,142 B2 | 11/2003 | Braig et al. |
| 6,656,114 B1 | 12/2003 | Poulsen et al. |
| 6,692,436 B1 | 2/2004 | Bluth et al. |
| 6,781,522 B2 | 8/2004 | Sleva et al. |
| 6,799,149 B2 | 9/2004 | Hartlaub |
| 6,804,558 B2 | 10/2004 | Haller et al. |
| 6,872,200 B2 | 3/2005 | Mann et al. |
| 6,882,940 B2 | 4/2005 | Potts et al. |
| 6,915,170 B2 | 7/2005 | Engleson et al. |
| 7,241,265 B2 | 7/2007 | Cummings et al. |
| 7,920,907 B2 | 4/2011 | McGarraugh et al. |
| 8,409,093 B2 | 4/2013 | Bugler |
| 8,758,245 B2 | 6/2014 | Ray et al. |
| 2001/0039503 A1 | 11/2001 | Chan et al. |
| 2003/0216628 A1 | 11/2003 | Bortz et al. |
| 2004/0091424 A1 | 5/2004 | Asano et al. |
| 2005/0027182 A1 | 2/2005 | Siddiqui et al. |
| 2005/0119540 A1 | 6/2005 | Potts et al. |
| 2005/0159656 A1 | 7/2005 | Hockersmith et al. |
| 2005/0187789 A1 | 8/2005 | Hatlestad et al. |
| 2005/0214892 A1 | 9/2005 | Kovatchev et al. |
| 2005/0267780 A1 | 12/2005 | Ray et al. |
| 2006/0010098 A1 | 1/2006 | Goodnow et al. |
| 2006/0106644 A1 | 5/2006 | Koo et al. |
| 2006/0173260 A1 | 8/2006 | Gaoni et al. |
| 2006/0189863 A1 | 8/2006 | Peyser et al. |
| 2006/0264895 A1 | 11/2006 | Flanders |
| 2007/0016449 A1 | 1/2007 | Cohen et al. |
| 2007/0033074 A1 | 2/2007 | Nitzan et al. |
| 2007/0179352 A1 | 8/2007 | Randlov et al. |
| 2008/0071580 A1 | 3/2008 | Marcus et al. |
| 2008/0125636 A1* | 5/2008 | Ward ................... A61B 5/4833 600/365 |
| 2008/0154513 A1 | 6/2008 | Kovatchev et al. |
| 2008/0234943 A1 | 9/2008 | Ray et al. |
| 2008/0234992 A1 | 9/2008 | Ray et al. |
| 2008/0235053 A1 | 9/2008 | Ray et al. |
| 2008/0255438 A1* | 10/2008 | Saidara ................... G16H 40/63 600/365 |
| 2009/0105573 A1 | 4/2009 | Malecha |
| 2009/0171589 A1 | 7/2009 | Kovatchev |
| 2009/0240127 A1 | 9/2009 | Ray |
| 2010/0152554 A1 | 6/2010 | Steine et al. |
| 2010/0261987 A1* | 10/2010 | Kamath ............... A61B 5/4833 600/365 |
| 2010/0268043 A1* | 10/2010 | Yodfat ............... A61B 5/14546 600/345 |
| 2010/0298765 A1* | 11/2010 | Budiman ............. A61B 5/4839 604/66 |
| 2010/0332445 A1 | 12/2010 | Ray et al. |
| 2011/0130746 A1 | 6/2011 | Budiman |
| 2011/0201911 A1* | 8/2011 | Johnson ................... G06F 3/041 600/365 |
| 2011/0264378 A1 | 10/2011 | Breton et al. |
| 2013/0035575 A1 | 2/2013 | Mayou et al. |
| 2013/0303446 A1* | 11/2013 | Hamilton .................. A61P 9/10 514/6.5 |
| 2014/0030748 A1 | 1/2014 | Schaible |
| 2014/0088392 A1 | 3/2014 | Bernstein et al. |
| 2014/0088393 A1 | 3/2014 | Bernstein et al. |
| 2014/0188400 A1 | 7/2014 | Dunn et al. |
| 2014/0350369 A1* | 11/2014 | Budiman ............... G16H 20/10 600/365 |

FOREIGN PATENT DOCUMENTS

| | | |
|---|---|---|
| JP | 2003-500744 | 1/2003 |
| JP | 2004-024699 | 1/2004 |
| WO | WO 00/04512 A2 | 1/2000 |
| WO | WO 02/05702 A2 | 1/2002 |
| WO | WO 2005/081170 A2 | 9/2005 |
| WO | WO 2010/075350 A1 | 7/2010 |
| WO | WO 2012/108939 A1 | 8/2012 |

OTHER PUBLICATIONS

Siegmund et al, "Longitudinal changes in the continuous glucose profile measured by the CGMS in healthy pregnant women and determination of cut-off values," Jul. 2008, European Journal of Obstetrics & Gynecology and Reproductive Biology, vol. 139, pp. 46-42 (Year: 2008).*

(56) References Cited

OTHER PUBLICATIONS

Pugh et al., Does hypoglycemia following a glucose challenge test identify a high risk pregnancy?, Jul. 14, 2009, BioMed Central, Reproductive Health, 6:10, pp. 1-7 (Year: 2009).*
Feinberg, et al. Does Maternal Hypoglycemia during Screening Glucose Assessment Identify a Pregnancy At-Risk for Adverse Preinatal Outcome?, 2005, Nature Publishing Group, Journal of Perinatology, vol. 25, pp. 509-513 (Year: 2005).*
Abell, The Significance of Abnormal Gluc9ose Tolerance (Hyperglycaemia and Hypoglycaemia) in Pregnancy, Mar. 1979, British Journal of Obstetrics and Gynaecology, vol. 86, pp. 214-221 (Year: 1979).*
AU 2013369674 Second Examination Report dated Jul. 1, 2019.
EP 18159413.6 Search Report dated Jun. 7, 2018.
WO PCT/US2013/078535 ISR and Written Opinion dated Sep. 4, 2014.
WO PCT/US2014/030075 ISR and Written Opinion dated Aug. 6, 2014.
Breton, M., et al., "A Model of Self-Treatment Behavior, Glucose Variability, and Hypoglycemia-Associated Autonomic Failure in Type 1 Diabetes", Journal of Diabetes Science and Technology, 2007, vol. 1, No. 3, pp. 331-337.
Brownlee, M., et al., "Glycemic Variability: A Hemoglobin A1c-Independent Risk Factor for Diabetic Complications", JAMA, 2006, vol. 295, No. 14, pp. 1707-1708.
Czerwoniuk, D., et al., "GlyCulator: A Glycemic Variability Calculation Tool for Continuous Glucose Monitoring Data", Journal of Diabetes Science and Technology, 2011, vol. 5, No. 2, pp. 447-451.
Dunn, Timothy C., et al., "Rates of Glucose Change Measured by Blood Glucose Meter and the GlucoWatch Biographer During Day, Night, and Around Mealtimes", Diabetes Care, 2004, vol. 27, No. 9, pp. 2161-2165.
Freeman, J., et al., "The Use of Continuous Glucose Monitoring to Evaluate the Glycemic Response to Food", Diabetes Spectrum, 2008, vol. 21, No. 2, pp. 134-137.
Fritzsche, G., et al., "The Use of a Computer Program to Calculate the Mean Amplitude of Glycemic Excursions", Diabetes Technology & Therapeutics, 2011, vol. 13, No. 3, pp. 319-325.

Harvey, R.A., et al., "Clinically Relevant Hypoglycemia Prediction Metrics for Event Mitigation", Diabetes Technology & Therapeutics, 2012, vol. 14, No. 8, pp. 719-727.
Hughes, C.A., et al., "Hypoglycemia Prevention via Pump Attenuation and Red-Yellow-Green "Traffic" Lights Using Continuous Glucose Monitoring and Insulin Pump Data", Journal of Diabetes Science and Technology, 2010, vol. 4, No. 5, pp. 1146-1155.
Kilpatrick, E. S., "The Effect of Glucose Variability on the Risk of Microvascular Complications in Type 1 Diabetes", Diabetes Care, 2006, vol. 29, No. 7, pp. 1486-1490.
Kovatchev, B. P., et al., "Assessment of Risk for Severe Hypoglycemia Among Adults With DDM: Validation of the Low Blood Glucose Index", Diabetes Care, vol. 21, No. 11, 1998, pp. 1870-1875.
Kovatchev, B. P., et al., "Quantifying Temporal Glucose Variability in Diabetes via Continuous Glucose Monitoring: Mathematical Methods and Clinical Application", Diabetes Technology & Therapeutics, vol. 7, No. 6, 2005, pp. 849-862.
Mazze, R. S., "Ambulatory Glucose Profile: Representation of Verified Self-Monitored Blood Glucose Data", Diabetes Care, 1987, vol. 10, No. 1, pp. 111-117.
Mazze, R. S., "Characterizing Glucose Exposure for Individuals with Normal Glucose Tolerance Using Continuous Glucose Monitoring and Ambulatory Glucose Profile Analysis", Diabetes Technology & Therapeutics, 2008, vol. 10, No. 3, pp. 149-159.
Rodbard, D., "Optimizing Display, Analysis, Interpretation and Utility of Self-Monitoring of Blood Glucose (SMBG) Data for Management of Patients with Diabetes", Journal of Diabetes Science and Technology, 2007, vol. 1, No. 1, pp. 62-71.
Wilson, D. M., "The Accuracy of the Freestyle Navigator Continuous Glucose Monitoring System in Children With Type 1 Diabetes", Diabetes Care, 2007, vol. 30, No. 1, pp. 59-64.
Bergenstal, R., et al., "Recommendations for Standardizing Glucose Reporting and Analysis to Optimize Clinical Decision Making in Diabetes: The Ambulatory Glucose Profile (AGP)", Diabetes Technology & Therapeutics, 2011, vol. 15, No. 3, pp. 198-211.

* cited by examiner

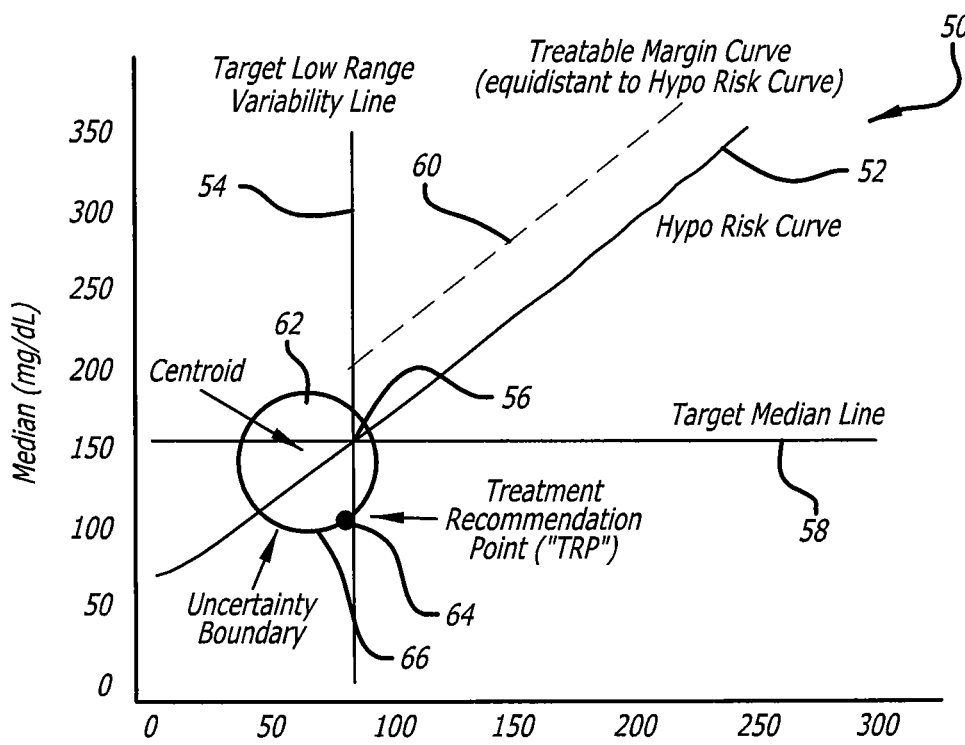
FIG. 1  Control Grid definition and data elements
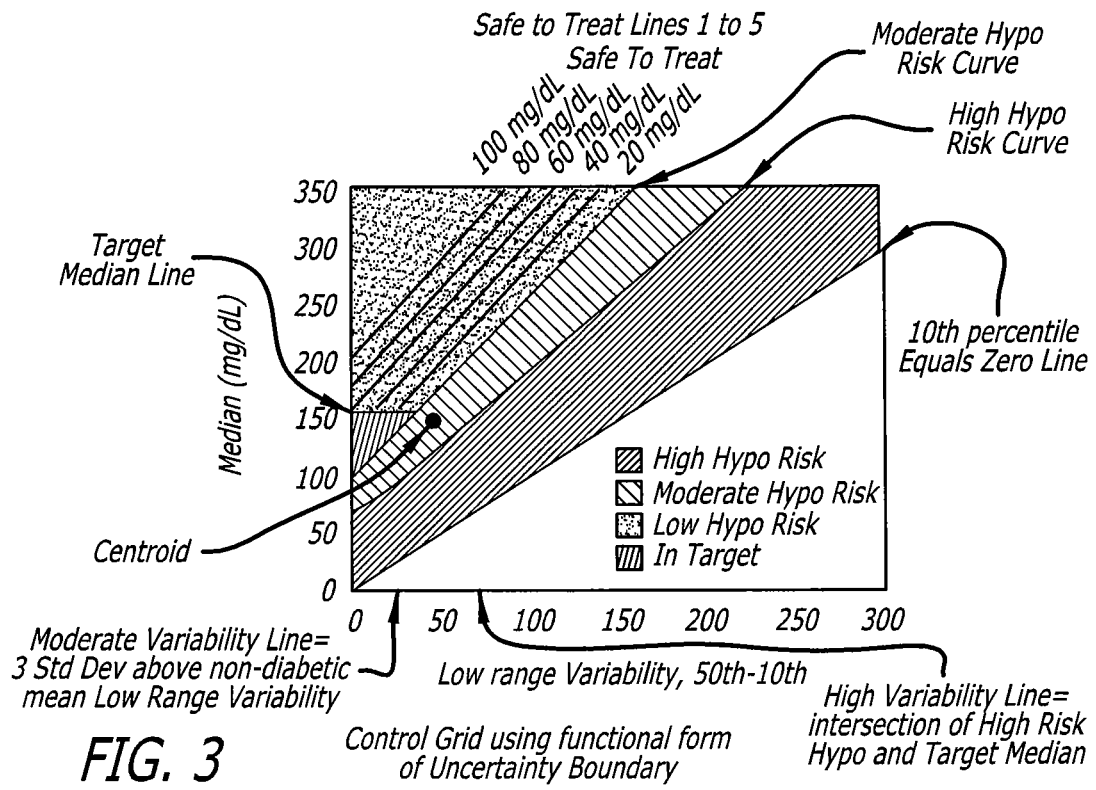
FIG. 3  Control Grid using functional form of Uncertainty Boundary Graphical definitions of Risk Reduction Distances Examples for HypoRRD Examples for HyperRRD

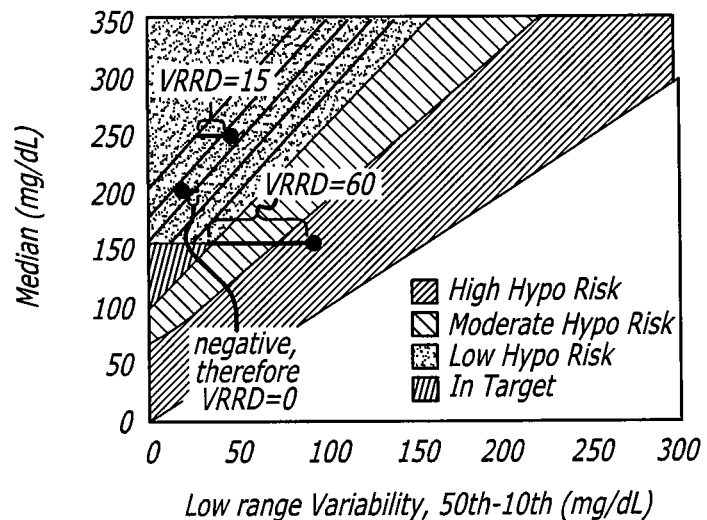
FIG. 6  Examples for VRRD
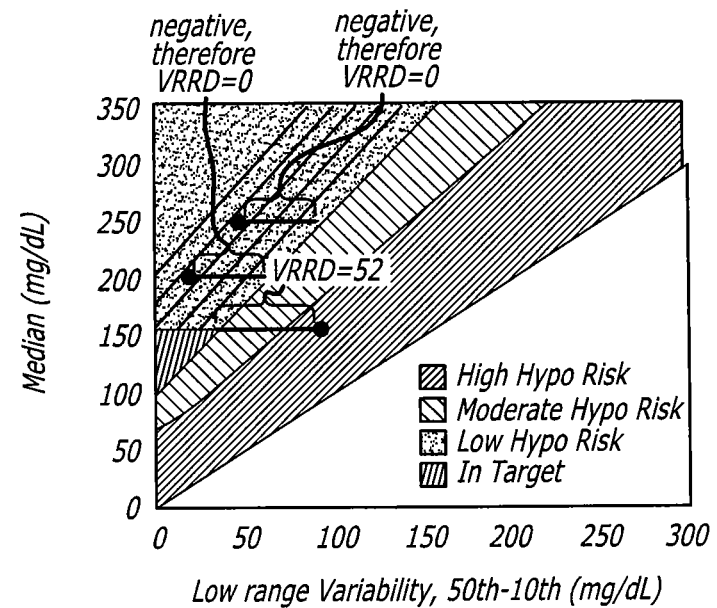
FIG. 7  Examples for VRRD, alternate definition

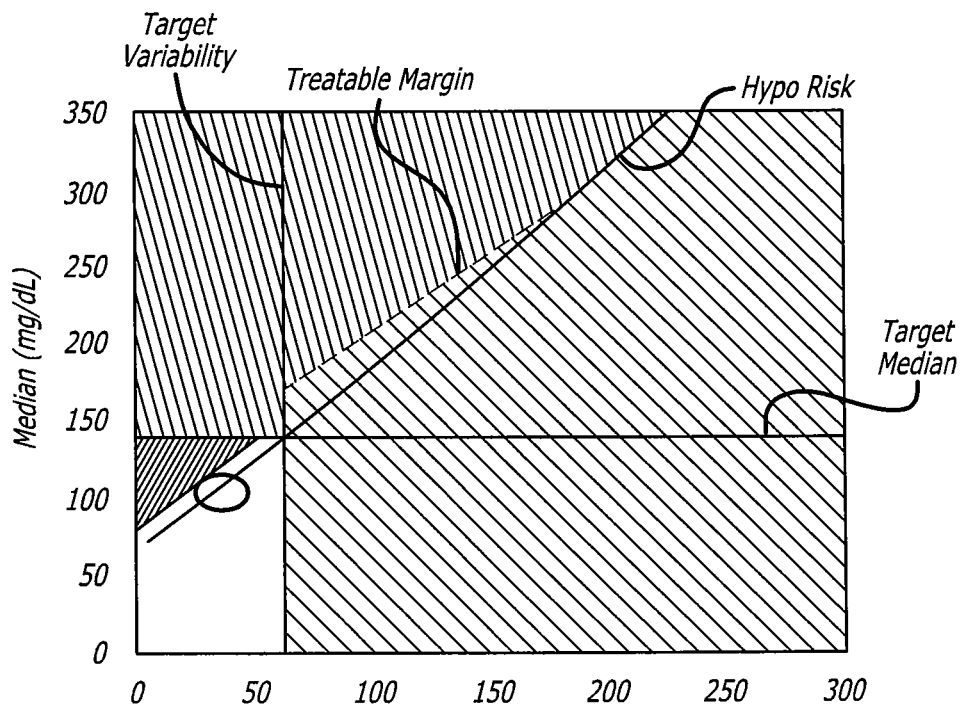
FIG. 10 Low range Variability, 50th-10th (mg/dL)
Alternate design of zone definition
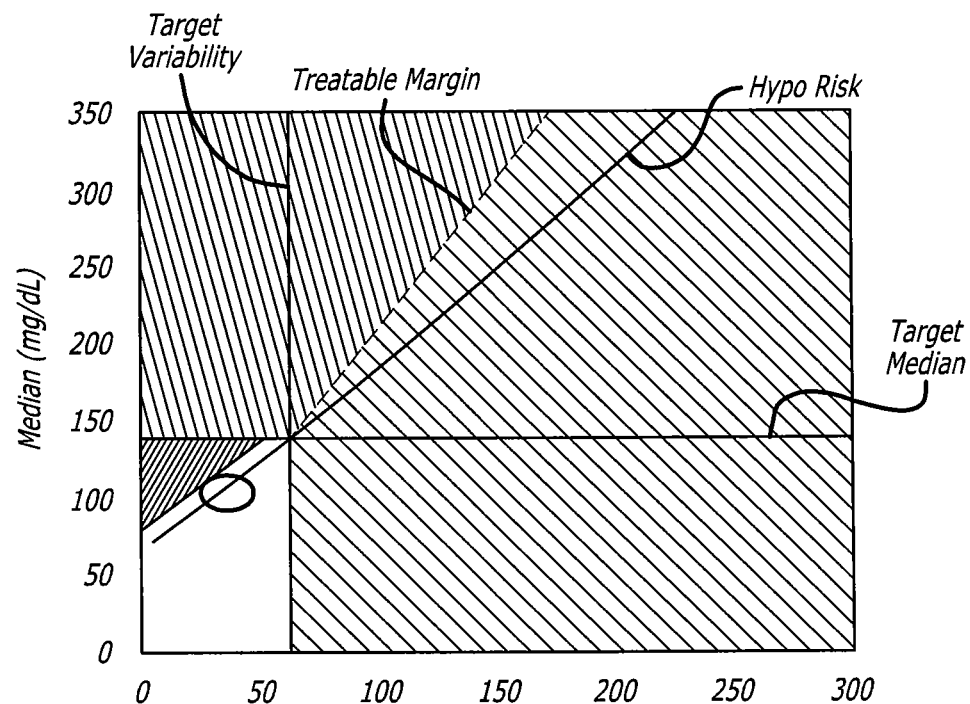
FIG. 11 Low range Variability, 50th-10th (mg/dL)
Alternate design of zone definition

| Glucose Control Assessment | | | Description | Possible Action |
|---|---|---|---|---|
| Likelihood of LOW GLUCOSE | OK | | At Target/ No Changes needed | 1. If not at A1C target, consider lowering Glucose Goal |
| MEDIAN GLUCOSE (compared to goal) | OK | | | |
| VARIABILITY BELOW MEDIAN (median to 10th percentile) | OK | | | |
| Likelihood of LOW GLUCOSE | OK | | Address Self-Care | 1. Address self-care behaviors to lower glucose variability to reduce potential for hypoglycemia risk 2. If not at A1C target, consider lowering Glucose Goal |
| MEDIAN GLUCOSE (compared to goal) | OK | | | |
| VARIABILITY BELOW MEDIAN (median to 10th percentile) | ◐ | | | |
| Likelihood of LOW GLUCOSE | ◐ | | Decrease Dose | 1. Decrease insulin coverage to reduce hypoglycemia risk |
| MEDIAN GLUCOSE (compared to goal) | OK | | | |
| VARIABILITY BELOW MEDIAN (median to 10th percentile) | OK | | | |
| Likelihood of LOW GLUCOSE | ◐ | ◐ | Address Self-Care, Decrease Dose if Necessary | 1. Address self-care behaviors to lower glucose variability to reduce hypoglycemia risk 2. If patient's ability to reduce variability is judged to be unlikely or insufficient, decrease insulin coverage to reduce hypoglycemia risk |
| MEDIAN GLUCOSE (compared to goal) | OK | OK | | |
| VARIABILITY BELOW MEDIAN (median to 10th percentile) | ◐ | ◐ | | |
| Likelihood of LOW GLUCOSE | ◐ | ◐ | | |
| MEDIAN GLUCOSE (compared to goal) | ◐ | ◐ | | |
| VARIABILITY BELOW MEDIAN (median to 10th percentile) | ◐ | ◐ | | |
| Likelihood of LOW GLUCOSE | OK | | Increase Dose | 1. Increase insulin coverage to reduce hyperglycemia 2 |
| MEDIAN GLUCOSE (compared to goal) | ◐ | | | |
| VARIABILITY BELOW MEDIAN (median to 10th percentile) | OK | | | |
| Likelihood of LOW GLUCOSE | OK | OK | Increase Dose while Addressing Self-Care | 1. Increase insulin coverage to reduce hyperglycemia 2

2. Address self-care behaviors to lower glucose variability to reduce potential for hypoglycemia risk |
| MEDIAN GLUCOSE (compared to goal) | ◐ | ◐ | | |
| VARIABILITY BELOW MEDIAN (median to 10th percentile) | ◐ | ◐ | | |

FIG. 28B

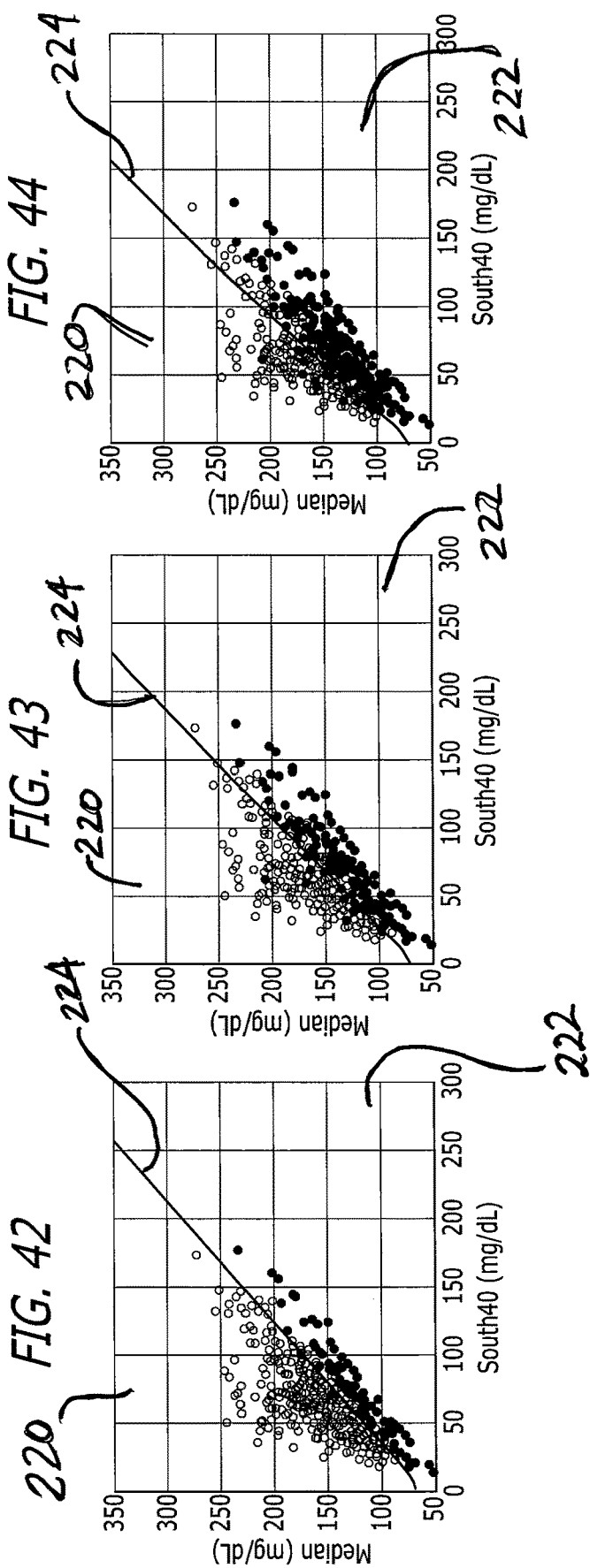

ANALYSIS OF GLUCOSE MEDIAN, VARIABILITY, AND HYPOGLYCEMIA RISK FOR THERAPY GUIDANCE

RELATED APPLICATIONS

The present application is a continuation of U.S. patent application Ser. No. 16/459,203, filed Jul. 1, 2019, which is a continuation of U.S. patent application Ser. No. 14/145,554, filed Dec. 31, 2013, now U.S. Pat. No. 10,383,580, which is a continuation-in-part of U.S. patent application Ser. No. 13/732,184, filed Dec. 31, 2012, now U.S. Pat. No. 9,351,670, all of which are incorporated herein by reference in their entireties for all purposes.

BACKGROUND

The invention relates generally to medical data processing and display, and more particularly, to a system and method for collecting, analyzing, and displaying analyses of medical analyte data for managing diabetes mellitus.

Diabetes mellitus, or simply, "diabetes," is an incurable chronic disease. Type 1 diabetics must manage their diabetes by taking a glucose-lowering medication, such as insulin, to compensate for the rise in blood glucose that follows food consumption. Type 1 diabetes management works to prevent hyperglycemia, or high blood glucose, while especially averting the consequences of hypoglycemia, or low blood glucose, from over-aggressive or incorrect insulin dosing. Poor diabetes management can manifest in acute symptoms, such as loss of consciousness, or through chronic conditions, including cardiovascular disease, retinopathy, neuropathy, and nephropathy. Effective diabetes management requires effort.

Many different ways exist to assist in monitoring and managing one's glucose levels. Health care maintenance systems based on the use of a handheld device are often used. These devices are configured to record patient data, such as blood glucose data. Additionally, it is known that such data can be uploaded to a remote server for storage of large quantities of medical data and later access to it by third parties, such as the patient's health care providers ("HCP"). Examples are Google Health and Microsoft HealthVault™. At the remote server location or elsewhere, blood glucose test results can be matched with quantitative information on medication, meals, or other factors, such as exercise.

Medical sensors can generate large quantities of useful information about a physiological parameter or parameters of a patient. That information, when processed, organized, and analyzed in particular ways, can be highly beneficial to an HCP in examining the patient and recommending treatment. The appropriate calculations, organization, and analyses of that data can assist in forming rapid, useful, and more accurate evaluations of the information, the patient's history, and the patient's present state and health condition.

For example, analyte monitoring and medication delivery devices are commonly used in the treatment of a patient. One or more samples of analytes from the patient's body tissues are sensed and data is accumulated. A monitor, containing a sensor and a processor, may be used to acquire, accumulate, and process that data. Ultimately a report must be produced from that data and an analysis made by an HCP. In response to the analysis, one or more medications may be administered to the patient or other course of treatment prescribed, such as exercise and control over the timing, amount, and contents of meals. Administration of the medication may be manual by the patient such as self-injection with a syringe, by another person such as a nurse, or by a powered medication administration device, such as an infusion pump, for automatic or continuous delivery. For example, glucose monitors and insulin pumps are commonly used in the treatment and management of type 1 diabetes mellitus.

In the case of diabetes, a blood glucose monitor ("BGM") or continuous glucose monitor ("CGM") may be used in obtaining data about the glucose level of a patient. Such sensors detect glucose levels through actual analysis of a drop of blood, or through sensing the composition of interstitial tissue. The patient may have a handheld digital device, such as a personal digital assistant ("PDA") that is used to receive and store his or her glucose data. This can occur in a number of ways. In the case where the patient draws a drop of blood onto a test strip that is read by a BGM, the data from the BGM may be communicated to the PDA for storage, processing (such as by adding a date and time stamp), and transfer elsewhere.

In one case, the BGM is integrated with the PDA (dedicated device) and in another case, both the BGM and the PDA may be integrated into a mobile telephone with the appropriate hardware and software as a single unit. In another case, the glucose data is communicated to the PDA wirelessly or through a wired connection. In both cases of the BGM and CGM, various schemes may be used to get measured patient glucose data onto the PDA. The PDA is programmed to process that data and can provide a useful number representation of a glucose level on the screen of the PDA, and can also be instructed to upload the data to a server that may be remote and which may be accessed through the Internet (cloud computing) or by other means. Conveniently, a computerized report can be used to display such measurements and calculations of the measured glucose together and can be analyzed for use in developing health management recommendations. For example, glucose monitors are programmed to provide recommendations for better blood glucose management in the patient. Such analyses often include trends, extrapolations, predictions, alerts, and others.

Accordingly, the detection of the level of analytes, such as glucose, lactate, oxygen, and the like, in certain individuals is vitally important to their health. Moreover, analyzing these analytes and recording analytics relating thereto, as well as other patient behavior, such as activities and meals, and providing this information to HCPs for analysis can provide valuable, life-saving feedback to patients who have difficult medical conditions. For example, monitoring glucose levels is particularly important to individuals with diabetes as well as monitoring diet and exercise, to determine when insulin is needed to reduce glucose levels in their bodies or when additional glucose is needed to raise the level of glucose in their bodies. The provision of related analytics of their glucose levels to an HCP may result in a therapy recommendation that may be useful in helping the patient better manage his or her diabetes. Existing data management and analysis tools are available and are further being developed to assist patients along these lines.

Previous glycemic control risks have been assessed visually by trained experts who have developed skills in balancing the competing demands of consistently lowering glucose levels while avoiding excessive hypoglycemia. Typically, these experts review plots or tables of glucose values. These skills are hard to acquire and transfer to others.

Self-monitoring blood glucose ("SMBG") testing schedules are assigned to patients by HCPs in order to gather data so that the HCPs can make recommendations to patients regarding therapy and lifestyle changes. Key metrics that can be ascertained by this SMBG testing are median glucose, low range variability, and hypoglycemia risk. Typically, a key therapy goal is to reduce a patient's median glucose while avoiding the risk of the patient spending significant time in hypoglycemia or experiencing a severe hypoglycemia incidence. The higher a patient's low range variability, the higher the median glucose the patient will need to maintain in order to avoid these incidences of hypoglycemia.

Some of the problems with SMBG testing schedules are patient compliance and limited data. Patients may not comply with an SMBG testing schedule because blood glucose ("BG") testing can be painful and inconvenient. In order to maximize compliance, SMBG test schedules generally occur over a short time period with just a handful of SMBG tests. This leads to the second problem, limited data. SMBG testing schedules will produce relatively small data sets which can introduce a high uncertainty to the calculated median glucose, calculated low range variability, and calculated hypoglycemia risk. The higher the uncertainty, the less aggressive the treatment recommendations can be in order to be sure that the hypoglycemia risks are avoided.

Additionally, another problem caused by collecting a small amount of data is that SMBG measurements can either be focused on a small number of short time periods or long time periods, but not both. For example, an SMBG test schedule might focus on median and variability at fixed times, for example one hour after meals, requiring the patient to perform tests every day for one to two weeks one hour after each scheduled meal. With such a test schedule, the median and low range variability can be calculated relatively accurately, but only for one hour after each scheduled meal. Little information will be learned about other time periods (such as two hours after each meal). Alternatively, the SMBG test schedule may follow a progressive schedule requiring the patient to test at various times of the day. For example, the schedule might ask for the patient to test at 7:00 AM, 11:00 AM, 3:00 PM, and 7:00 PM one day, and then 8:00 AM, 12:00 PM, 4:00 PM, and 8:00 PM the next day for one to two weeks. This type of SMBG test schedule can produce a relatively accurate portrayal of median and low range variability during the entire range of times tested. It is unlikely that a patient will comply with a testing schedule that requires a test during sleeping hours day after day.

Continuous glucose monitors ("CGMs") are also given to patients by HCPs to measure a patient's median glucose, low range variability, and hypoglycemia risk. By using a CGM, most of the problems associated with discrete blood glucose testing with BGMs can be addressed. With a CGM, one typically doesn't need to worry about patient compliance. There is enough data to measure low range variability to very small time periods, typically as short as one hour. Additionally, CGM systems provide data while the patient is sleeping.

The drawbacks of CGM are that it is relatively expensive, it can be uncomfortable, and patients must typically wear a device continuously, day and night, which many are very reluctant to do. It would therefore be helpful if a patient were able to wear a CGM for shorter periods of time, yet still obtain enough useful data to more accurately monitor and manage blood glucose.

Hence, those skilled in the art have recognized that there is a need for a system and a method that more accurately determine blood glucose levels in a patient. Another recognized need is for requiring the more useful and efficient collection of blood glucose data from patients so that patients will have a higher compliance level with a testing schedule. Another need is for an analysis system and method of the blood glucose data of a patient to consider variation in blood glucose levels so that glycemic risk can be determined, and better treatment can result. A further need is for a clearer analysis and display of glucose data so that treatment can be prescribed with a small risk that varying blood glucose levels may cause hypoglycemic incidence. The present invention fulfills these needs and others.

SUMMARY OF THE INVENTION

Briefly and in general terms, the present invention is directed to a system and method for determining glycemic risks and include visualization of hypoglycemia, variability, and hyperglycemia with a control grid and other displays, increasing the accuracy of glucose estimates using a combination of CGM and HbA1c, calculating glycemic risk by applying a probability distribution, and tailoring SMBG test schedules based on CGM use/wear.

In one aspect there is provided a system for determining glycemic risk based on analysis of glucose data, the system comprising a non-volatile memory in which is stored a glucose data processing program configured to program a processor to analyze received glucose data and from the analysis, produce a display, an input at which glucose data is received, a display on which glucose data and analytics thereof may be visually presented, a processor connected with the nonvolatile memory, the input, and the display, the processor being configured to access the memory to load and run in the processor the program to analyze glucose data, wherein the processor is programmed to analyze the received glucose data to determine a glucose median, a low range variability of glucose, and a hypoglycemia risk, and control the display to visually present glycemic risks of hypoglycemia and glucose variability for different times of the day, and thereby allow investigation and illustration of how changes in glucose levels could affect those risks, control the display to visually present a glucose control measure that includes an assessment of the glucose data in the categories of low glucose, median glucose, and glucose variability, whereby periods of the day needing a reduction in hypoglycemia and/or a reduction in glycemic variability can be seen.

In other more detailed aspects, the glucose processing program further programs the processor to control the display to visually present a control grid on which is shown a hypoglycemia risk curve and a glucose variability curve and also showing risk reduction distances for hypoglycemia and glucose variability. The glucose processing program further programs the processor to control the display to present visually on the control grid a treatment recommendation point. The glucose processing program further programs the processor to control the display to present visually on the control grid an uncertainty boundary. The glucose processing program further programs the processor to control the display to present visually on the control grid a hyperglycemia curve and a risk reduction distance for hyperglycemia.

In yet other detailed aspects, the glucose processing program further programs the processor to control the display to present visually a graphical representation of risk reduction showing hyperglycemia and glucose variability separately. The glucose processing program further programs the processor to control the display to visually present graphs representing risk reduction showing hyper and hypo combined with glucose variability. The glucose processing program further programs the processor to control the display to visually present the glucose control measure that includes an assessment of the glucose data visually expressed in terms of three categories of low, moderate, and high.

In further aspects, the system comprises a touch screen associated with the display, wherein the glucose processing program further programs the processor to receive input from the touch screen and control the display to visually present changes in hypoglycemia risk resulting from input from the touch screen showing alteration in glucose median and/or glucose variability. The glucose processing program further programs the processor to receive HbA1c data, analyze the HbA1c data with the glucose data, determine an estimate of average glucose; and control the display to present visually the estimate of average glucose. The glucose processing program further programs the processor to subject the glucose data to an analysis of probability distribution in determining glycemic risk.

Additional aspects include the glucose processing program further programming the processor to control the display to present visually hypoglycemic risk curve and blood glucose variability on a time period scale whereby the visual presentation on a time period scale indicates how an SMBG test schedule may be tailored to obtain further desired glucose data.

In method aspects of the invention, there is provided a method comprising the steps of storing in a non-volatile memory a glucose data processing program configured to program a processor to analyze received glucose data and from the analysis, produce a display, receiving glucose data, accessing the non-volatile memory and loading and running the glucose data processing program, analyzing the received glucose data to determine a glucose median, a low range variability of glucose, and a hypoglycemia risk, controlling a display to visually present glycemic risks of hypoglycemia and glucose variability for different times of the day, controlling the display to visually present a glucose control measure that includes an assessment of the glucose data in the categories of low glucose, median glucose, and glucose variability, thereby allowing investigation and illustration of how changes in glucose levels could affect those risks, whereby periods of the day needing a reduction in hypoglycemia and/or a reduction in glycemic variability can be seen.

In more detailed method aspects, the method comprises controlling the display to present visually a control grid on which is shown a hypoglycemia risk curve and a glucose variability curve and also showing risk reduction distances for hypoglycemia and glucose variability. Additionally, the method comprises controlling the display to visually present on the control grid a treatment recommendation point, and controlling the display to visually present on the control grid an uncertainty boundary. The method also includes controlling the display to visually present on the control grid a hyperglycemia curve and a risk reduction distance for hyperglycemia. Further, the method includes controlling the display to visually present a graphical representation of risk reduction showing hyperglycemia and glucose variability separately. In yet another aspect, the method includes controlling the display to visually present the glucose control measure that includes an assessment of the glucose data visually expressed in terms of three categories of low, moderate, and high.

In even further method aspects, the glucose processing program further programs the processor for controlling the display to visually present graphs representing risk reduction showing hyper and hypo combined with glucose variability. The glucose processing program further programs the processor for receiving input from a touch screen and controlling the display to visually present changes in hypoglycemia risk resulting from input from the touch screen showing alteration in glucose median and/or glucose variability. The glucose processing program further programs the processor for receiving HbA1c data, analyzing the HbA1c data with the glucose data, determining an estimate of average glucose, and controlling the display to visually present the estimate of average glucose.

In additional aspects, the glucose processing program further programs the processor for subjecting the glucose data to an analysis of probability distribution in determining glycemic risk. The glucose processing program further programs the processor for controlling the display to visually present a hypoglycemic risk curve and blood glucose variability on a time period scale, whereby the visual presentation on a time period scale indicates how an SMBG test schedule may be tailored to obtain further desired glucose data.

Various features and advantages of the invention will become more apparent by the following detailed description of several embodiments thereof with reference to the attached drawings.

BRIEF DESCRIPTION OF THE DRAWINGS

FIG. 1 shows a control grid definition with data elements;

FIG. 3 is the control grid using a functional form of uncertainty;

FIG. 6 shows examples of variability risk reduction distances.

FIG. 7 shows an alternate definition for variability risk reduction distances;

FIG. 10 shows another alternate design of zone definition as in FIG. 9;

FIG. 11 is yet another alternate design of zone definition;

FIG. 28A shows a control grid in accordance with aspects of the invention and FIG. 28B shows a glucose control measure table in accordance with aspects of the invention;

FIGS. 42-44 show a hypo risk performance; pre-breakfast with the LGA=large, medium, and small, respectively;

DETAILED DESCRIPTION OF EMBODIMENTS

Figure 2:
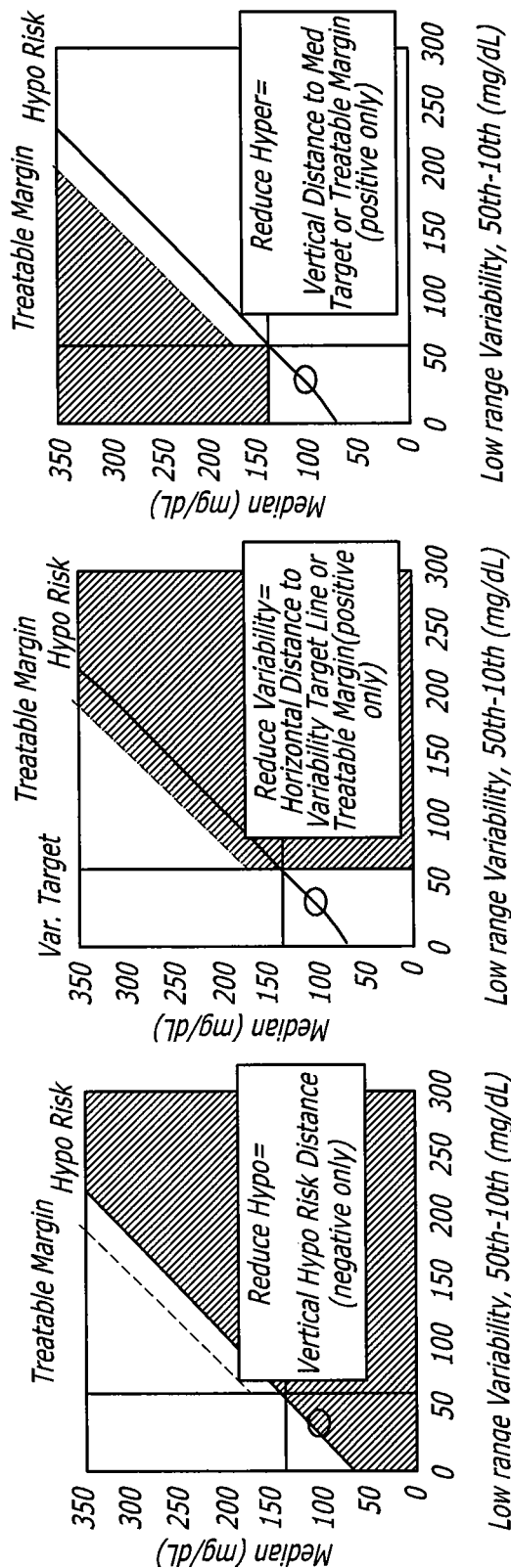
FIG. 2 is a combination of three graphs showing a reduction in hypoglycemia risk in the left diagram, reduction in variability risk in the center graph, and reduction in hyperglycemia risk in the right graph.

Reference will now be made in more detail to the drawings wherein like reference numerals refer to like elements throughout. In one aspect the invention provides a system and a method for the calculation and visualization of glycemic risks. With more particularity, the invention provides a system and a method for determining the glycemic risks of hypoglycemia, variability, and hyperglycemia for different times of the day for a patient, and allows investigation and illustration of how changes in glucose levels could affect those risks. The invention allows rapid identification of periods of the day needing a reduction in hyperglycemia, a reduction in hypoglycemia, and/or a reduction in glycemic variability.

The present invention improves the state-of-the-art by calculating glycemic risks based on thresholds that can be customized to fit patient-specific criteria. The disclosed visualization system and method enable rapid illustration of problems and support the training of patients and non-expert care givers in the assessment of glycemic control and options for intervention. The interactive controls reinforce illustrating the effect of different intervention strategies on glycemic risks during the day.

The current invention provides a means of guiding diabetes treatment intervention by calculating the clinical risk associated with three different parameters of glucose control:
1) hypoglycemia risk;
2) glucose variability risk; and
3) hyperglycemia risk.

In all cases, the clinical goal is to reduce and ultimately remove all sources of risk. These calculated, visual representations are provided to enable quick, efficient, and intuitive identification of problem areas. Furthermore, interactive simulations of glucose management interventions can be applied to illustrate the impact of different treatment approaches.

Calculation of "Risk Reduction Amount"

The calculation of clinical risk along the three parameters of low glucose, high glucose, and glucose variability is enabled by using the concept of the "Control Grid" shown in FIG. 1, which plots the glucose median relative to the difference of the median minus tenth percentile glucose for a given set of glucose measurements (defined as "Low Range Variability" or "LRV"), for use in mapping diabetes treatment recommendations. FIG. 1 shows the control grid 50 with various data elements.

The Control Grid 50 of FIG. 1 graphically represents the calculations to be undertaken, and illustrates the selection of targets needed to define the calculations. Adjustment of the targets is allowed to individualize the risk according to different attributes of the patient under consideration. Four potential thresholds are described here:
1) target median;
2) hypoglycemia risk curve ("Hypo Risk Curve");
3) target low range variability; and
4) treatable margin curve.

Target Median—the target median curve represents the overall level of glucose control, and would typically be in the range of 125 to 155 for most patients. Lower values are associated with reduced development of health complications, such as kidney, eye, and nerve disease.

Hypoglycemia Risk Curve (Hypo Risk Curve)—the hypoglycemia risk curve 52 is defined by a theoretically constant acceptable amount of hypoglycemia. Selection of a curve higher to the left on the control grid 50 would be indicated for a patient at higher-than-normal vulnerability to low-glucose complications (such as hypoglycemia unawareness), while a curve lower to the right might be indicated for a patient at lower-than-normal vulnerability (due to continuous glucose monitor use with low glucose alarms) or a patient with other high-priority goals, such as the case with pregnancy when the tradeoff of acute low glucose symptoms is preferred to the development of fetal complications.

Target Low Range Variability—the target low range variability line 54 may be adjustable or fixed. When adjustable, it may be constrained to be the x-axis value at the point of intersection 56 of the target median line 58 and the hypo risk curve 52, or could be located at a lower value than this intersection point. In all cases, having the target low range variability line farther to the left will indicate increased risk related to glucose variability, keeping everything else equal. Currently, there is limited direct clinical evidence on the long-term benefits of reduced glucose variability, though in the context of the control grid 50, reduction of low range glucose variability is a means to reduce hypoglycemia risk.

The Treatable Margin—the concept of "treatable margin" and the treatable margin curve 60 is the amount of median glucose reduction expected when a diabetes therapy is added. It is intended to serve as a "buffer zone" to avoid treatments that may result in a mismatch in clinical risk-benefit, where a reduction in hyperglycemia risk results in an unacceptably large increase in hypoglycemia risk. Typical treatment margins would be in the range of 10 to 50 mg/dL. Adjustment would be appropriate for different types of treatments or known treatment efficacy for a particular patient. For example, clinical experience may show a diabetes drug to have a 5 mg/dL mean reduction per unit dose in Patient A, yet a 10 mg/dL mean reduction per unit dose in Patient B.

Continuing to refer to FIG. 1, it is envisioned that any point on the control grid (x,y) 50 may be defined by either the centroid 62 or treatment recommendation point ("TRP") 64, or a mixture for different risk calculations. The centroid 62 is defined as the most likely location point on the control grid 50 derived from a sample of glucose measurements. Statistical methods can be used to estimate the uncertainty bubble around the centroid, and the uncertainty boundary 66 is defined by selecting an acceptable uncertainty (for example 5% for outlining a 95% confidence region). Alternately, functional definitions of the uncertainty bubble can be found empirically. The treatment recommendation point 64 is defined as the point on the control grid that is the intersection of the uncertainty boundary and the highest-valued hypoglycemia risk curve from the surface of continuous hypo risk. From these definitions, at any point on the control grid, defined as (x, y), calculations can be made for three categories of risk, or "risk reduction distances" (shown graphically in FIG. 2).

Referring now to FIG. 2 in detail, three graphs are presented, each of which shows risk reduction distances. The graph at the left shows reduction in hypoglycemia risk. The center graph shows reduction in variability risk, and the graph at the right shows reduction in hyperglycemia risk. In particular:

Left graph—Hypoglycemia Risk Reduction Distance ("Hypo RRD")=y—Hypo Risk Curve Median Value at x (negative values only). Because of the acute risk associated with hypoglycemia, (x,y) in this case may be defined as the TRP.

Center graph—Variability Risk Reduction Distance ("VRRD")=Minimum [x—Target Low Range Variability, x—Treatable Margin Variability at y] (positive values only)

Right graph—Hyperglycemia Risk Reduction Distance ("Hyper RRD")=Minimum [y—Target Median, y—Treatable Margin Median at x] (positive values only)

Figure 4:
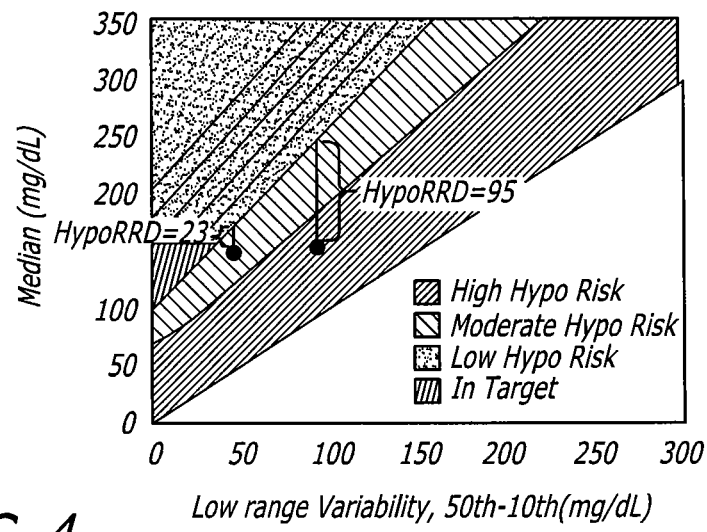
FIG. 4 shows examples of hypoglycemia risk reduction distances.

Using a functional definition of the uncertainty bubble which varies only on low range variability ("LRV") and number of glucose measurements results in a Control Grid shown in FIG. 3. Turning now to FIG. 3, there is shown a control grid using a functional form of the uncertainty boundary. Using this Control Grid, the Risk Reduction Distances are formulated with (x,y) as the Centroid by:

Hypo RRD=y—Moderate Hypo Risk Curve at x (negative values only) (see FIG. 4)

Figure 5:
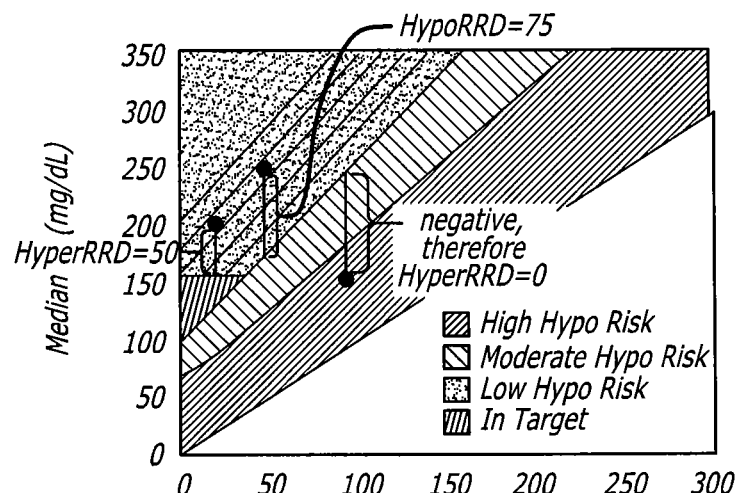
FIG. 5 shows examples of hyperglycemia risk reduction distances.

Hyper RRD=Minimum [y—Target Median, y—Moderate Hypo Risk Curve at x] (posi4ive values only) (see FIG. 5)

VRRD=x—Moderate Variability Line (positive values only) (see FIG. 6) Or, alternatively, to make VRRD and Hyper RRD mutually exclusive:

VRRD=Minimum [x—Moderate Variability Line, x—Treatable Margin Variability at y] (positive values only) (see FIG. 7)

Figure 8:
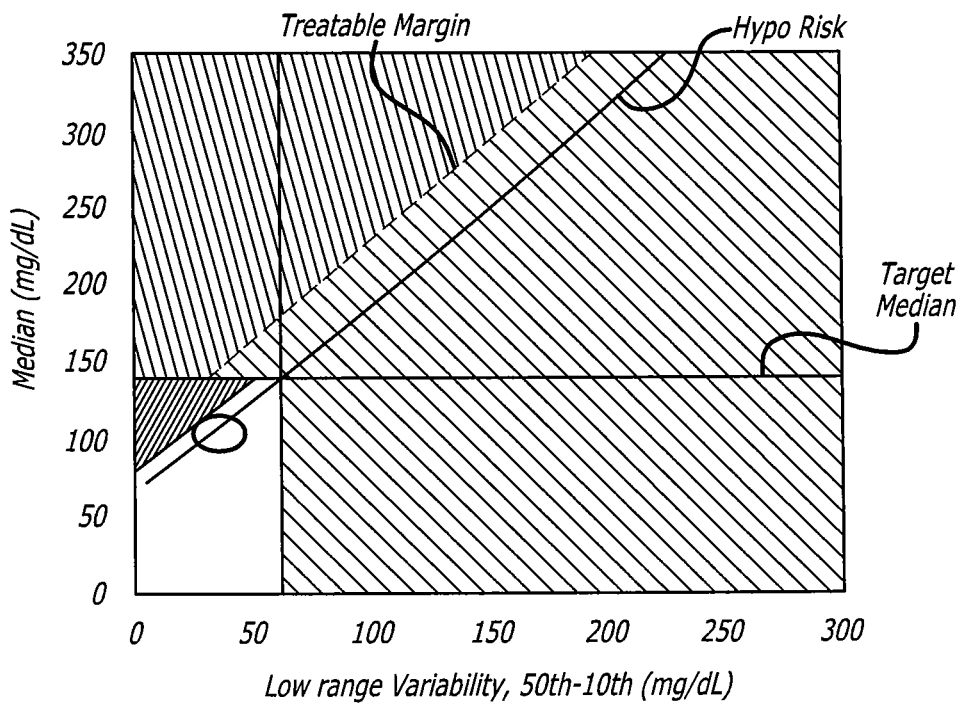
FIG. 8 provides an alternate design of zone definition.

Alternate Control Grid—given the definitions for calculating the three parameters of clinical risk, alternate underlying forms of the control grid regions may be designed in order to emphasize different clinical approaches, particularly balancing reductions in variability with reductions in hyperglycemia. One alternate design of zone definition is shown in FIG. 8 which would extend the Treatable Margin Curve in parallel to the Hypo Risk Curve all the way to the Target Median Line. This design emphasizes reductions in Variability over reductions in Hyperglycemia as one approaches the Target zone at higher low range variability. This may be preferable in order to reduce the possibility of "overshooting" the Target Zone, and ending up with excessive Hypoglycemia Risk.

Figure 9:
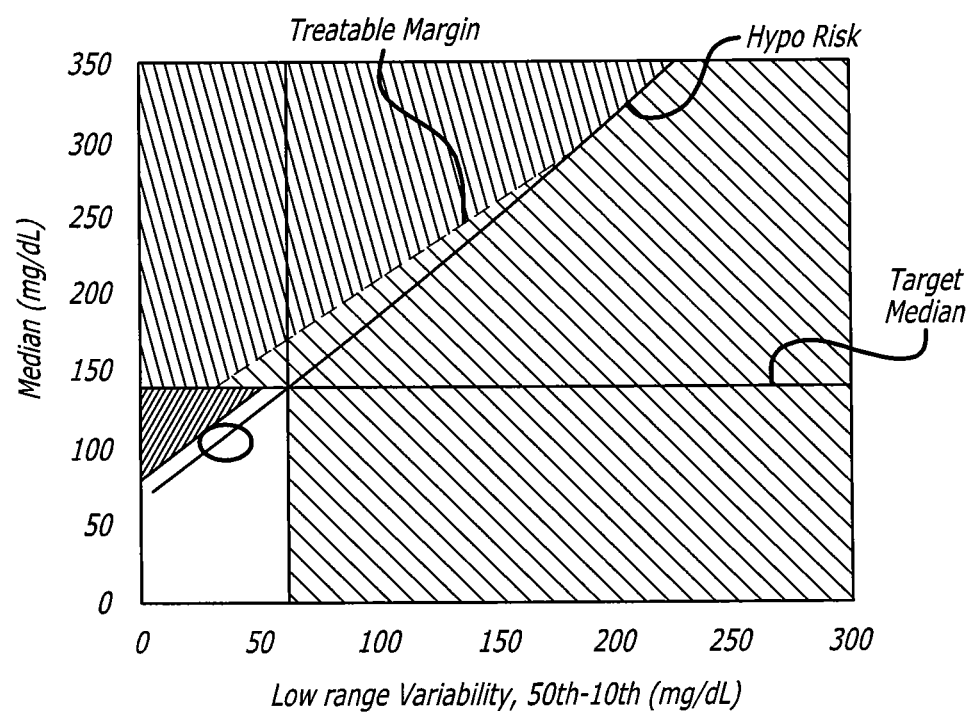
FIG. 9 shows another alternate design of zone definition.

Another alternate design of zone definition as shown in FIGS. 9 and 10 would have the Treatable Margin Curve become closer to, and eventually become equal to, the Hypo Risk Curve as low range variability increases. This design would emphasize reductions in variability at lower median and low range variabilities, but would emphasize reductions in Hyperglycemia at higher median and low range variabilities. This may be appropriate if it is deemed less acutely risky to address high glucose in the face of low glucose risk. This may be implemented either extending the Treatable Margin Curve to the Target Median line (FIG. 9) or to the Target Variability line (FIG. 10).

Yet another alternate design of zone definition shown in FIG. 11 would have the Treatable Margin Curve become farther away from the Hypo Risk Curve as low range variability increases. This design would further emphasize reductions in Variability at higher median and low range variabilities. This may be appropriate if it is deemed more acutely risky to address high glucose in the face of low glucose risk.

It is envisioned that (x,y) may be defined by either the Centroid or Treatment Recommendation Point, or other points on the Uncertainty Boundary, or a mixture for different Risk Calculations. For example, a Risk calculation may be performed, and then performed a second time with a point from the Uncertainty Boundary to add additional information about the certainty of the Risk calculation. This uncertainty could be displayed numerically (below) or graphically (see "Graphical Representation" below). For example:

Hypo RRD=10 mg/dL with a 95% confidence boundary of 35 mg/dL meaning that an increase of 10 mg/dL would move the Centroid above the Hypo Risk Curve, while an increase of 35 mg/dL would move the TRP above the Hypo Risk Curve.

Graphical Representation

Once Risk calculations have been performed, they may be displayed graphically for rapid interpretation. Depending on the nature of the glucose measurements, it may be appropriate to calculate risk during different time segments. For sensor-derived glucose, it is likely to calculate hourly determinations of risk. For strip-derived glucose, it is likely to calculate determinations of risk during several, for example four or more, time periods of the day.

Figure 12:
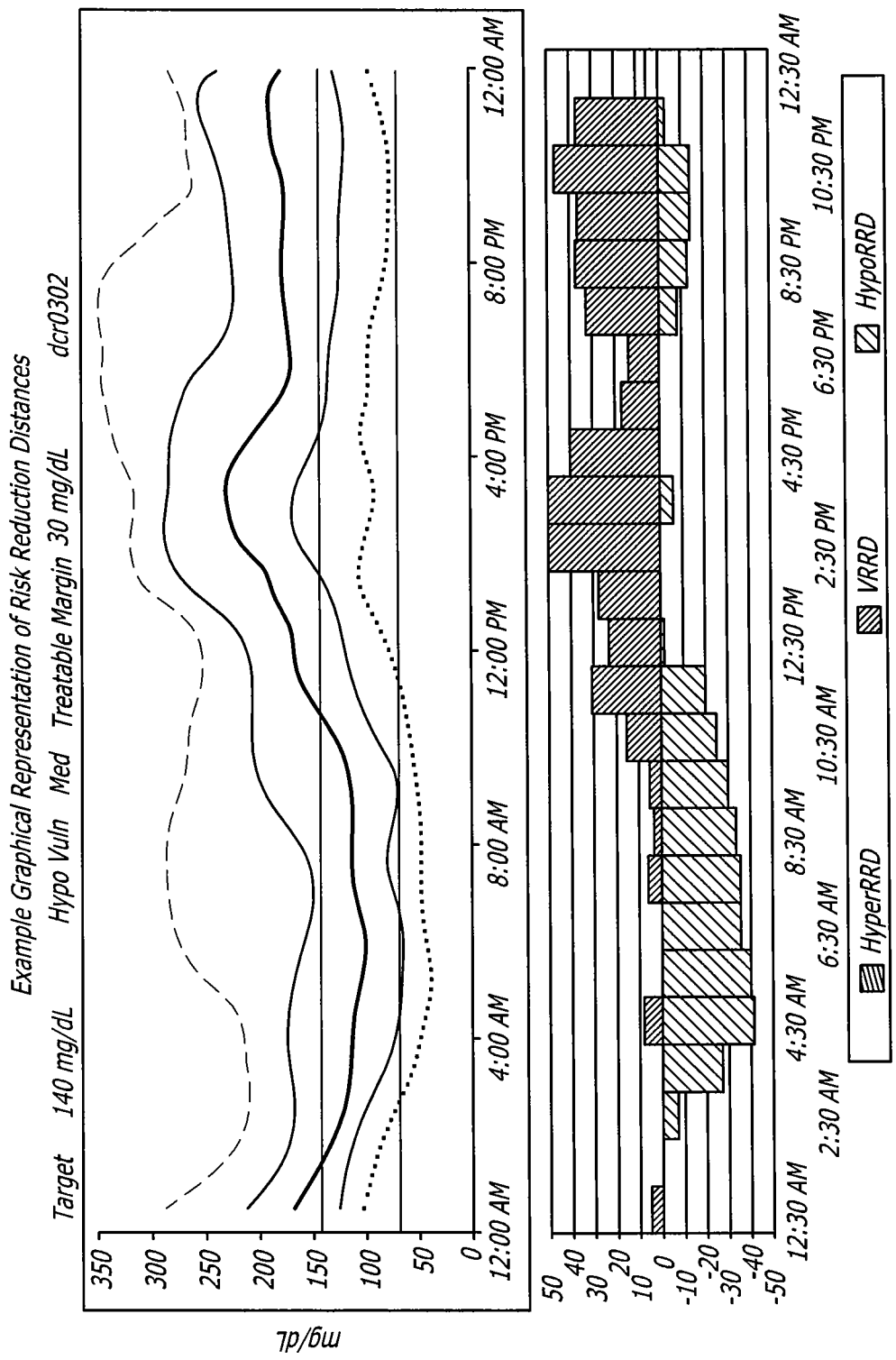
FIG. 12 is a design display of an example graphical representation of risk reduction distances.
Figure 13:
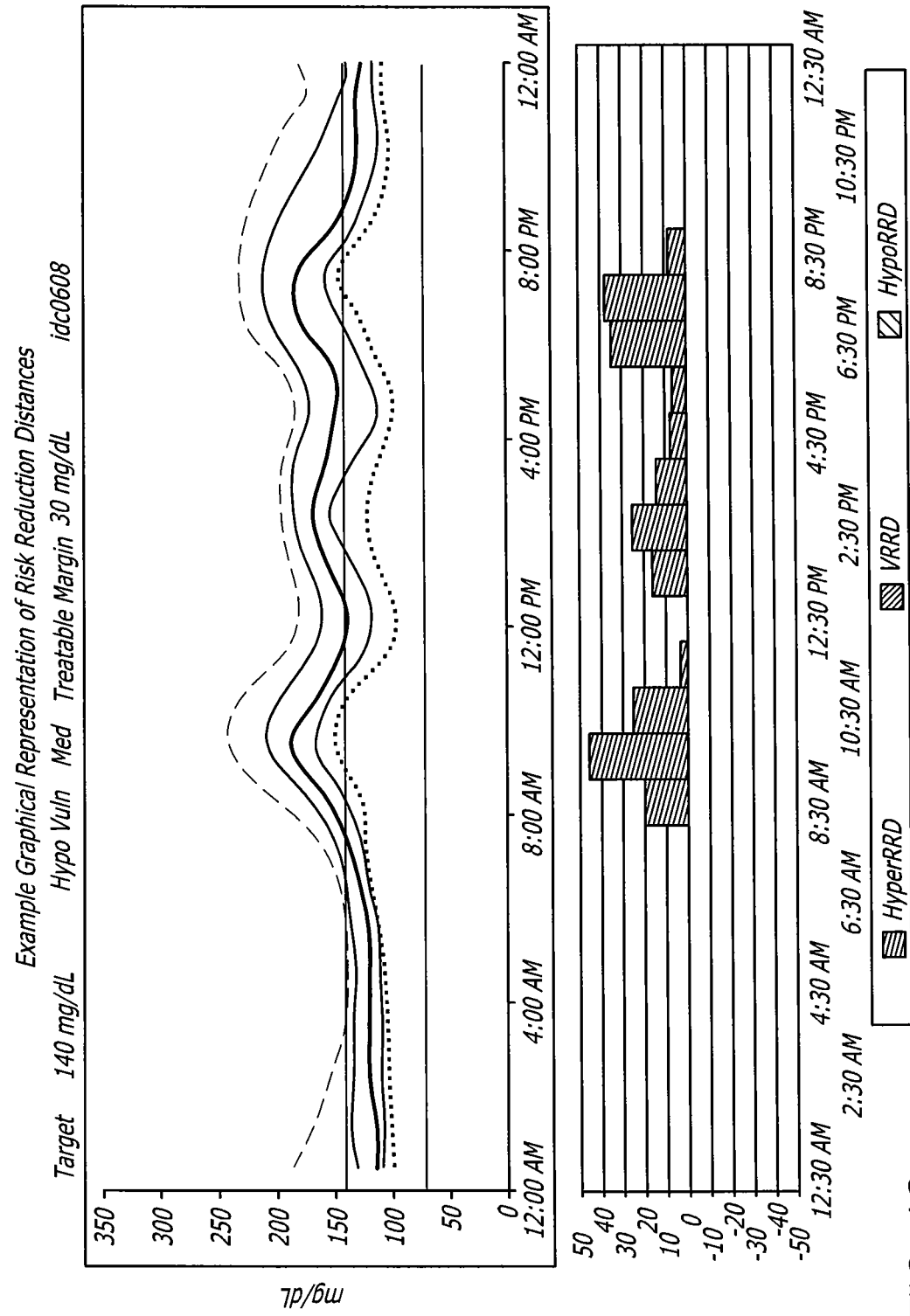
FIG. 13 is a design display of an example graphical representation of risk reduction distances.

In one embodiment of the proposed design displays shown in FIGS. 12 and 13 in which hourly data from a sensor is shown, three risk calculations are shown as vertically-aligned bars, with Hypoglycemia Risk below a horizontal line, while Variability Risk and Hyperglycemia Risk are above the line. One embodiment of the invention defines Hyper RRD and VRRD as mutually exclusive. In another embodiment, however, they could be calculated and displayed together (FIG. 13).

Figure 14:
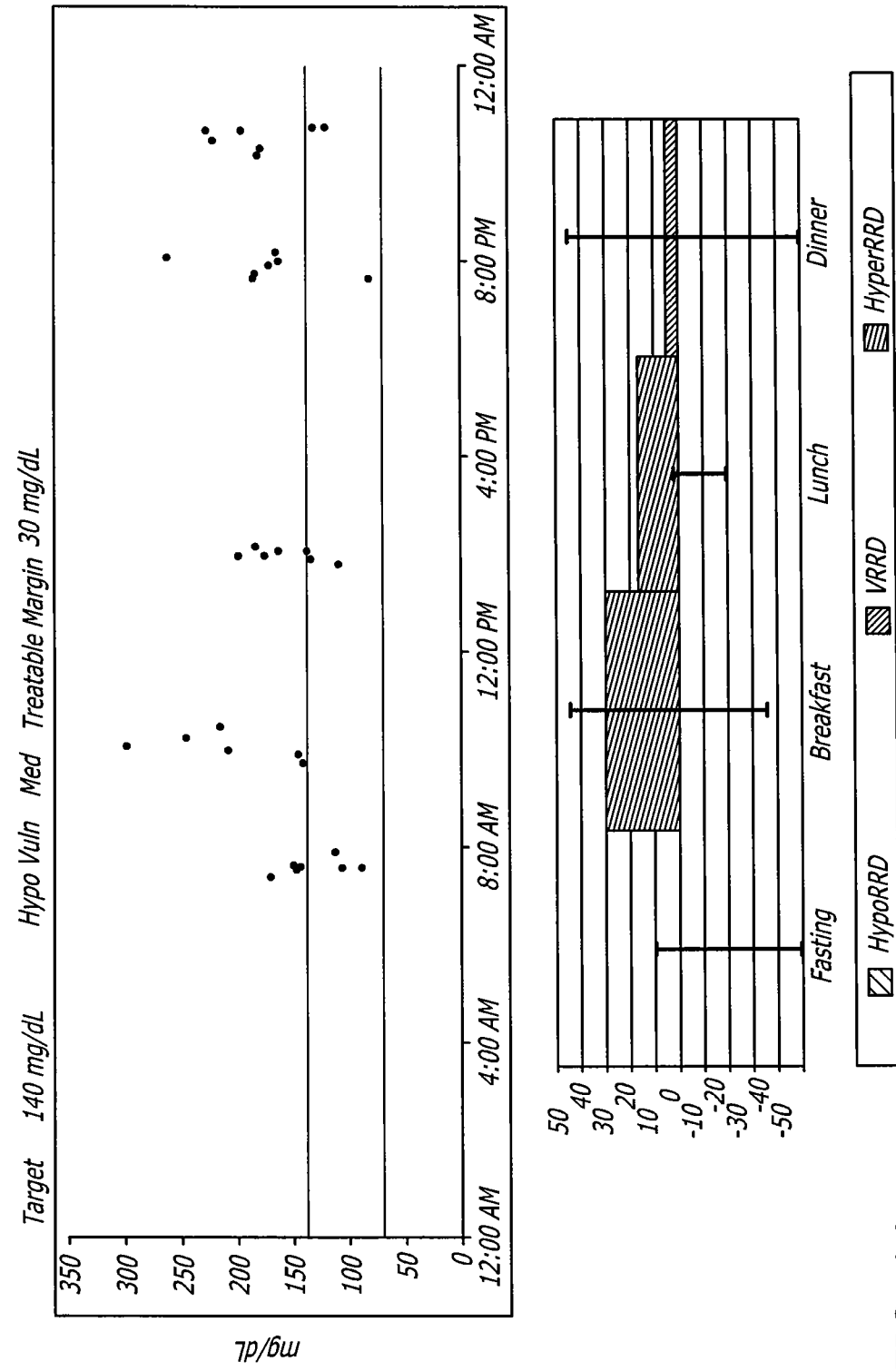
FIG. 14 provides design displays of risk reduction distances based on time periods from SMBG or a sensor.

In the graphical representation of risk reduction distances example shown in FIG. 14 based on time periods from SMBG or a sensor, the strip-derived glucose values are displayed with risk calculations in four time periods (during which the patient performed five measurements per day). In addition, the uncertainty is displayed as small "error bars" on the larger risk reduction bars.

Interactivity, "Simulation" and User Interface Controls

In order to better understand the risk associated with a set of glucose measurements, and the potential for altering the risk, additional controls have been designed. These controls allow interactive alteration of the data, allowing "what if" scenarios to be constructed. These allow further understanding of what changes may increase or decrease different sources of risk.

Control Actions

Figure 15:
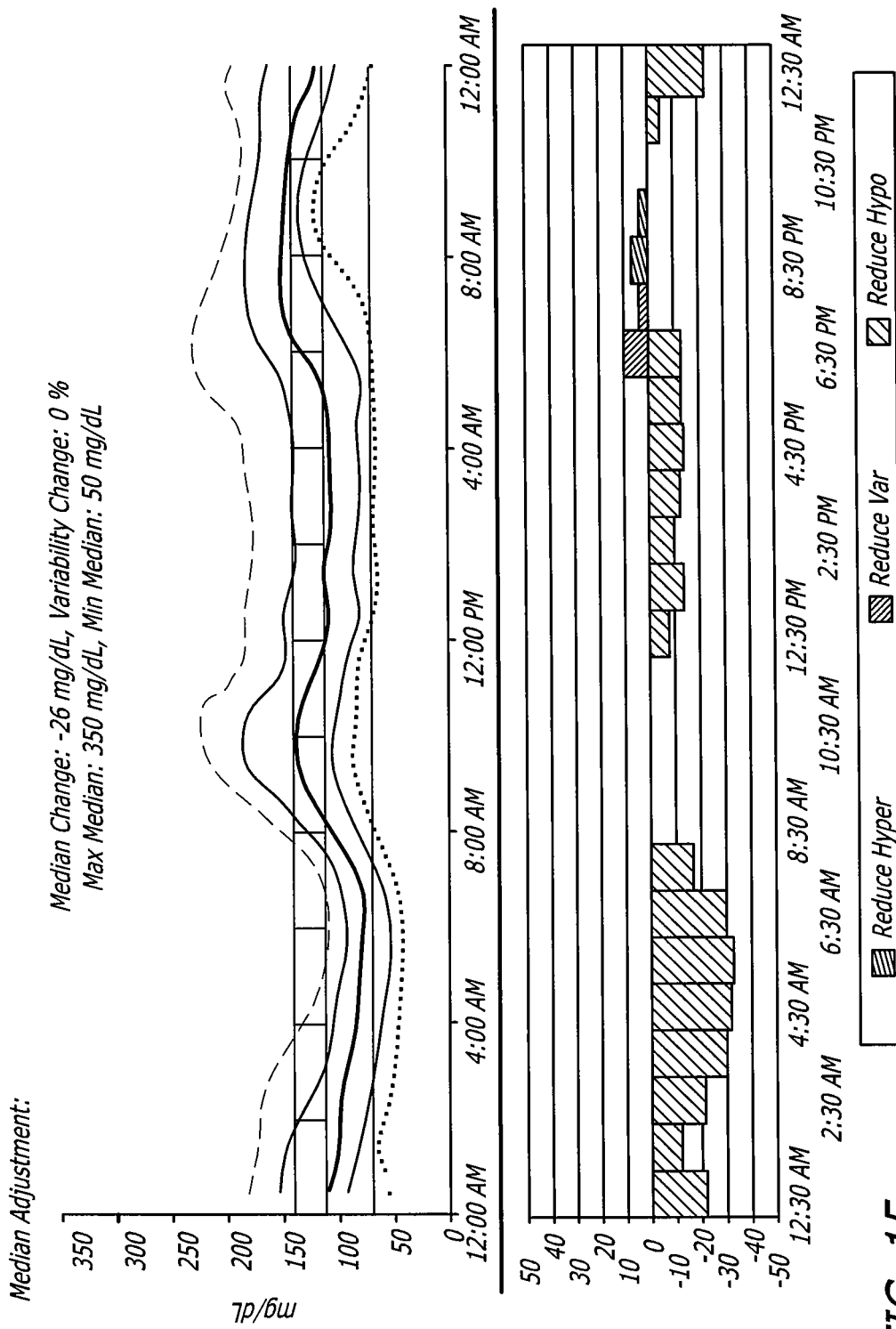
FIG. 15 presents a display of Median Adjustment having added visual features.
Figure 16:
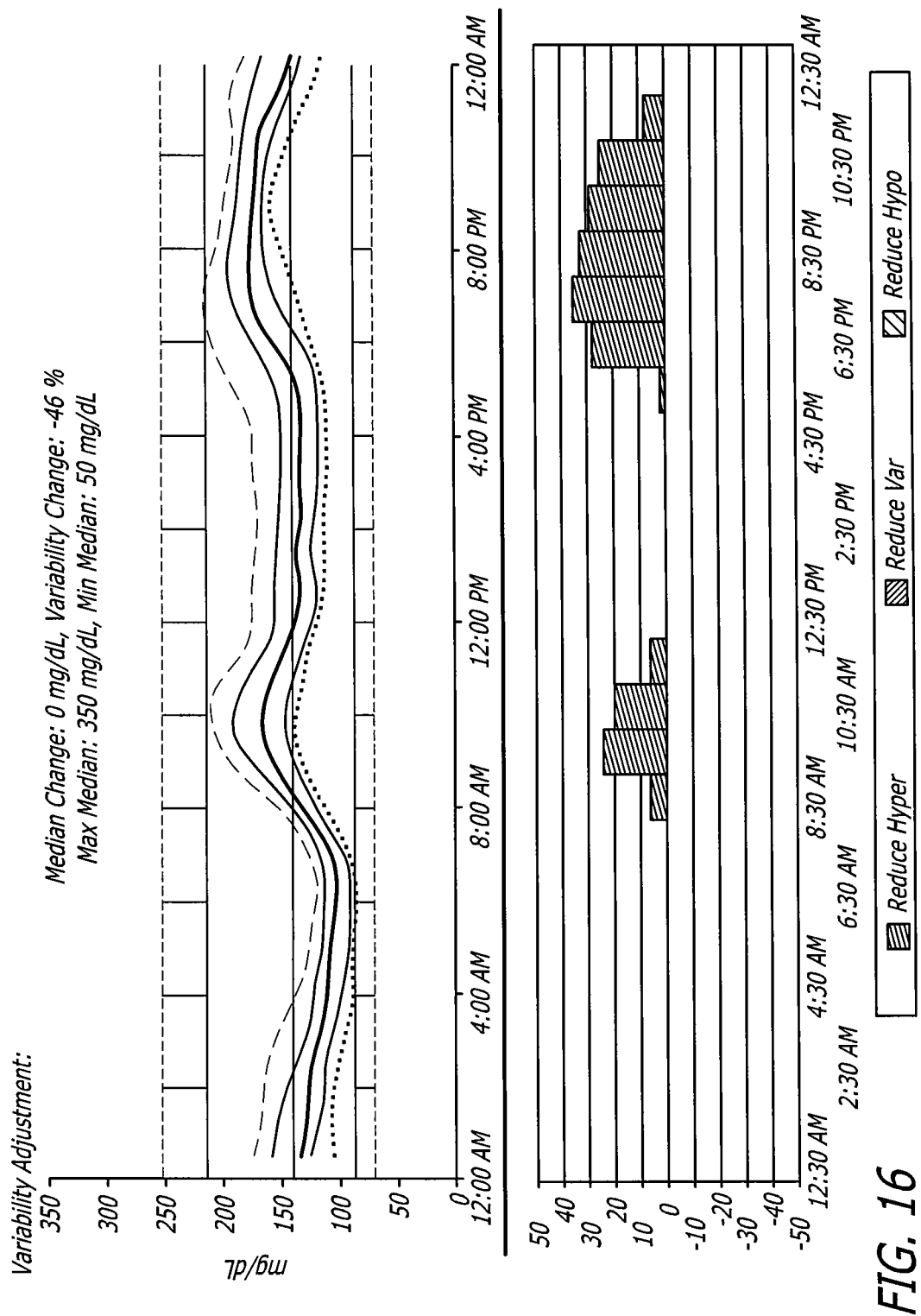
FIG. 16 presents a display of Variability Adjustment having added visual features.
Figure 17:
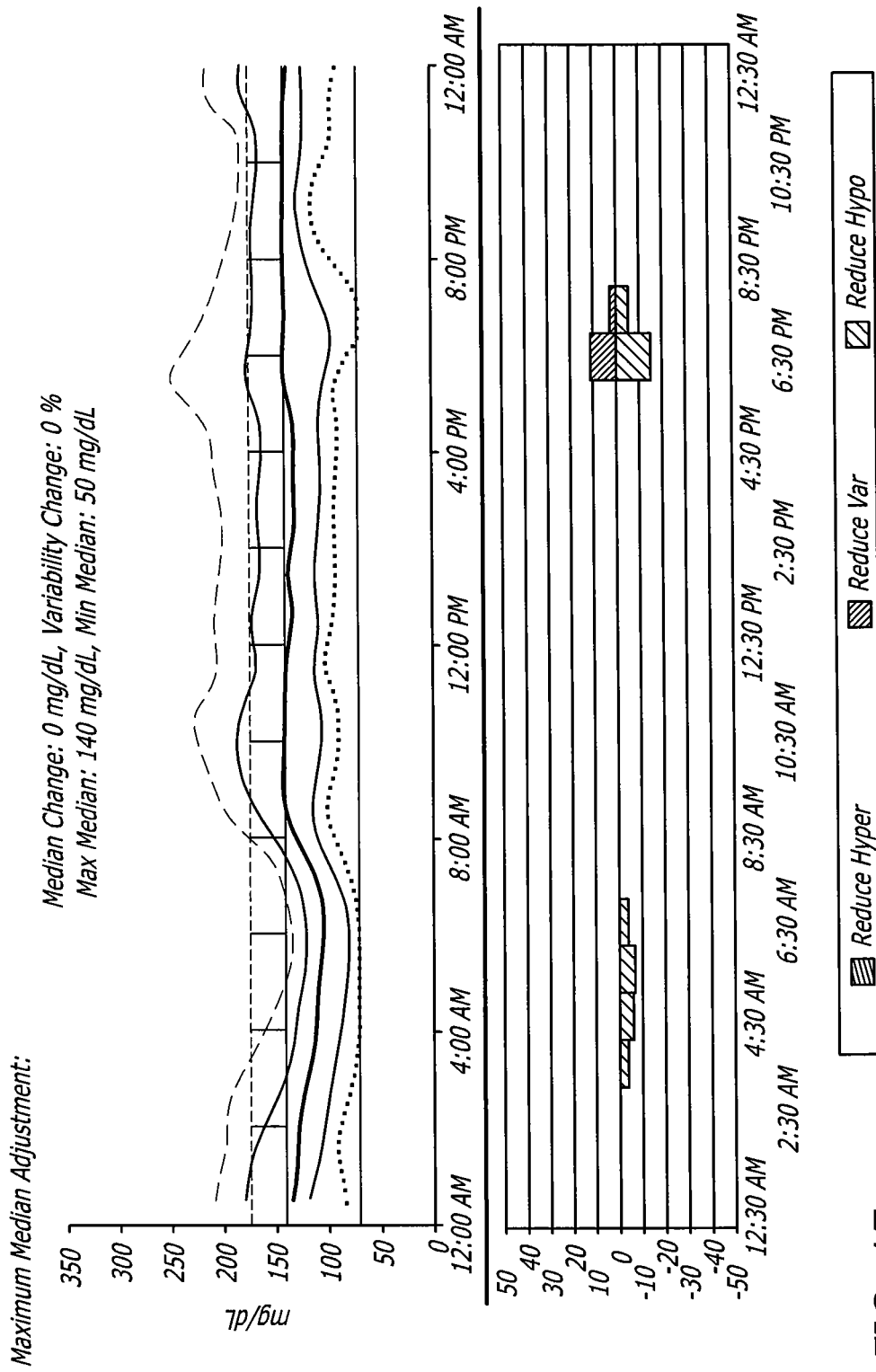
FIG. 17 presents a pair of displays of Maximum Median Adjustment having added visual features.
Figure 18:
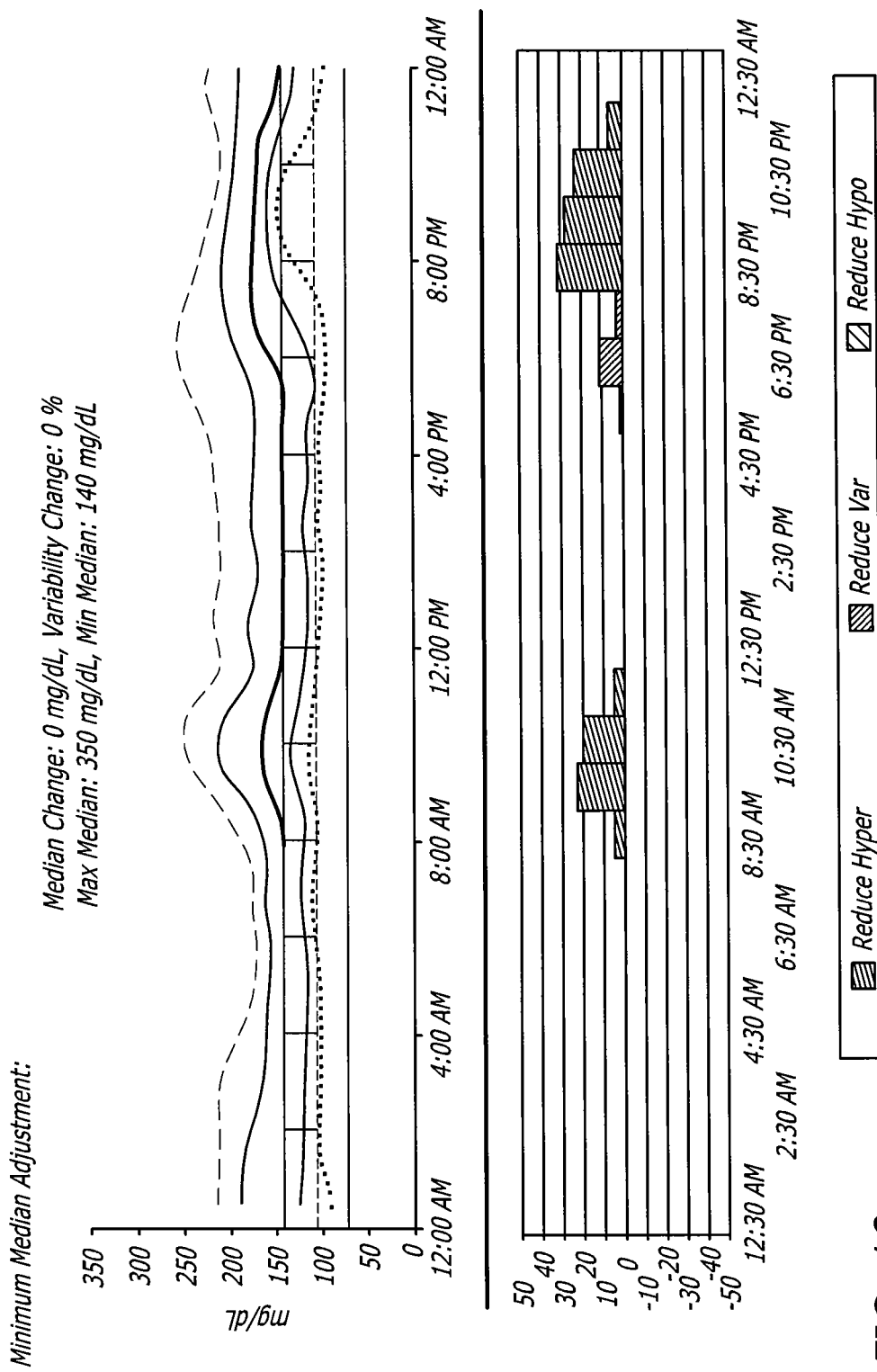
FIG. 18 presents a pair of displays of Minimum Median Adjustment having added visual features.

As an example, four controls are proposed: Median Adjustment, Variability Adjustment, Maximum Median Adjustment, and Minimum Median Adjustment. These may take the form of "scrollbars" for example. In addition, as the controls are adjusted, additional visual features may be added to the graph to emphasize what is being changed and by how much. For example, solid horizontal lines for "new" settings, dashed horizontal lines for "previous" settings, and vertical red lines to fill the space between the "previous" and "new." Below are examples of each control with added visual features:

FIG. 15 presents a display of Median Adjustment having added visual features, with the Median change at −26 mg/dL, Variability change of 0%, the maximum Median of 350 mg/dL, and the minimum Medial of 50 mg/dL;

FIG. 16 presents a display of Variability Adjustment having added visual features, with the Median change at 0 mg/dL, Variability change of −46%, the maximum Median of 350 mg/dL, and the minimum Medial of 50 mg/dL;

FIG. 17 presents a display of Maximum Median Adjustment having added visual features, with the Median change at 0 mg/dL, Variability change of 0%, the maximum Median of 140 mg/dL, and the minimum Medial of 50 mg/dL;

FIG. 18 presents a display of Minimum Median Adjustment having added visual features, with the Median change at 0 mg/dL, Variability change of 0%, the maximum Median of 350 mg/dL, and the minimum Medial of 140 mg/dL;

Touch Screen Controls

With the widespread adoption of touchscreen devices, these controls may be embedded into the graph itself. For example, placing and dragging a single finger in the plot area could activate the Median Adjustment control, with the vertical component of dragging motions being applied as the Median Adjustment. Placing two fingers in a "pinching" position on the plot area could activate the Variability Adjustment control, with "closing" and "opening" decreasing and increasing the variability, respectively. The Maximum Adjustment control could be activated by placing a finger above and outside of the plot area and dragging down into the plot area. Similarly, the Minimum Adjustment control could be activated by placing a finger below and outside of the plot area and dragging up into the plot area.

Figure 19:
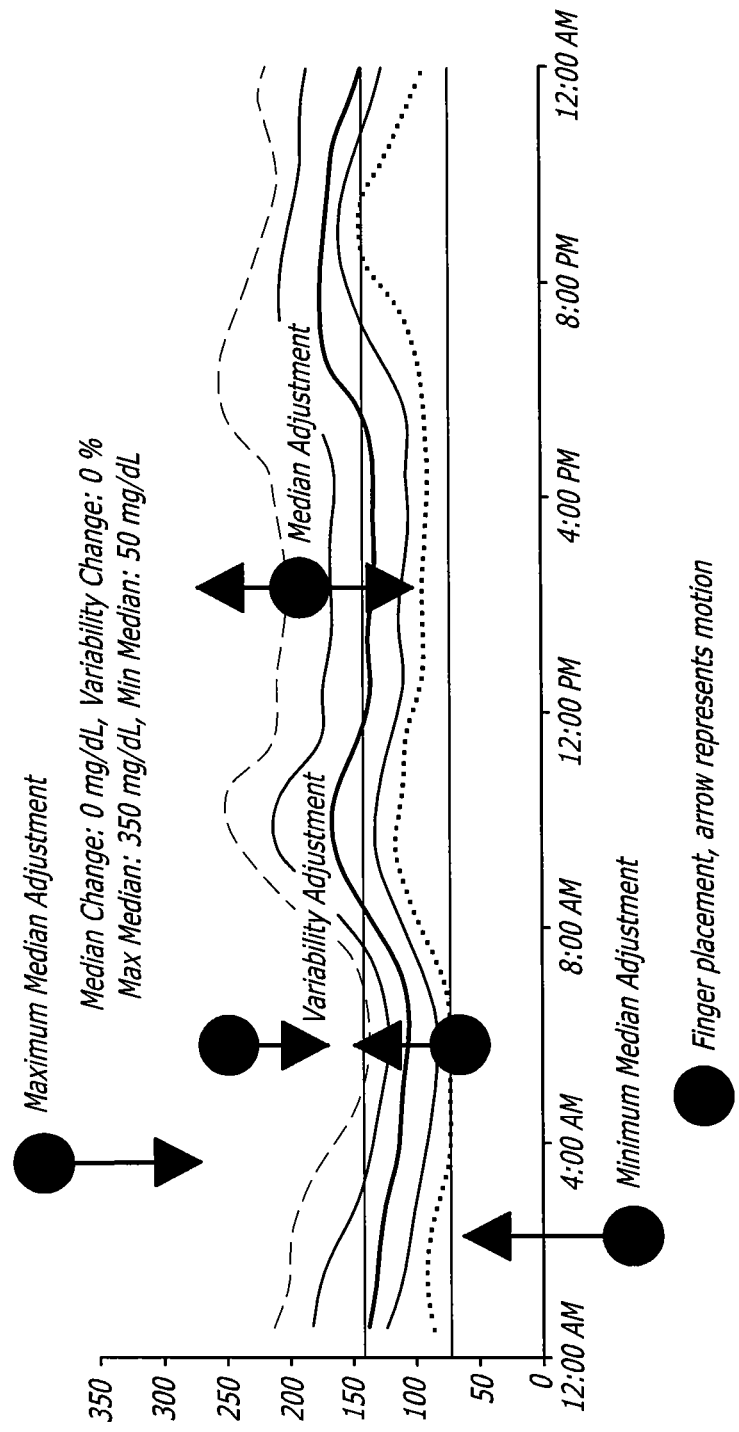
FIG. 19 shows a touchscreen display with examples of finger touchscreen controls.

Such touchscreen controls are shown on FIG. 19 by grey circles with arrows. In particular, finger placement shown with the grey circles includes Maximum Median Adjustment, Minimum Median Adjustment, Variability Adjustment, and Median adjustment. Other controls are possible.

Continuing with a system and method related to hypoglycemia and hyperglycemia determination, there is also provided an improved estimate of average glucose using HbA1c and CGM. In this aspect, CGM data is used to more accurately describe the relationship between average glucose and HbA1c results. The relationship between HbA1c and average glucose is variable from person to person. In spite of this, clinicians use one "population average" equation to relate one to the other. However, CGM data yields a good independent estimate of average glucose which, in tandem with HbA1c results, allows the development of an equation tailored to an individual.

ACT is hemoglobin that has been glycosolated, or modified by the addition of glucose. It is commonly known as HbA1c or A1c. It is sometimes referred to as glycosolated hemoglobin A1c or glycated hemoglobin. The normal level of A1c in people without diabetes is approximately 4% to 6%.

HbA1c is a test that indicates average blood sugar over the past eight to twelve weeks. Its value, in percentage, is linked to average blood sugar, in mg/dL, by the following equation:

$$\text{Average Glucose (mg/dL)} = 28.7 \cdot \text{HbA1c (\%)} - 46.7 \quad (1)$$

This is an average relationship based on a population of people; the relationship for individual subjects varies significantly. It has been determined, however, that individual relationship deviation from the average relationship is constant over time, and can be calculated provided that an independent estimate of the average glucose can be obtained.

When individual glucose data is provided by finger sticks, there are often not enough values to provide a good estimate of the average glucose. Thus, the results of an A1c test are converted to average glucose via Equation (1), and can be used to check the average finger stick glucose. Any significant discrepancies are blamed on meter inaccuracy or insufficient data.

If instead a CGM system is used to collect data, the average glucose value can be calculated with more confidence. A significant difference between this value and the value provided by the A1c test can be ascribed to individual variation from Equation (1), and corrected coefficients to Equation (1) can be estimated. This correction can take the form of an altered slope and/or an offset. If a slope and an offset must be found, then a minimum of two A1c tests taken several months apart, along with CGM for the same time periods, must be used. If two tests are taken, we have $$G_1 = m^*A_1 + b, \text{ and } G_2 = m^*A_2 + b \quad (2)$$

and slope, "m," and offset, "b," can be determined from the CGM average glucose, "G", and the measured A1c, "A." If there are more than two A1c tests and contemporaneous CGM traces, fitting a 1st order polynomial, by least squares for example, will determine the slope and offset. The independent variable in the least squares calculation is the more accurate measurement of the two.

Given a slope and an offset, Equation (2) can be used to estimate the average glucose for an individual patient based on A1c measure for that same period. If finger sticks are also available, blood glucose values can be combined by using a weighted average. It is necessary to estimate how many finger sticks an A1c measurement is equivalent to. Once this is done, the weights for the average are obvious. In addition, the median glucose is now easily calculated.

Any estimate has inherent uncertainty. If CGM use coincides with multiple A1c tests, the uncertainty in the modified coefficients can be quantified. In any case, the use of Equation (2) will make subsequent estimates of average glucose from measured A1c more accurate. In addition, the Equation (2) can be used "in reverse" to provide more accurate estimates of A1c from finger stick values when a current A1c test result is not available. Also, note that if three or more A1c tests are available, along with CGM during the same time period, then least squares techniques may be used to determine the best values for m and b. Also, note that models other than the two parameter linear model may be used to define the relationship between average glucose and A1c.

If the subject reverts to using finger sticks, Equation (2) can be used to make a more accurate estimate of the average glucose. This can be used as the average glucose value in any subsequent analysis. This allows us to specialize finger stick use to estimate only variability. Finger stick timing could be adjusted, relative to meals for example, to produce an estimate of variability that agrees with the estimate from the CGM. However, this might make the finger stick estimate of the average glucose very inaccurate.

If the finger stick estimate of the average glucose is still accurate enough, disagreement between the average glucose from A1c and the glucose average derived from finger sticks can be used as a data quality or data insufficiency test. The significance of the deviation can be determined from the uncertainty in the estimates of the coefficients of Equation (2).

In yet another aspect of the invention, a theoretical calculation of glycemic risk based on the observation that CGM data follows a probability distribution is provided.

Variability is known to be a risk factor for hypoglycemia and hyperglycemia. However, since variability is difficult to characterize and measure, it has largely been ignored, especially in determining treatment dosages. The invention uses the observation that glucose levels follow a probability distribution over time to quantify glycemic risk. Thus, variability is shown to be as important as average glucose level.

A glycemic target range is a common way to measure and encourage glucose control. All glucose values below the lower limit are considered to be hypoglycemic, and all values above the upper limit are considered to be hyperglycemic. There are many ways of using glucose values to assess the risk of hypoglycemia and hyperglycemia. The invention describes a way of using an assumed distribution of glucose values to theoretically calculate measures of hypoglycemic and hyperglycemic risk, and considers certain extensions such as time correlation and bias correction.

Glycemic risk calculations can be divided into two broad classes: parametric and nonparametric. A parametric calculation assumes that the glucose values follow a distribution, a Lognormal or a Gamma distribution for example, and uses the data to calculate the parameters of the distribution. We have found that the most practical distributions are determined by two parameters (mean and standard deviation, usually), however, there are distributions that need fewer or more parameters to define them, and they could also be used. From these parameters, all glycemic risk estimates can be derived. A nonparametric calculation does not assume any distribution. The risk estimate is calculated directly from the data. The advantage of a parametric calculation is that less data is required to make a reasonable estimate. The disadvantage is that the data must follow the assumed distribution.

Although less data is necessary to make a parametric estimate, a relatively large data set is necessary to establish the validity of such a model. For example, if we think that that glucose values fit a normal distribution, it takes a lot of data from many subjects to confirm the hypothesis. CGM makes it practical to collect data in the necessary quantities.

Most glycemic risk estimates involve the rate of accumulation of data points beyond a single threshold, either hypoglycemic or hyperglycemic; for example, we could use the area of data below the hypo threshold per week.

The general nonparametric formula for risk is:

$$R = \frac{\text{Sampling Interval}}{\text{Collection Time}} \sum_i |G_i - G_0|^n$$

where only the data points ($G_i$) beyond the threshold ($G_0$) are included in the sum, but the collection time includes all data points. The exponent, n, can take nonnegative values. Larger values of n weight more extreme data points more heavily. For example, if n=0, all points beyond the threshold are weighted equally and R is the fraction of points beyond the threshold. If n=1, R is the rate of area accumulation beyond the threshold; points are weighted according to their distance from the threshold.

The parametric formula for hypo risk is:

$$R_T = \int_0^{G_L} (G_L - x)^n P(x) dx$$

The hyper risk formula is similar:

$$R_H = \int_{G_H}^{\infty} (x - G_H)^n P(x) dx$$

Here, P(x) is the assumed distribution with the distribution parameters determined by the data; $G_L$ and $G_H$ are hypoglycemic and hyperglycemic thresholds. Here, as with the nonparametric formula, a larger values of n weights the more extreme values more heavily. Note that if there are no data values beyond a threshold, the nonparametric formula yields R=0, while the parametric formula always gives a positive result.

One pair of nonparametric glycemic metrics that does not follow the previous discussion is LBGI and HBGI, as defined by Boris Kovatchev and William Clarke, et al., "Quantifying Glucose Variability in Diabetes via Continuous Glucose Monitoring: Mathematical Methods and Clinical Application", Diabetes Technology and Therapeutics, 2005; 7:849-862. Here, the hypo and hyper limits coincide at 112.5 mg/dL and a complicated weighting of the distance from the threshold is used in the sum. For this case, we can apply the same parametric formulas:

$$R_L = \int_0^{G_L} f(x) P(x) dx$$

where f(x) is the LBGI function for a single glucose value. The formula for $R_H$ is analogous.

So far, all of the formulas in this paper have ignored possible time correlations. One elaboration of the nonparametric method is to insist that a minimum amount of time be spent beyond a threshold before the subject is considered to be out of euglycemia. This will also provide some protection from measurement artifacts.

For example: suppose the hypo threshold is 70 mg/dL. The subject is not considered to have entered hypoglycemia unless he has spent:
  60 continuous minutes at or below 70 mg/dL, or
  40 continuous minutes at or below 60 mg/dL, or
  30 continuous minutes at or below 50 mg/dL, or
  20 continuous minutes at or below 40 mg/dL.

Here, we have assumed a sampling interval of ten minutes. No single data point, no matter how extreme, can contribute to the hypoglycemic risk. Once in hypo, subsequent points below the threshold add to the risk. There is a similar constraint to leaving hypoglycemia: no isolated data point above the hypo threshold can take the subject out of hypo.

The parametric formulas do not include time. Data is used only to calculate the distribution parameter values. Thus, time correlations cannot be included in the parametric method.

One important difference between parametric and nonparametric methods has been mentioned: parametric methods use data more efficiently. We will now expand on this idea. Glucose data is used to make estimates of glycemic risk. Inherent in the idea of estimate is uncertainty: how close to the "truth" do we expect our estimate to be? If we had densely sampled data, we could calculate the true value of any of our defined risks using the nonparametric formulas.

If a relatively sparse subsample of this data is available, an estimate of the risk can be made. As the number of data points decreases, the estimate uncertainty increases. The magnitude of the uncertainty seems to scale as the reciprocal of the square root of the number of data points. These nonparametric estimates are unbiased. If a number of different samples are taken from the complete set of data, the average of the estimates converges to the truth as the number of estimates increases, or as the sample size increases.

Parametric estimates are different. The uncertainty in the estimate for a given sample size is less than for nonparametric estimates, but the parametric estimator might not be unbiased. This remains true even when all of the data is used. The value of the bias can be found by assuming that the true value is found using the nonparametric method with many data points. This "truth" is compared to results obtained from the parametric method using a certain number of points collected during a certain portion of the day. We find that the bias is a function of sample size and time of day. Compensating for this bias will increase the accuracy of a parametric estimate.

Data collection compliance is always an issue. The ability to get a useful result with relatively few samples is an important advantage. In addition to using a parametric method, we can also use a Structured Test Protocol (STP) to get the most from each data point. With STP, we define preferred times of testing, the number of tests per day, and the number of days. The test times can be defined either relative to a meal or by the clock. We have tried eight tests per day over seven days, ranging from before breakfast to four hours after dinner, with good results. We have also tried four tests per day over seven days. With half the number of points, the uncertainty is larger, but the results are still clinically useful.

Thus, parametric models are more efficient in their use of data than nonparametric methods, making it possible to obtain useful predictions with Structured Test Protocols of finger sticks in a reasonable number of days. CGM data enables the construction of parametric models by providing the large numbers of data points.

A further aspect of the invention involves tailoring SMBG test schedules based on results from CGM wear. The invention uses the results of brief periods of CGM wear to generate SMBG test schedules that focus on periods of high variability and hypoglycemia risk discovered by analysis of the CGM data. The invention maximizes the utility of SMBG testing by focusing SMBG test schedules on periods of high variability and hypoglycemic risk.

Some of the problems with SMBG testing schedules are patient compliance and limited data. Patients may not comply with an SMBG testing schedule because BG testing can be painful and inconvenient. In order to maximize compliance, SMBG test schedules generally occur over a short time period with just a handful of SMBG tests. This leads to the second problem, limited data. Blood glucose testing schedules will produce relatively small data sets which can introduce a high uncertainty to the calculated median glucose, calculated low range variability, and calculated hypoglycemia risk. The higher the uncertainty, the less aggressive treatment recommendations can be in order to be sure that the hypoglycemia risks are avoided.

Additionally, another problem caused by collecting a small amount of data is that SMBG measurements can either be focused on a small amount of small time periods or large time periods, but not both. For example, an SMBG test schedule might focus on median and variability at fixed times, for example one hour after meals, requiring the patient to perform tests every day for one to two weeks, one hour after each scheduled meal. With such a test schedule, the median and low range variability can be calculated relatively accurately, but only for one hour after each scheduled meal. Little information will be learned about other time periods (such as two hours after each meal). Alternatively, the SMBG test schedule may follow a progressive schedule requiring the patient to test at various times of the day. For example, the schedule might ask for the patient to test at 7:00 AM, 11:00 AM, 3:00 PM, and 7:00 PM one day, 8:00 AM, 12:00 PM, 4:00 PM, 8:00 PM the next, etc., for the one to two weeks. This type of SMBG test schedule can produce a relatively accurate portrayal of Median and Low Range Variability during the entire range of times tested (note: it is unlikely that a patient will comply with a testing schedule that requires a test during sleeping hours day after day), however calculations of Median glucose, Low Range Variability and Hypo Risk will have a very high uncertainty for any specific time of day.

The invention tailors the test schedules to focus on problem times (times of high variability or hypoglycemic risk) discovered by a short period of continuous glucose monitor wear. This addresses the issues of limited data and compliance because the SMBG schedules can be shorter, thus leading to greater compliance, and the data that is collected is the important data, which derives more value from the limited supply of data. Additionally, by identifying the time periods of interest it can help identify when it is appropriate to focus on small time periods, and which ones, and when it is appropriate to focus on larger time periods.

SMBG testing schedules are assigned to patients by HCPs in order to gather data so that the HCPs can make recommendations to patients regarding therapy and lifestyle changes. Key metrics that can be ascertained by this SMBG testing are median glucose, Low Range Variability and Hypoglycemia Risk. Typically, a key therapy goal is to reduce a patient's median glucose while avoiding the risk of the patient spending significant time in hypoglycemia or experiencing a severe hypoglycemia incidence. The higher a patient's Low Range Variability, the higher the Median glucose the patient will need to maintain in order to avoid these incidences of hypoglycemia.

Continuous Glucose Monitors are also given to patients by HCPs in order to measure a patient's Median glucose, Low Range Variability, and Hypoglycemia Risk. Using a Continuous Glucose Monitor most of the problems associated with Discrete Blood Glucose ("DBG") testing can be addressed. With a continuous blood glucose monitor, a problem with patient compliance typically does not exist. There is enough data to measure Low Range Variability to very small time periods, typically as short as one hour. Additionally, CGM systems provide data while the patient is sleeping. The drawbacks of Continuous glucose monitoring are that it is expensive, it can be uncomfortable, and that patients must typically wear a device all the time, which many are very reluctant to do.

This invention supposes that HCPs will only prescribe continuous monitors for short time periods. It proposes that the results from the CGM wear be used to tailor specific SMBG test schedules that target the areas of interest (usually times of high Low Range Variability, or hypoglycemia) identified by analysis of the CGM data. The tailored SMBG test schedule may be used to monitor the effect of lifestyle or therapy changes prescribed by the HCP, or it may simply be used to monitor more closely an ongoing problem.

Note: in the cases mentioned below, the use of progressive and fixed time SMBG testing schedules are mentioned. Many of the cases mentioned below confine all testing to specific time periods. In these cases, it may not be too onerous to increase the number of tests per time period as the overall number of tests will not increase.

Possible Issues Identified by CGM Results and SMBG Tailored Test Schedules

1. CGM Identified Issue—The CGM identifies that Low Range Variability and Hypo Risk are scattered throughout the day with nothing distinguishing any particular days or time periods.
  Tailoring—Assign a progressive SMBG schedule as previously described: ask for the patient to test at 7:00 AM, 11:00 AM, 3:00 PM, and 7:00 PM one day, 8:00 AM, 12:00 PM, 4:00 PM, 8:00 PM the next . . . etc. for the 1 to two weeks.

2. CGM Identified Issue—The CGM identifies that there is high Low Range Variability between specific meal times or during the fasting period, with no recurring patterns regarding days of the week and the period of time of the variability cannot be more specifically specified.
  Tailoring—Assign a progressive SMBG schedule as previously described, but confine it to the in between meal periods (or fasting) of interest. If some time periods do not display variability then no testing need be done in those time periods which means either a shorter SMBG schedule for the patient or alternatively more tests can be scheduled within the periods of interest, thus producing more accurate results.

3. CGM Identified Issue—The CGM identifies that low range variability occurs during short time periods between meals. Example, one hour after certain meals.

Tailoring—Assign a fixed time SMBG schedule around the time periods of interest. For example in the case where variability occurs about 1 hour after lunch, assign an SMBG test schedule which asks for tests distributed over that specific time period.

4. CGM Identified Issue—The CGM identifies areas of high low range variability and/or hypo risk during specific hours of the day (ex. 4 AM-5 PM).

Tailoring—Schedule tests that during a one to two week period occur at various times during the 4-5 PM window (ex. 3:45 PM-5:15 PM). The results of this testing should produce relatively accurate information regarding the patient's hypoglycemia incidences and low range variability during this time. Note, this concept can be extended to sleeping hours if severe frequent incidences of severe hypoglycemia are detected. One would assume that a patient who frequently experiences severe hypoglycemia incidences will be motivated to test even during sleep hours due to the risk of coma and death during these instances. For example, if the time interval of interest is 4:00 AM to 5:00 AM a similar SMBG test schedule can be created. Having this tailored test schedule limits the inconvenience of having to wake up during sleep.

5. CGM Identified Issue—The CGM identifies areas of high Low Range Variability during specific days of the week (for example, Saturdays).

Tailoring—Assign SMBG testing to the day of interest. For example, the patient should be asked to test one day a week (for example, Saturday) for five to ten weeks with tests scattered at various times through the day.

6. CGM Identified Issue—The CGM identifies areas of high Low Range Variability or hypoglycemia incidences during specific days of the week at specific times (for example, 6 PM-8 PM on Saturdays).

Tailoring—Assign SMBG testing to those specific hours of the specific days of interest.

7. CGM Identified Issue—The CGM identifies post prandial peak time of meals. Example embodiment: Divide data into different meal segments, or to rely on patient's meal marker input, or a combination of both. Analyze each meal segment data to obtain a distribution of time-to-peak durations. For segments that lack a meal marker, the start is identified as the average timestamp of the $5^{th}$ percentile glucose value in that segment, and the peak is identified as the average timestamp of the $95^{th}$ percentile glucose value in that segment.

Tailoring—Set SMBG test reminder at the optimal duration after a meal-related SMBG event marker. Different meal times may require different duration settings.

8. CGM Identified Issue—Analysis of CGM finds patterns in the data taken when it would be convenient to test (e.g. during waking hours) such as values at specific times [absolute or meal-relative] or fluctuations in value [rises/falls of a specific magnitude or rate] at specific times which correlate to observed problems at future times when it would be less convenient to test (e.g. overnight).

Tailoring—Prompt for readings at appropriate times to establish presence of predictive pattern, and if readings detect the pattern act more aggressively to detect or prevent the future problem (e.g. suggest immediate preventative action or schedule prompts during anticipated problem period).

In another embodiment of this invention the results of CGM testing may be used to tailor a maintenance SMBG test schedule. A maintenance SMBG test schedule is used at times when data is not being is not being collected to help diagnose the state of a patient's diabetes, rather it is used to ensure that the patient is maintaining good control when other more comprehensive monitoring is not taking place. The results of CGM testing may identify a few specific times of day of high low range variability or excessive hypoglycemia risk. In this case the maintenance schedule can be tailored for testing at those specific times of day.

Figure 20:
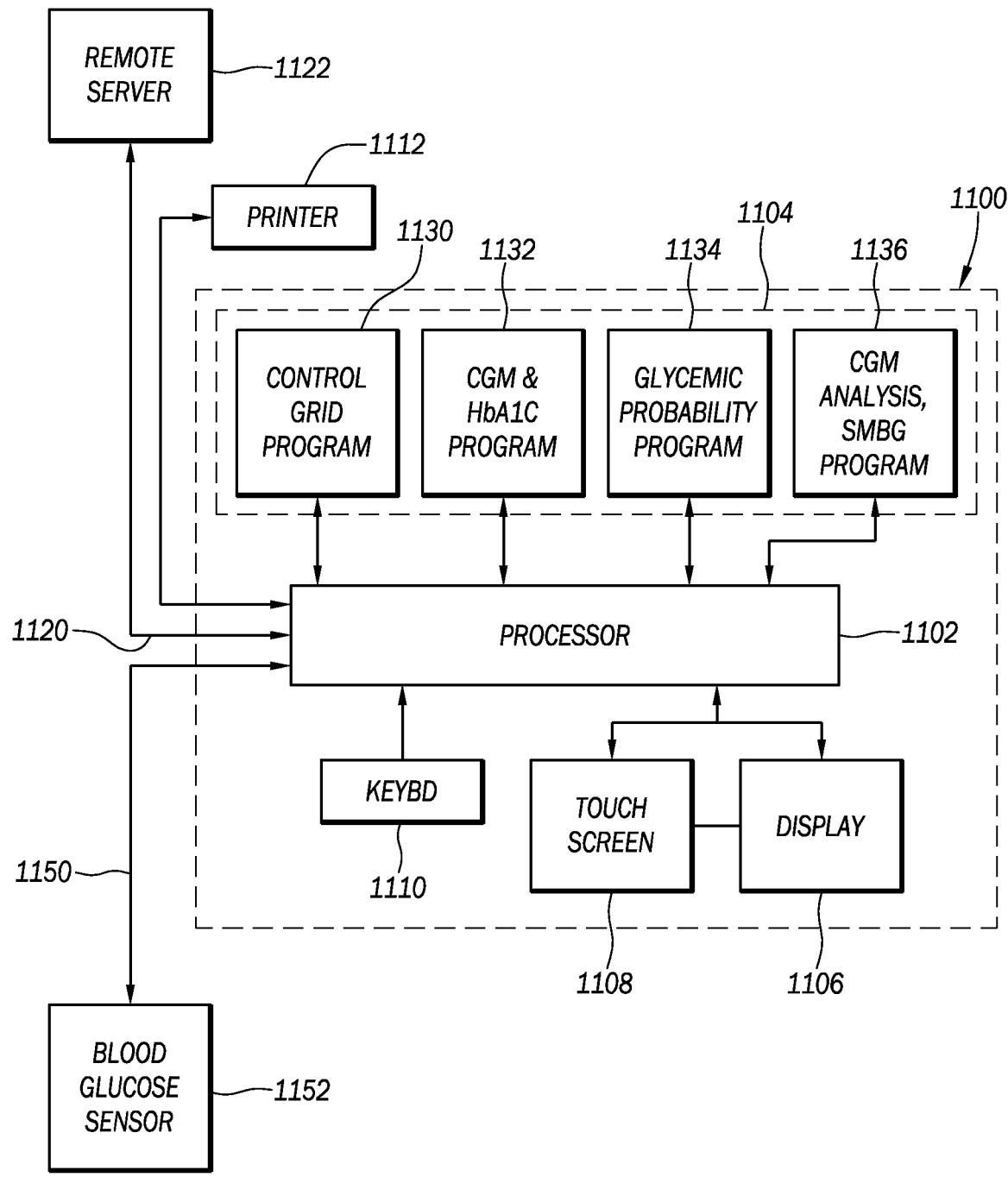
FIG. 20 is a block diagram of an embodiment of a system and method for carrying out the invention.

FIG. 20 is a block diagram of an embodiment of a system and method 1100 for carrying out the invention. This embodiment includes a processor 1102 housed in a mobile or stationary device at the patient site, a non-volatile memory 1104 for storing a program or programs used to program the processor, a visual display 1106 for visual output, the display having in this embodiment a touch-screen 1108 for input, and a keyboard input device 1110 of other type of device usable to manual entry, such as a keypad. The system 1100 is connected to a printer 1112 as an output or display device, and has a data output 1120 for communicating to a remote server 1122. In one embodiment, the remote server stores in a memory a patient's data for remote access by an HCP. In an embodiment, the processing of data is performed in the patient processor, or may be performed at the remote server.

The memory 1104 includes, in this embodiment, the Control Grid Program 1130 for calculation and visualization of glycemic risks, the CGM and HbA1c program 1132 for producing improved estimates of average glucose, the Glycemic Probability program 1134 for estimating glycemic risk, and the CGM Analysis and SMBG schedule tailoring program 1136, all of which are described above in detail. Other programs and data bases may be stored in the non-volatile memory. In another embodiment, one or more of the programs may be stored elsewhere but may be executed in the processor 1102. Other arrangements are possible and other hardware variations to carry out the invention are possible.

Blood glucose data 1150 is provided by a blood glucose sensor 1152. The BG sensor 1152 may take the form of a continuous glucose monitor (CGM) or may take other forms such as a strip reader, or other.

Design Description of Advanced Daily Patterns Report, Ambulatory Glucose Profile, Glucose Control Measure, Engine Module Introduction and Background A continuous glucose ("CG") analysis methodology is described for generating diabetes therapy decision guidance using continuous glucose data. The CG methodology disclosed herein, which exploits the relationship between glucose median, glucose variability, and hypoglycemia risk, is mathematically based and can be implemented in computer software. Using the reports generated from this analysis, the diabetes clinicians can quickly understand the patient's overall glycemic condition and review results designed to facilitate safe and effective therapy modifications, such as medication adjustments and self-care behavior modification.

Reference

Kovatchev, Boris et al., "Assessment of Risk for Severe Hypoglycemia Among Adults With DDM: Validation of the Low Blood Glucose Index." Diabetes Care 1998, 21, pp 1870-1875, hereby incorporated by reference.

AGP/CG Analysis Report Description

Figure 21:
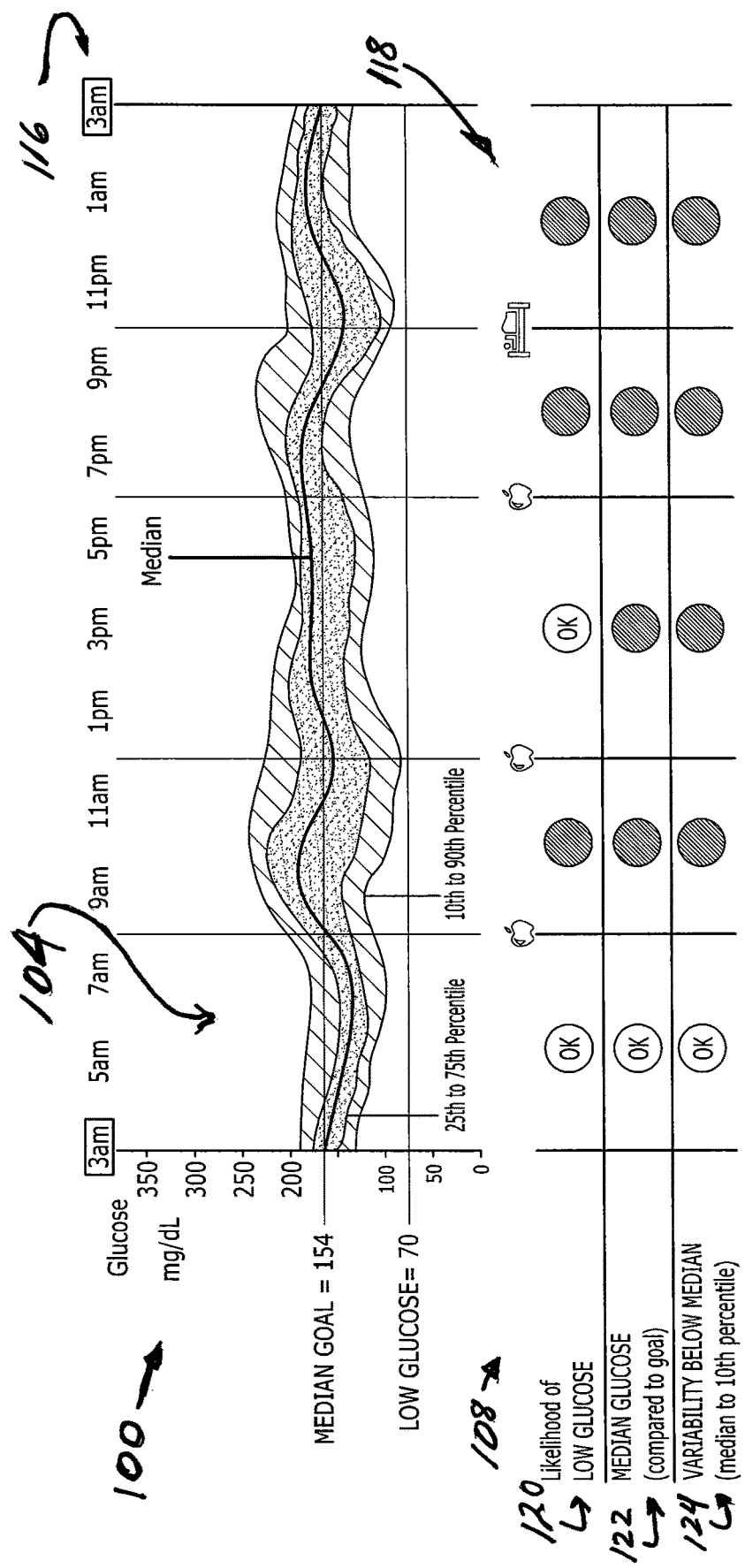
FIG. 21 shows an Advanced Daily Patterns (ADP) report covering the time frame of Nov. 10, 2012 through Nov. 23, 2012 (14 days) with a low glucose allowance setting of "Medium" with a median goal setting of 154 mg/dL (A1c equivalent of 7.0%, or 53 mmol/mol)
Figure 22:
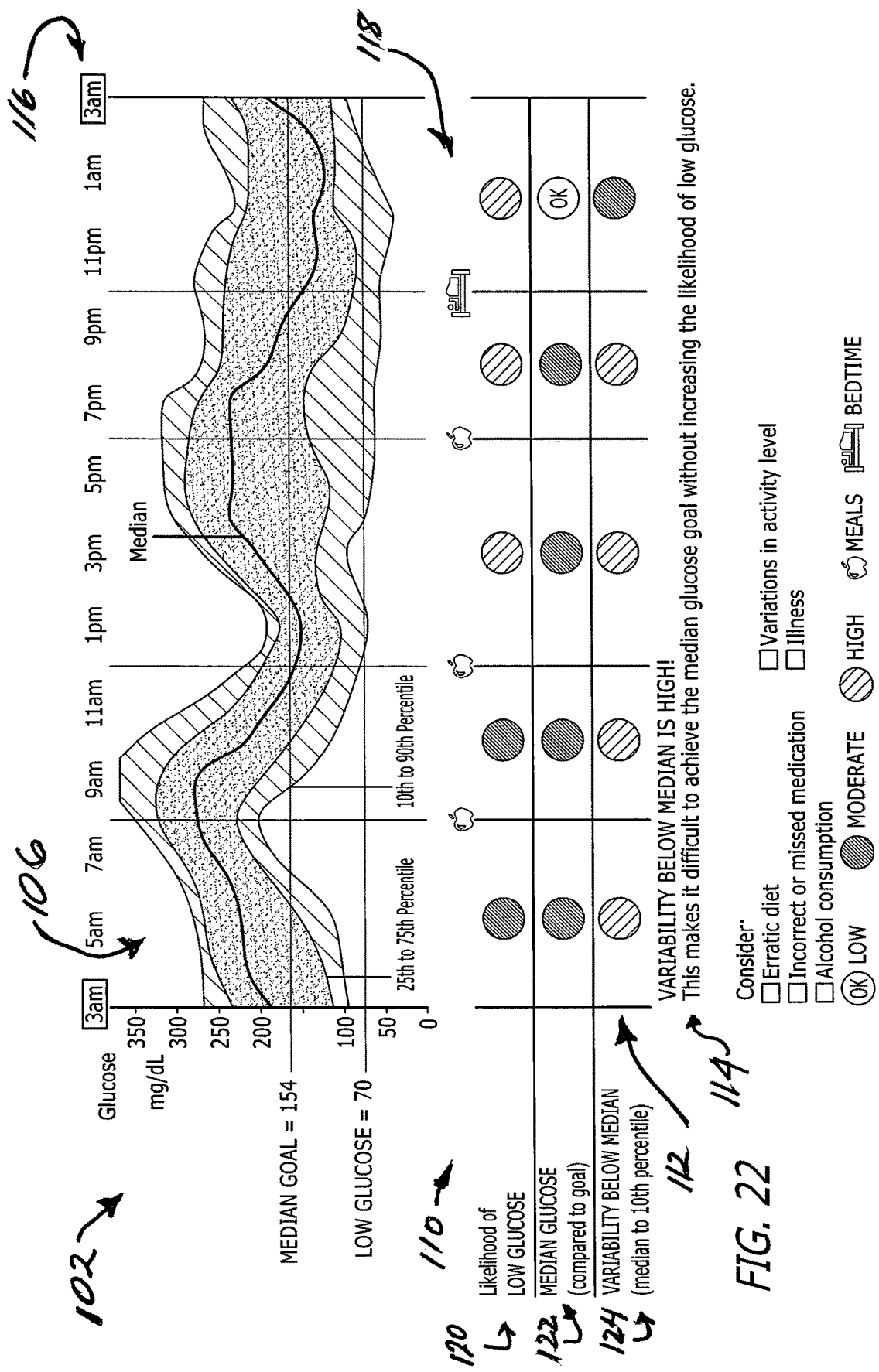
FIG. 22 shows an Advanced Daily Patterns (ADP) report covering the time frame of Nov. 10, 2012 through Nov. 23, 2012 (14 days) with a low glucose allowance setting of "High" with a median goal setting of 154 mg/dL (A1c equivalent of 7.0%, or 53 mmol/mol)

A particular report entitled the "Advanced Daily Patterns" (ADP) report, is generated from continuous glucose ("CG") data for a particular patient over a specified time period. Two examples of this report 100 and 102 are illustrated in FIGS. 21 and 22 respectively, each for different type 1 ("T1") diabetes patients with the same A1c (7.7%). Though these patients have the same A1c, the second one (FIG. 22) has much higher glucose variability, which can be seen in the "Ambulatory Glucose Profile" (AGP) plot 106 at the top of the report. The AGP shows a wider spread in the glucose data for the second patient (first patient is 104, FIG. 21). The "Glucose Control Measure" (GCM) table at the bottom of the report 108, 110 shows red "traffic lights" in the "VARIABILITY BELOW MEDIAN" row of the table 112 for the second patient. In the drawings, the red color is indicated by wide cross-hatching, yellow color indicated by narrow cross-hatching, and green colored traffic lights by an "OK" within a circle. The AGP 106 and GCM 112 also highlight that the second patient has a much higher risk of hypoglycemia than for the first; the AGP has glucose traces that extend down below 70 mg/dL, and the GCM shows red "traffic lights" in the "Likelihood of LOW GLUCOSE" row. This report emphasizes the relationship between median, glucose variability, and hypoglycemia risk.

The ADP report 100 is made up of three primary components: an Ambulatory Glucose Profile (AGP) plot 104, a Glucose Control Measure (GCM) table 108, and indications when high glucose variability is detected 114. These components are divided into Time-of-Day periods 116 that are relevant to people with diabetes.

The AGP 104 is a graph of the 10th, 25th, 50th (median), 75th, and 90th percentiles of glucose readings, presented over the "typical" day 116 based on all days within the selected timeframe. Below the AGP is a table containing three Glucose Control Measures 110 for each of five time periods 118 in the "typical" day.

Likelihood of Low Glucose 120 is the probability that low glucose values have exceeded an allowable, user-defined threshold.

Median Glucose 122 is an indication of when the median glucose has exceeded the Median Goal, which is also a user defined setting. Median glucose is strongly correlated to A1c.

Variability below median 124 is a measure of the spread of glucose data below the median. It is calculated as the difference between the 50th and 10th percentile glucose readings for the time period.

Figure 23:
FIG. 23 is an assessment by the Advanced Daily Patterns report of Glucose Control Measures as Low, Moderate, and High showing criteria used.

The Advanced Daily Patterns report 104 in FIG. 23 assesses Glucose Control Measures as Low, Moderate, or High based on the criteria 126 shown in the figure.

The third key component of the Advanced Daily Patterns report 100 is the indication of high variability. In FIG. 21, variability is not high for any time period, so variability is not highlighted. In FIG. 1b, the time-of-day periods of high variability are highlighted.

The description 114 (FIG. 22) in the bottom right corner of the Assessment table 110 highlights the importance of the variability. When the variability is large enough, it is impossible to simultaneously satisfy the median goal and the hypoglycemia avoidance goal. Factors that could contribute to variability include erratic diet, incorrect or missed medication, alcohol consumption, variations in activity level, or illness.

The Advanced Daily Patterns report has the following configurable settings:

Daily Events define the Time-of-Day periods during the day used to analyze the Glucose Control Measures. The typical times for Breakfast, Lunch, Dinner, and Bedtime for a particular patient can be defined prior to the analysis. These times correspond to daily events that are clinically relevant to diabetes patients whose therapy is centered on eating and sleeping events. The overnight time between Bedtime and Breakfast is divided into two periods to break up the long fasting period. The methodology restricts these Time-of-Day Periods to a range of 3 to 8 hours, except that two overnight periods are each limited to 6 hours each.

Median Goal is a setting that defines the glucose value for which Median Glucose (compared to goal) is reported as Low, Moderate, or High. The following settings are possible:

| Goal | A1c equivalent |
| --- | --- |
| 126 mg/dL (7.0 mmol/L) | 6.0%, or 42 mmol/mol |
| 140 mg/dL (7.8 mmol/L) | 6.5%, or 48 mmol/mol |
| 154 mg/dL (8.6 mmol/L) | 7.0%, or 53 mmol/mol |
| 169 mg/dL (9.4 mmol/L) | 7.5%, or 58 mmol/mol |
| 183 mg/dL (10.2 mmol/L) | 8.0%, or 64 mmol/mol |
| 197 mg/dL (10.9 mmol/L) | 8.5%, or 69 mmol/mol |

Low Glucose Allowance is a setting that defines the threshold for which Likelihood of Low Glucose is reported as Low, Moderate, or High. The setting options are Small, Medium, or Large. Increasing this parameter increases the amount of allowable low glucose readings below 70 mg/dL (3.9 mmol/L). The allowance is based on both the frequency and value of low readings. These settings translate approximately to:

| | |
| --- | --- |
| Small | 2% of readings at 50 mg/dL (2.8 mmol/L), or 4% of readings at 60 mg/dL (3.3 mmol/L) |
| Medium | 4% of readings at 50 mg/dL (2.8 mmol/L), or 8% of readings at 60 mg/dL (3.3 mmol/L) |
| Large | 10% of readings at 50 mg/dL (2.8 mmol/L), or 20% of readings at 60 mg/dL (3.3 mmol/L) |

Decision Support Method Approach

For diabetes clinicians and patients, the glycemic management challenge is to balance two competing objectives: lowering overall glucose levels, while keeping these values above a low-glucose threshold, which is defined for this analysis to be 70 mg/dL. One key distinction of normal glucose levels is that the "spread" or "variability" of the glucose levels is low compared to persons with diabetes. When glucose variability is high, taking steps to generally lower glucose levels, perhaps with medications such as insulin, may cause more glucose levels to fall below 70 mg/dL. This suggests that in order to reduce overall glucose levels without causing more levels to fall below 70, it may be necessary in some situations to reduce glucose variability. Stated another way, to allow safe increase in glucose-lowering medications, it is often necessary to take steps to reduce glucose variability.

There are two important aspects that need to be considered for proper glycemic management—a) reducing overall glucose levels and b) reducing glucose variability. Clinicians address the former by prescribing medications, or suggesting diet and exercise, which are intended to reduce overall glucose levels. To address variability, clinicians often attempt to identify and address self-management behaviors or conditions that may be causing erratic swings in glucose levels; such behaviors or conditions include erratic diet, incorrect or missed medication, alcohol consumption, variations in activity level, or illness. Addressing self-management behaviors is a mechanism for reducing glucose variability.

Mathematical Framework

A mathematical framework can be used to describe the decision support methodology in a way that facilitates the development of rules that can be programmed in software. The key to this framework is to consider that each patient for a period of time has a population of glucose readings that can be modeled as a stationary distribution. As described in Appendix A, an appropriate standard distribution model for glucose measurements is the Gamma distribution. For each patient/period, this distribution can be characterized by a "central tendency" metric and a "variability" metric. For the methodology herein, the "median" was chosen as the metric for central tendency, and the difference between the median and 10th percentile was chosen as the metric for variability—herein, this measure of variability will be referred to as "South 40" or "S40" for short. Percentile metrics were favored over other common metrics such as mean and standard deviation because a) percentiles are more robust to outliers that often occur in glucose data, and b) commonality with AGP's use of percentiles. The S40 metric was chosen for representing variability over other "symmetric" measures, such as the interquartile range or the difference between the $90^{th}$ and $10^{th}$ percentiles, because the gamma distribution is an asymmetric distribution, and as shown in Appendix A, the Gamma distribution model more accurately represents glucose readings at low glucose values. Bias correction is necessary for estimation of these metrics for low sample sizes—this is described in Appendix B.

This framework can be used to describe the mathematical relationship between glucose median, glucose variability, and hypoglycemia risk. This relationship leads to rules that translate glucose data into standardized guidance for treatment decisions. The two glycemic management objectives are naturally represented by the glucose median, which has been shown to be correlated with A1c, and hypoglycemia risk. Glucose variability is a third metric that relates the two and must be addressed if both objectives are to be met. These rules can be programmed and are the basis for the AGP module calculations.

Definition of Hypo Risk

Before the relationship between median, variability, and hypoglycemia risk is described, "hypoglycemia" must be defined mathematically. For the purposes of this method, a hypoglycemia metric was selected that is dependent on both time and magnitude of glucose readings below the 70 mg/dL—this metric is referred to as AU70 (short for "area under 70 mg/dL"). The AU70 metric is defined as:

a) Sum of all differences (70 mg/dL—Reading) for all Readings below 70 mg/dL
b) Divided by number of all Readings This definition of hypoglycemia is used in the present methodology a) to calculate Hypo Risk Curves using the Gamma distribution model, and b) to evaluate how well these curves can be used to estimate hypoglycemia risk. The explanation and derivation for these curves is given later in this document.

The value of the AU70 metric used in generating the ADP report 100 is referred to as the "Low Glucose Allowance" (LGA) setting. As described previously, the present methodology has three possible settings defined for LGA; each of these configures the algorithm for three corresponding amounts of risk for low glucose.

Appendix C discusses other Hypo Risk metrics and why the AU70 metric was chosen for the present methodology.

Relationship Between Median, Variability, and Hypo Risk (Hypoglycemia Risk)

Figure 24:
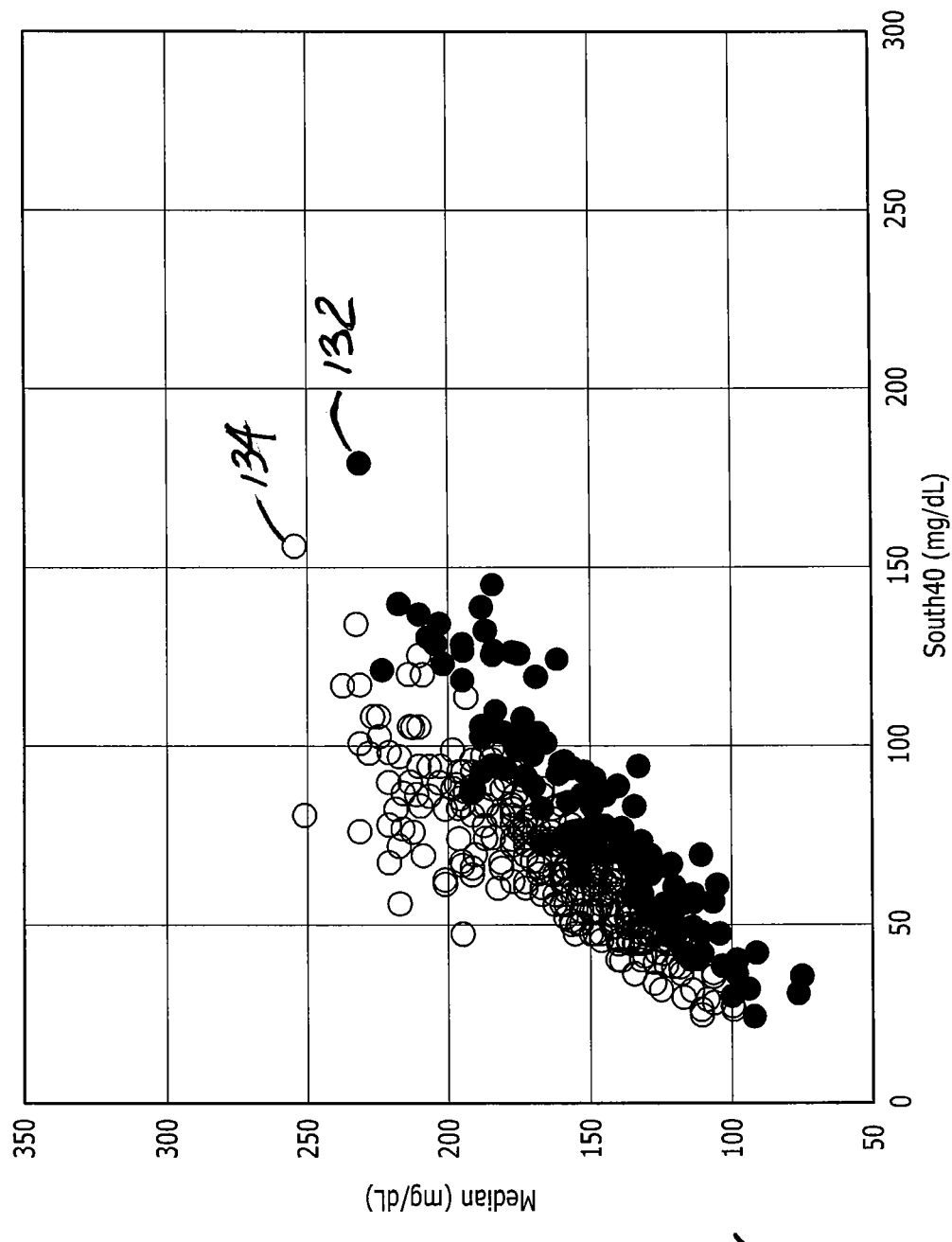
FIG. 24 shows median-variability points with excessive measured hypoglycemia in solid circles and acceptable measured hypoglycemia is open circles.
Figure 25A:
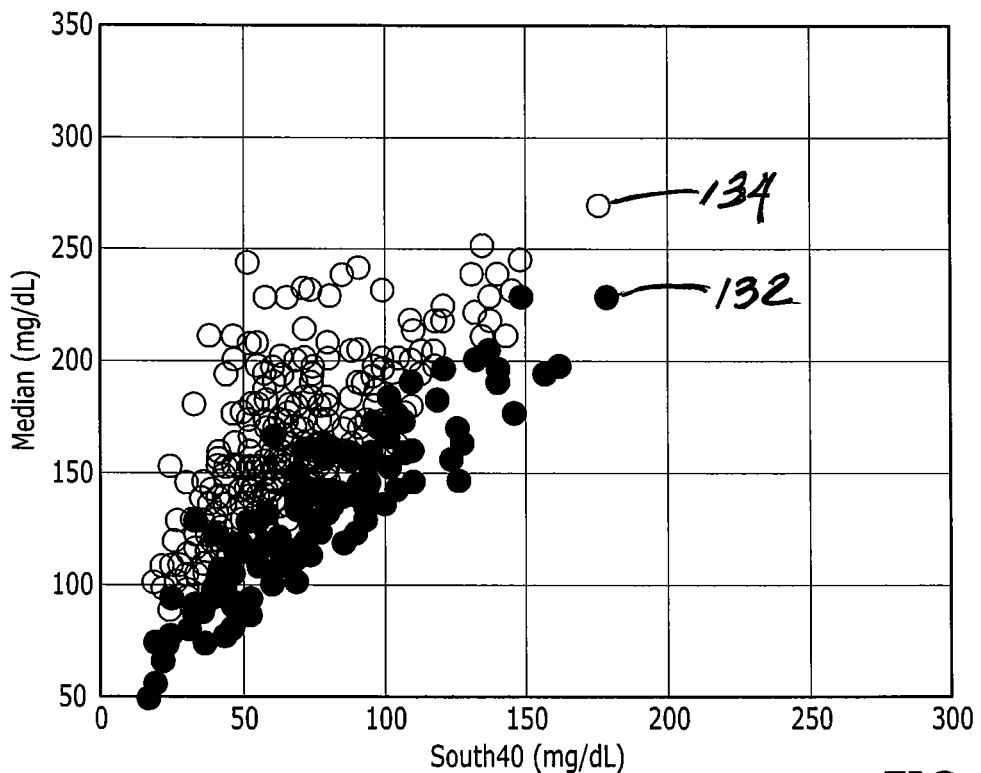
FIGS. 25A through 25E show a similar separation between median-variability points with excessive hypoglycemia (solid circles) and points with acceptable hypoglycemia (open circles), with 25A being calculated from pre-breakfast, 25B calculated from post-breakfast, 25C calculated from post-lunch, 25D calculated from post-dinner, and 25E calculated from post bedtime.
Figure 25B:
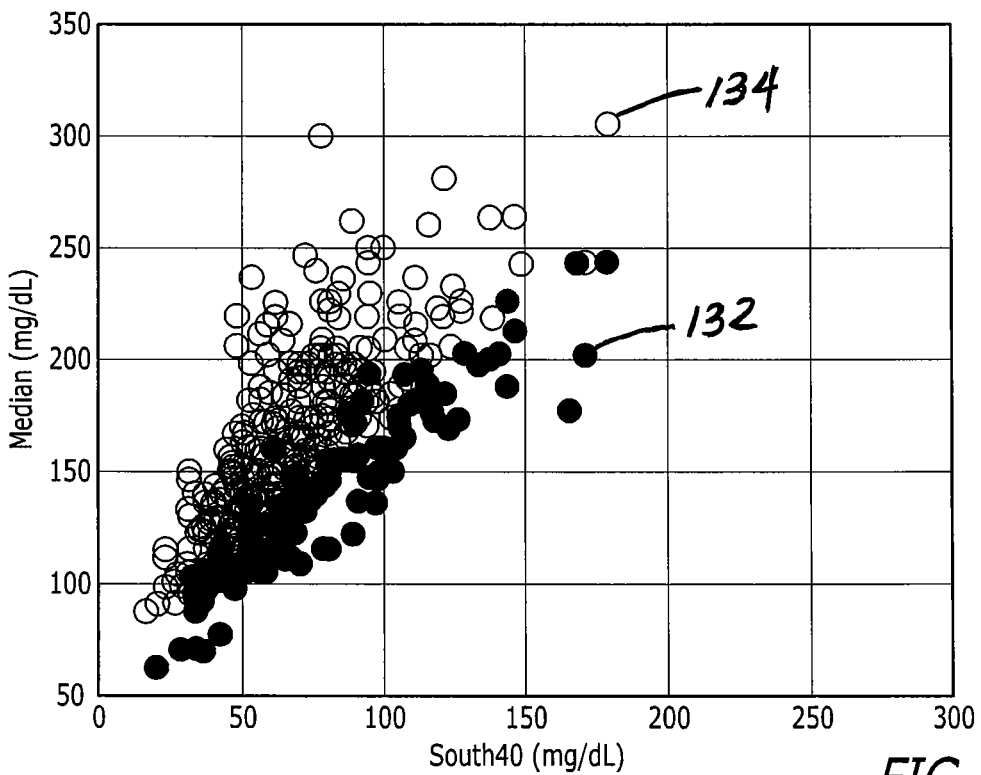
Figure 25C:
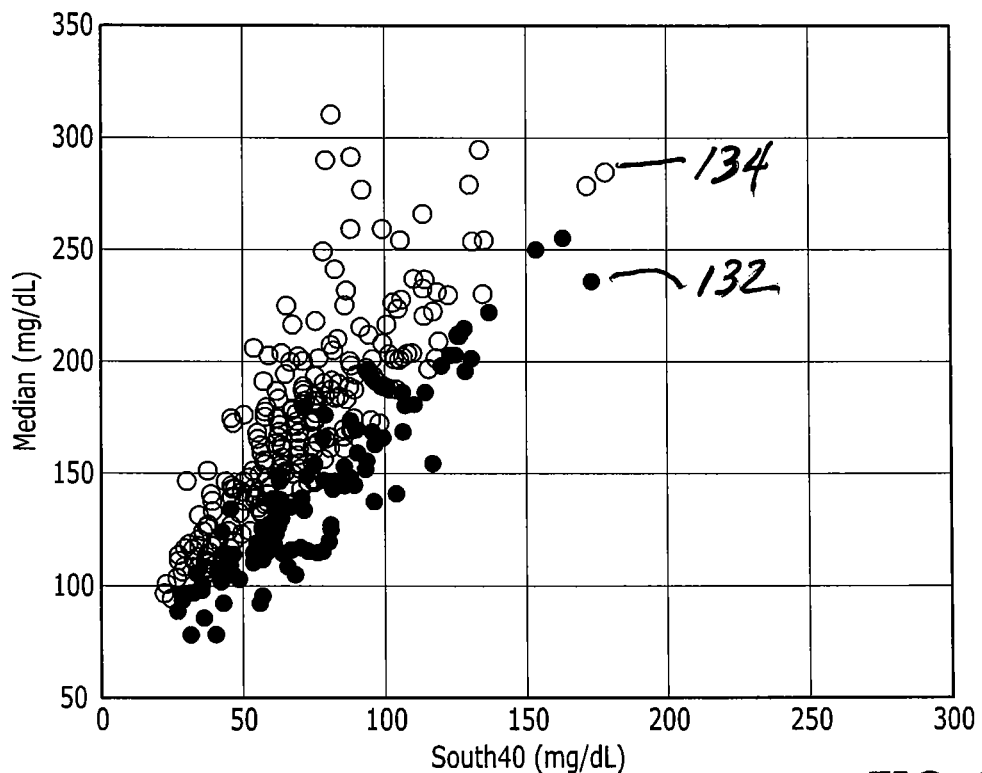
Figure 25D:
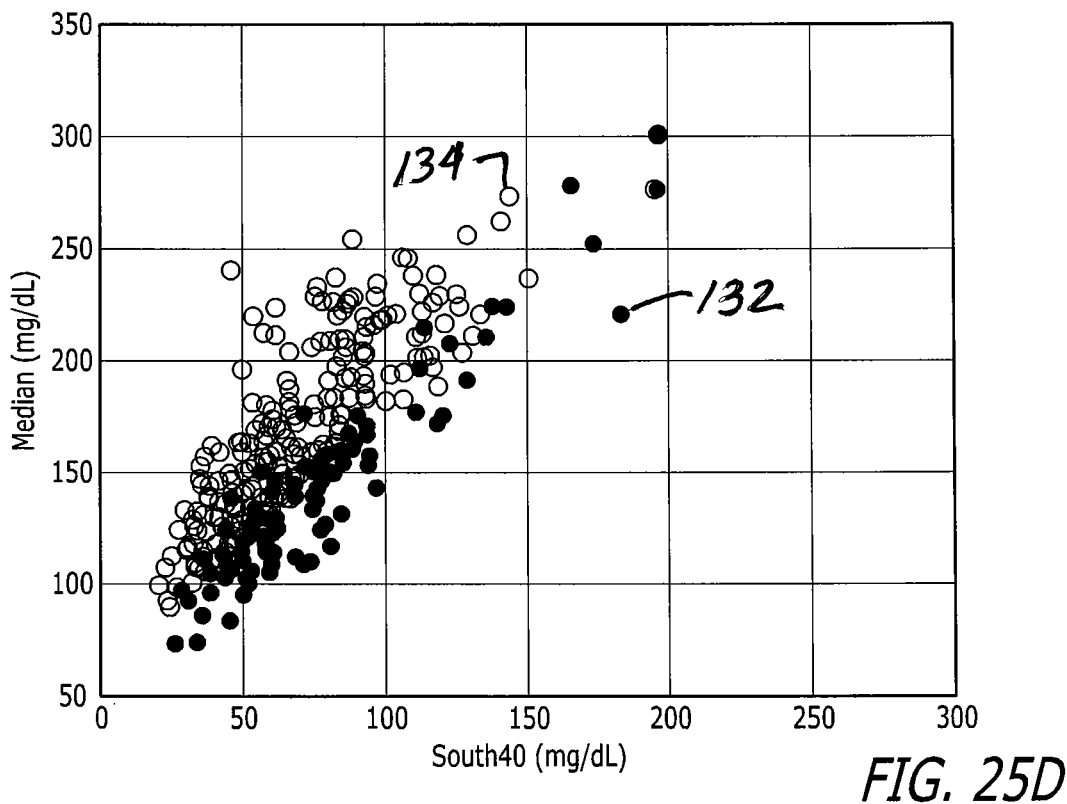
Figure 25E:
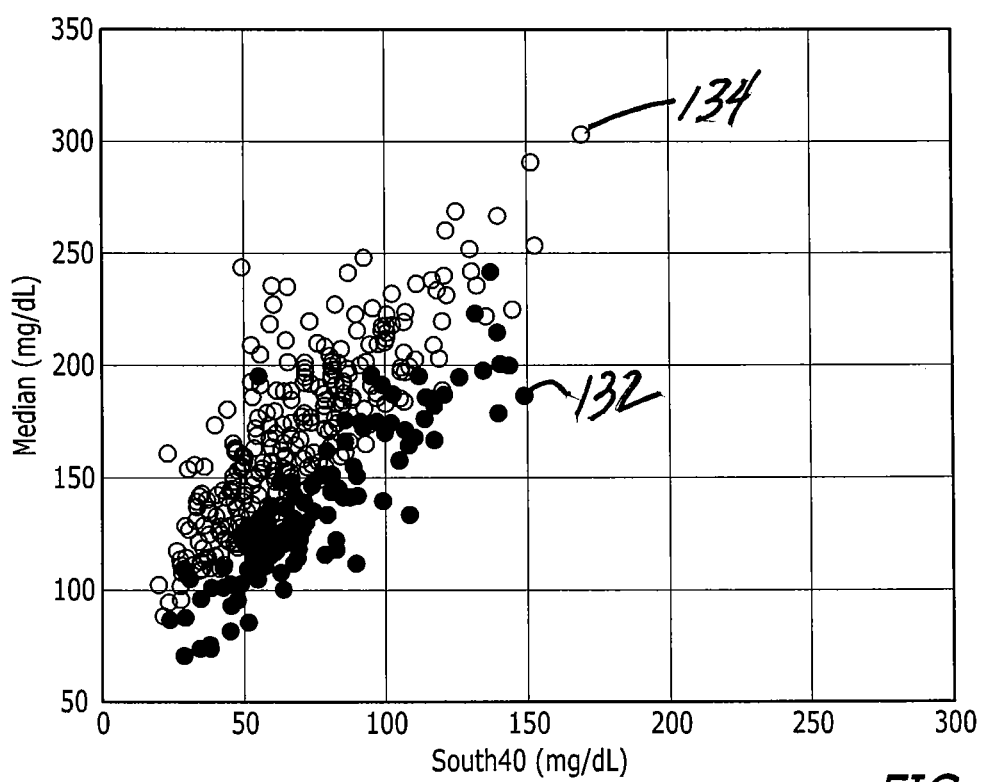

The key to the decision support methodology is the observation of the important relationship between median, variability, and hypoglycemia risk, as illustrated on the median-variability plot 130 shown in FIG. 24. Data from the first two weeks of the Juvenile Diabetes Research Foundation ("JDRF") study was used to make FIGS. 24, 25A-E, and 26A-C.

In FIG. 24, with the glucose median on the y-axis and the glucose variability (or S40) on the x-axis, a point is plotted for each patient/period, where the period defines the range of continuous glucose data over multiple days. The point is a closed circle 132 if the hypoglycemia risk metric calculated using the patient/period data exceeds the Low Glucose Allowance at the medium setting; otherwise, the point is an open circle 134. The plot 130 in the figure suggests that two zones could be defined: one associated with excessive hypoglycemia and one associated with acceptable or no hypoglycemia, indicating that the combination of median and variability may be a good predictor of hypoglycemia risk—it will be shown below how this observation is used to design a decision support methodology.

It is important to note that the median-variability-hypo risk relationship not only holds for glucose data representing an entire 24-hour time-of-day. It is also relevant when the glucose data are segmented into different time-of-day periods. The remaining derivations assume that the glucose data are segmented into five time-of-day periods that are relevant to diabetes patients—Pre-breakfast (default 3 am-8 am), Post-breakfast (default 8 am-12 pm), Post-lunch (default 12 pm-6 pm), Post-dinner (default 6 pm-10 pm), Post-bedtime (default 10 pm-3 am). The glucose data used to generate the median-variability plot in FIG. 24 was segmented into these time-of-day periods and a similar median-variability plot was generated for each of these, respectively, in FIGS. 25A through 25E. These figures show a similar separation between median-variability points with excessive hypoglycemia and points with acceptable hypoglycemia.

In particular, FIGS. 25A through 25E show Median-variability points with excessive measured hypoglycemia in solid circles 132 and acceptable measured hypoglycemia in open circles 134. The points on each plot are calculated from glucose data segmented by the Pre-breakfast (FIG. 25A), Post-breakfast (FIG. 25B), Post-lunch (FIG. 25C), Post-Dinner (FIG. 25D), Post-bedtime (FIG. 25E) time-of-day periods, respectively.

Definition of Hypo Risk Curve

The results shown in FIGS. 24 and 25A-25E suggest that the median-variability plot can be separated into two zones: a "high hypoglycemia risk" zone and a "low hypoglycemia risk" zone. The Gamma distribution model of the glucose data can be exploited along with the AU70 definition of hypoglycemia to define the curve that separates these zones. The mathematical derivation of this curve (referred to as the "Hypo Risk Curve") is described in Appendix D. Three Hypo Risk Curves, one for each Low Glucose Allowance setting, are predetermined for each of the five time-of-day periods.

Figure 26A:
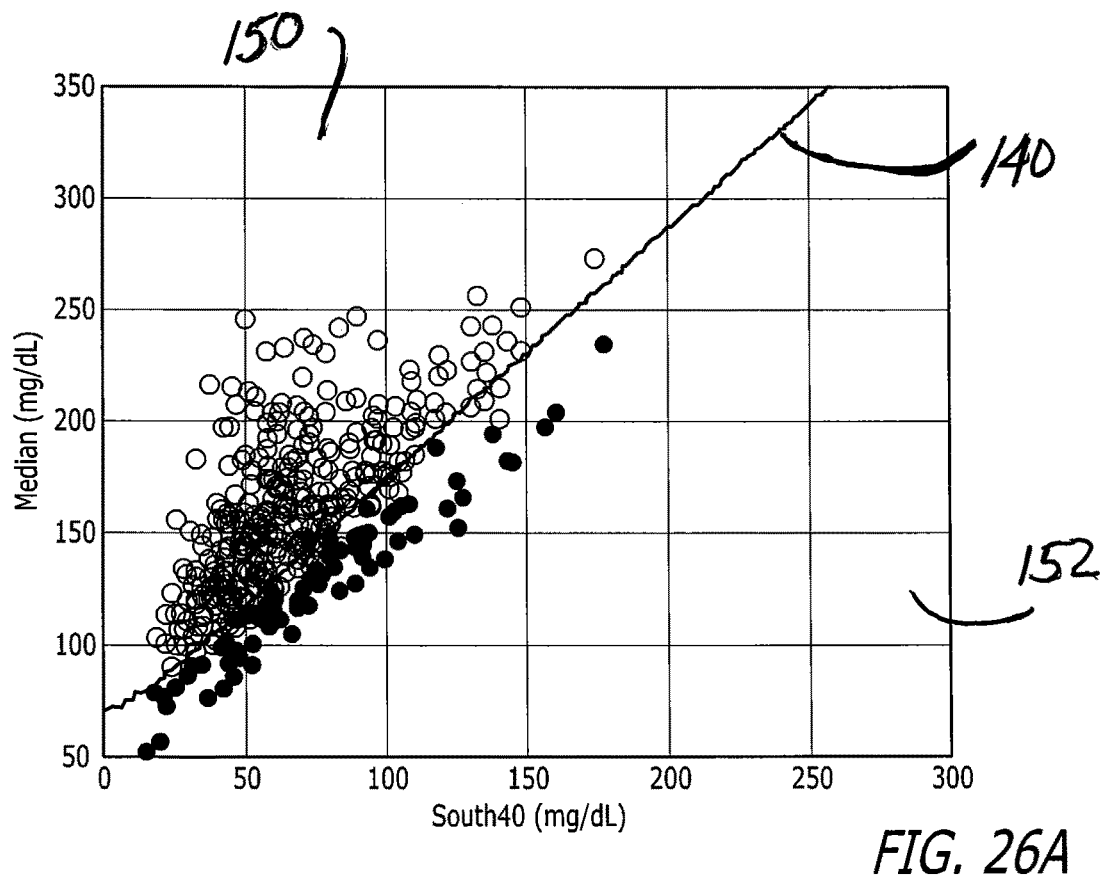
FIGS. 26A through 26C show hypo-risk performance where 26A shows pre-breakfast with a large LGA ((low glucose allowance), FIG. 25B shows pre-breakfast with a medium LGA, and 26C shows pre-breakfast with a small LGA.
Figure 26B:
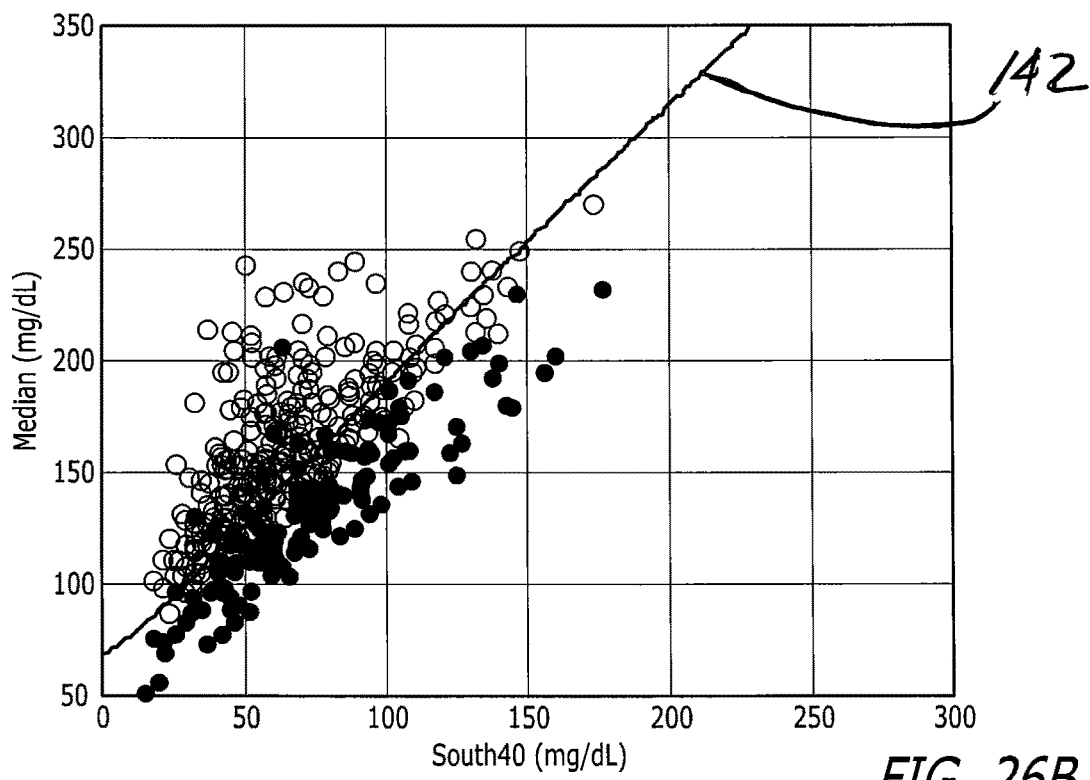
Figure 26C:
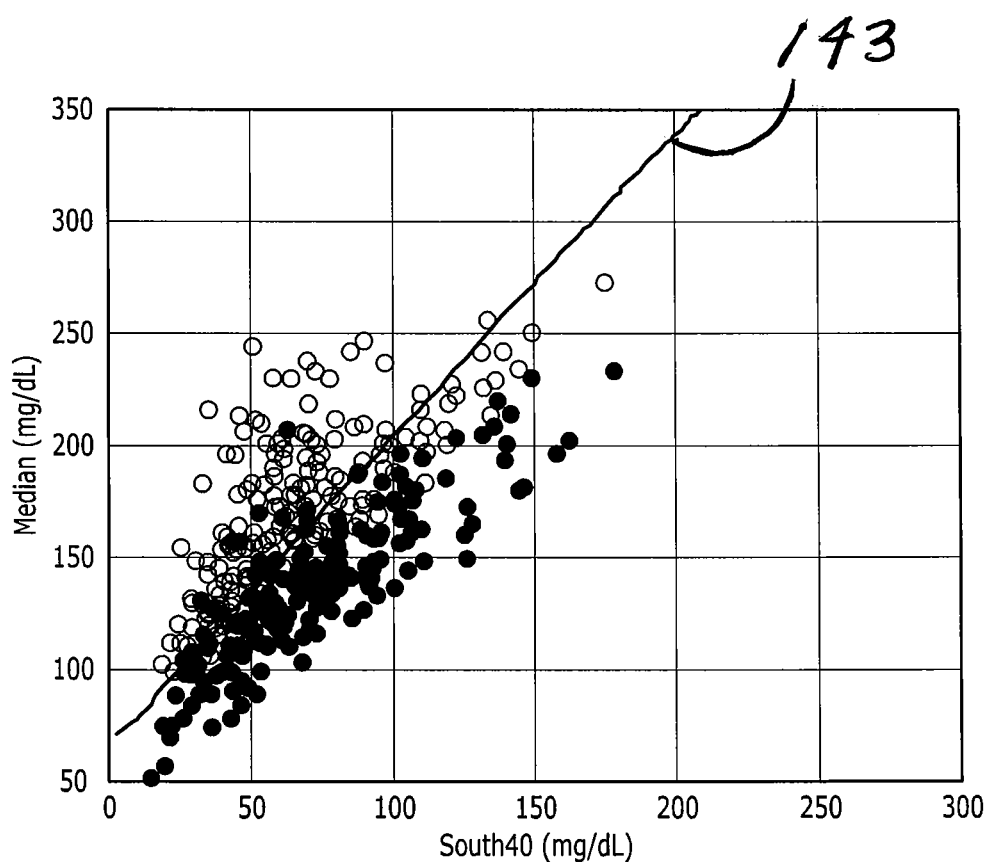

In FIGS. 26A to 26C, the mathematically derived Hypo Risk Curve for the three different Low Glucose Allowance settings 140, 142, 144 is shown overlaying the median-variability points of FIGS. 25A through 25E for the Pre-breakfast period. These figures illustrate that the theoretical curve based on the Gamma model is in good agreement with calculated AU70 result for each patient/period point.

In particular, in FIG. 26A, the hypo risk performance is shown for pre-breakfast with an LGA=large. In FIG. 26B, the hypo risk performance is shown for pre-breakfast, with an LGA=medium. In FIG. 26C, the hypo risk performance is shown for pre-breakfast with an LGA=small.

The detection performance of the Hypo Risk Curve is described in Appendix D; for the Medium LGA setting, the sensitivity ranges from 88% to 92%, and the specificity ranges from 77% to 89%, across the five time-of-day periods.

As a side note, another reason that the S40 metric was chosen to represent glucose variability is that it is a better detector of hypoglycemia than more commonly used symmetric variability metrics such as the interquartile range ("IQR"), as shown in Appendix E.

Low Glucose Allowance Setting Rationale

Determining the appropriate value for the Low Glucose Allowance setting is a challenge because there are there are currently no clinical guidelines for what this setting should be. The effect of the Low Glucose Allowance setting, in terms of insulin treatment, is such that the "small" setting would correspond to less hypoglycemia tolerated, potentially resulting in conservative insulin therapy, while the "large" setting would correspond to more hypoglycemia tolerated, potentially resulting in aggressive insulin therapy. Note that zero risk is not possible, nor is it practical. In the absence of clinical guidelines, the present methodology is designed to allow the clinician to select from one of three possible values. The rationale for these three values for the Low Glucose Allowance setting is described in Appendix F. In Appendix G, the reasonableness of these three values is evaluated.

Definition of the Control Grid

FIGS. 26A through 26C showed that the median-variability plot can be divided into two "zones" separated by a hypo risk curve; the upper zone is the "low hypo risk" zone (150, FIG. 26A), and the lower zone is the "high hypo risk" zone (152, FIG. 26A). This concept of zones can be extended to convert the median-variability plot into a so-called "Control Grid." For a set of CG data for a patient, a point on the Control Grid can be calculated for each of the five time-of-day periods.

Figure 27:
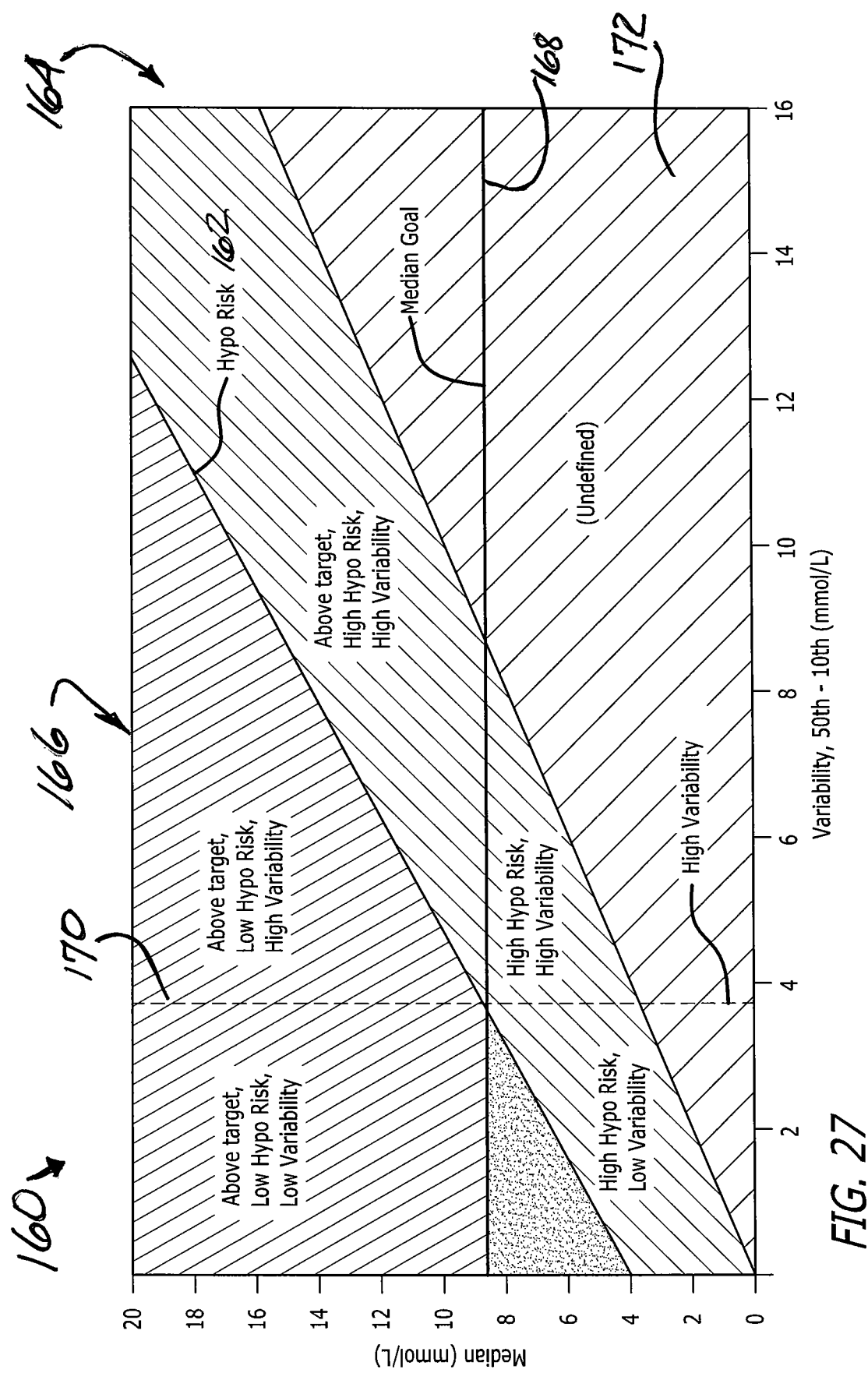
FIG. 27 shows the development of a control grid with six zones shown, in accordance with aspects of the invention.

The development of the Control Grid 160 is shown in FIG. 27 where six zones are shown. The Hypo Risk curve 162 divides the median-variability plot 160 into a "high hypo risk" zone 164 (below the curve 162) and the "low hypo risk" zone 166 (above the curve 162), as described above. A horizontal line, called the "Median Goal" 168 is added. The median goal is a useful therapy target because the median is strongly correlated with the patient's A1c—median glucose can be used to represent overall glucose when attempting to reduce all glucose levels.

A vertical line 170 is added at the intersection of the median goal line and the hypo risk curve—this line separates high variability from low variability. The clinical relevance of high variability is that it is, by definition, a degree of variability in which the median cannot be reduced below the median goal without causing high hypoglycemia risk. In FIG. 27, six different zones are now identified according to glycemic conditions of clinical relevance that are suggestive of the direction of therapy modification. The gray area 172 at the lower right is not possible, and therefore does not count as a zone. The significance for therapy decision support is that the zones provided on the control grid can be the basis for mapping glucose data for a patient/period into therapy suggestions.

The concept of zones can be further extended to allow for "moderate" zones where the patient/period results are close to zone demarcations. The "final" Control Grid 176 is shown in FIG. 28A, which includes these moderate zones.

Figure 28A:
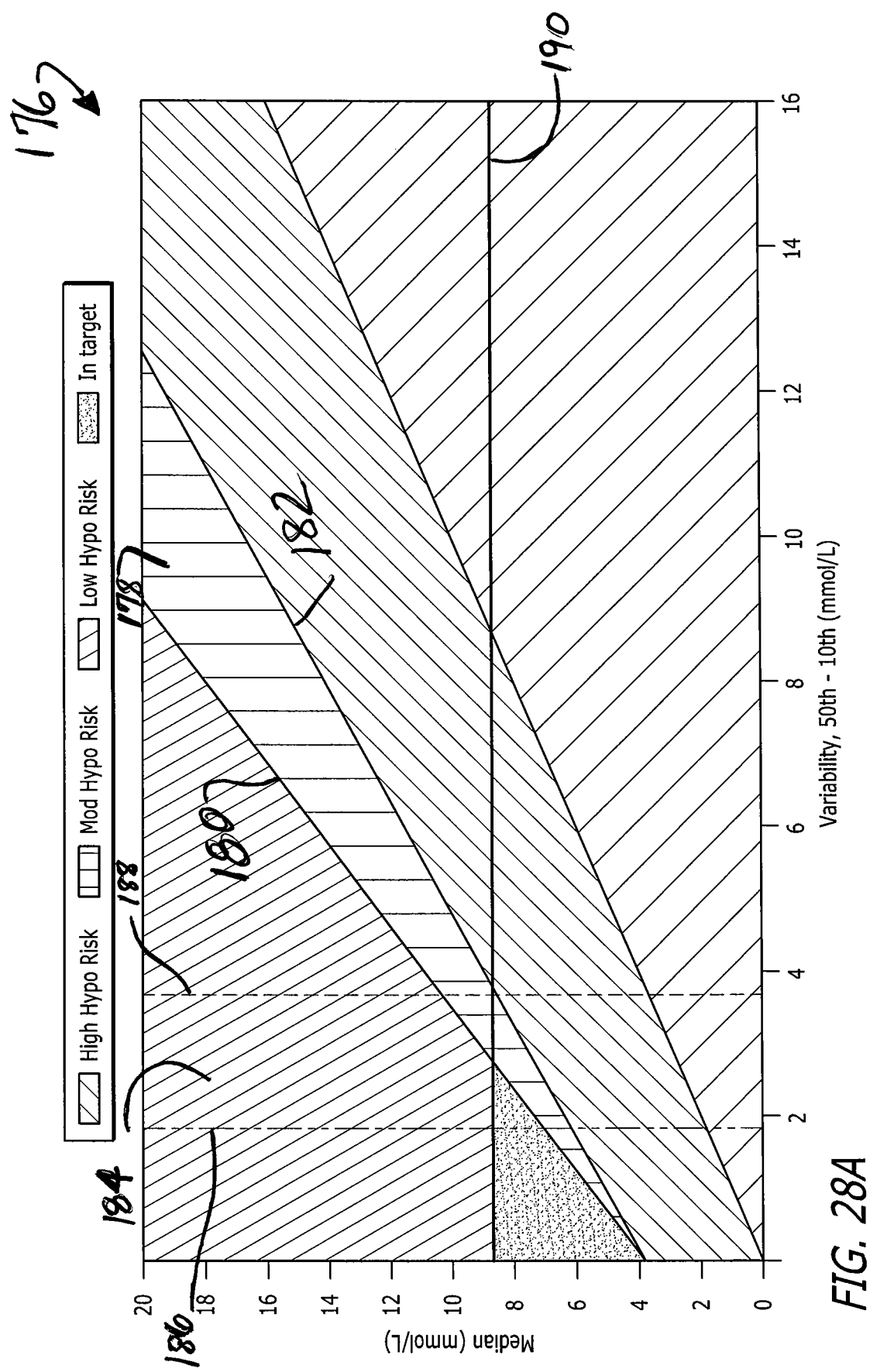

FIG. 28A, The Control Grid 176

A "moderate hypo risk" zone 178 is provided that allows for uncertainty in the Hypo Risk assessment due to a) uncertainty in the median and S40 estimates, as a function of data sample size, and b) variation in a typical patient's median and variability that will naturally occur over time. The moderate hypo risk zone, shown in wide cross-hatching in FIG. 28A is bounded above by the Moderate Risk Curve 180 and below by the Hypo Risk Curve 182. The derivation of the Moderate Risk Curves is provided in Appendix H.

As used in the black and white drawings accompanying this application, the color red is shown as wide cross-hatching, the color yellow is shown as narrow cross-hatching, and the color green is shown as the letters "OK" in a circle.

The moderate variability zone 184 is provided on the Control Grid, shown in FIG. 28A bounded on the left by the vertical line 186 (dashed) representing moderate variability, and on the right by the high variability vertical line 188 (dashed). The moderate variability line is defined at S40=35 mg/dL (1.9 mmol/L); this value was determined by observing that non-diabetic people are generally below this level of variability, as can be seen in Appendix C, FIG. 38.

The moderate-to-high median demarcation is not shown explicitly in the Control Grid 176. When a Control Grid point falls above the Median Goal line 190, it is considered either Moderate or High with respect to the Median Goal. The present methodology defines a time-of-day period to be High with respect to the Median Goal when the Control Grid point is more than 20% and 40 mg/dL greater than the whole-day median. The intent is to only draw attention to above-goal time-of-day periods with a High Median indication if it is substantially higher than the other time-of-day period medians.

Derivation of the Glucose Control Measures Table FIG. 28B

A point on the Control Grid 176 (FIG. 28A) can be determined based on any population of glucose data. For the present methodology, five control grids are used, each one representing data associated with a specific time-of-day. The column of results in the Glucose Control Measure table 194, FIG. 28B, are generated by a corresponding Control Grid—each column represents a time-of-day period, and the data from this time-of-day period is used to calculate the point on the corresponding Control Grid.

The logic used to map each Control Grid 176 point to each column of the Glucose Control Measures table 194 is as follows:

Likelihood of Low Glucose:
   Green (OK) if above the Moderate Hypo Risk curve
   Yellow (narrow cross-hatching) if between the Moderate Hypo Risk curve and the High Hypo Risk curve
   Red (broad cross-hatching) if below the High Hypo Risk Curve Median Glucose:
   Green (OK) if below the Median Goal line
   Yellow or Red if above the Median Goal line
   Red if above the Median Goal line AND more than 20% and 40 mg/dL (2.2 mmol/L) greater than the whole-day median Variability Below Median:
   Green (OK) if below the Low Variability line
   Yellow if between the Low Variability line and the High Variability line
   Red if above the High Variability line
How to Interpret the Glucose Control Measure Table
The value of the GCM table is that it directly maps to potential therapy adjustments. The table below illustrates this mapping in terms of therapy for insulin using patients.
Data Sufficiency
The median and S40 estimates become less representative of the patient's true glucose profile as the number of readings is reduced. The rules defining the minimum number of readings required to calculate a valid median and S40 estimate for each TOD period is a trade-off between achieving a high degree of certainty in the estimate and being tolerant of missing readings.

The rules that define the minimum amount of data needed to generate a median and South40 estimate for any TOD period are:
   a) At least ten total glucose readings in the TOD period; and
   b) Readings from at least five distinct days in the TOD period.

Ten readings per TOD period allow the S40 (that is, $10^{th}$ percentile) to be meaningfully distinguished.

Figure 29:
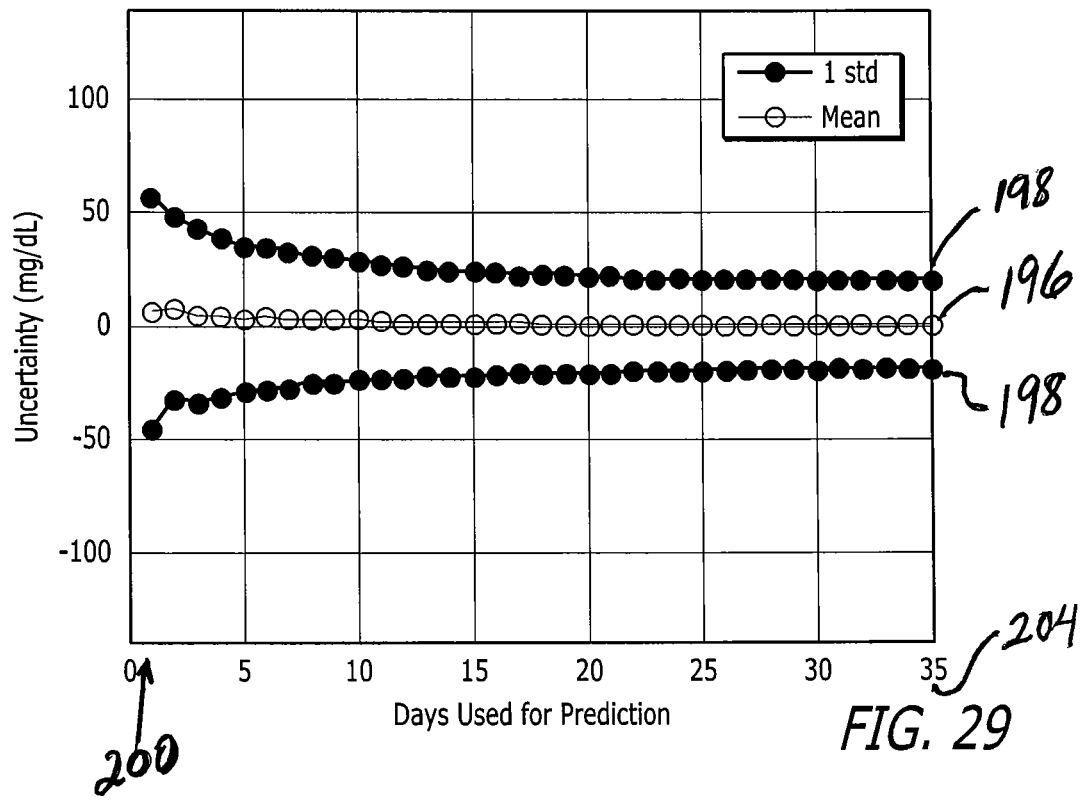
FIG. 29 presents median uncertainty vs. days used for prediction.
Figure 30:
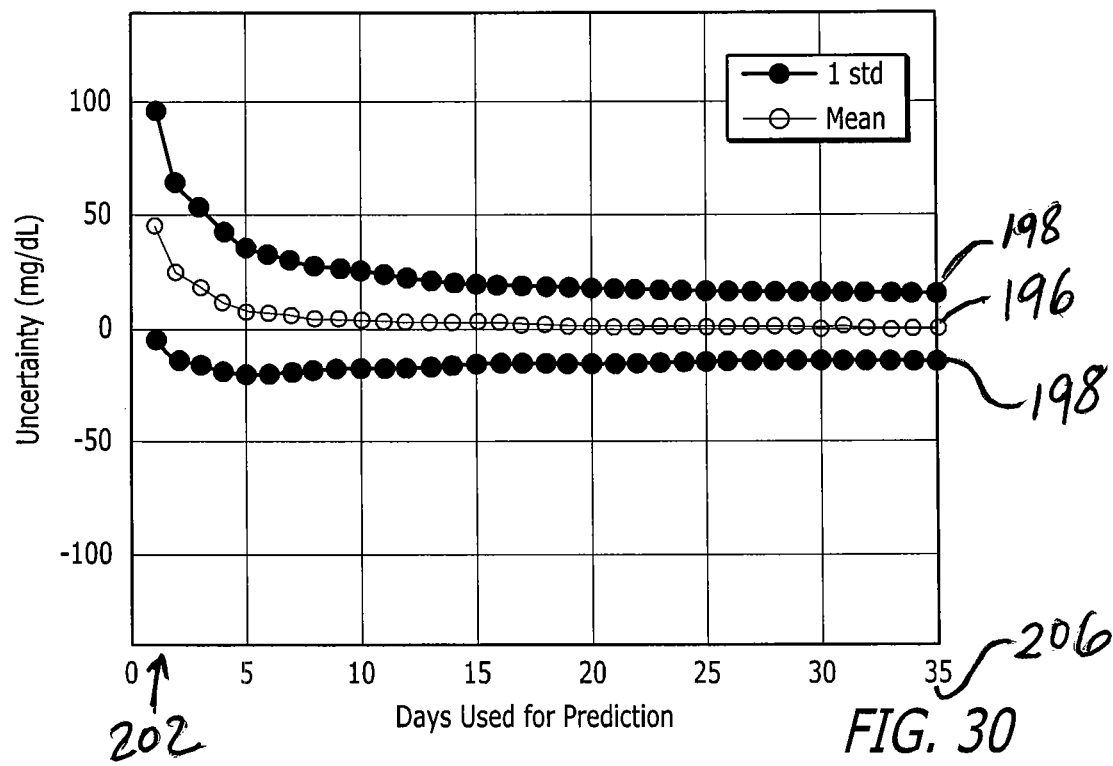
FIG. 30 presents tenth percentile uncertainty vs. days used for prediction.
Figure 31A:
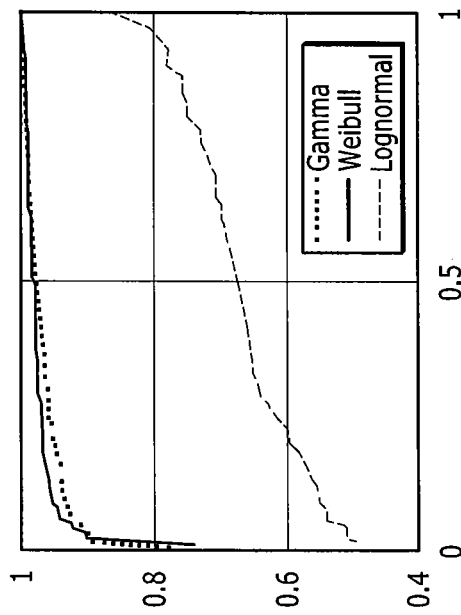
FIGS. 31A, 31B, 31C, and 31D show four categories according to whether the data was masked or not and what time of day the data was taken, with FIGS. 31A and 31C taken at daytime and FIGS. 31B and 31D taken at nighttime and with FIGS. 31A and 31B being masked data, and FIGS. 31C and 31D being unmasked data.
Figure 31B:
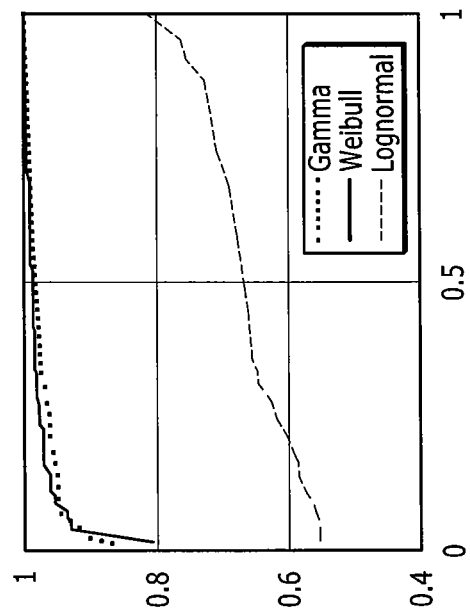
Figure 31C:
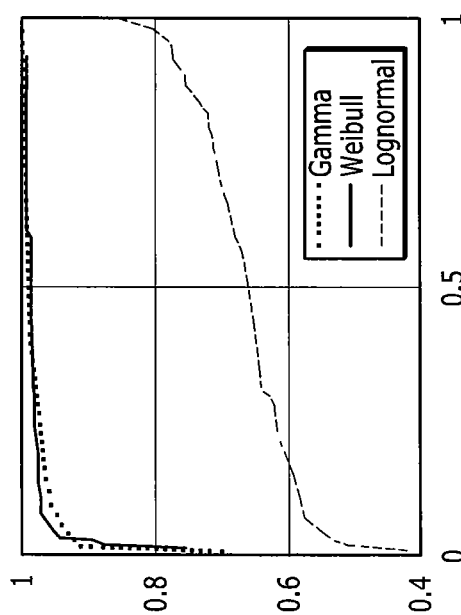
Figure 31D:
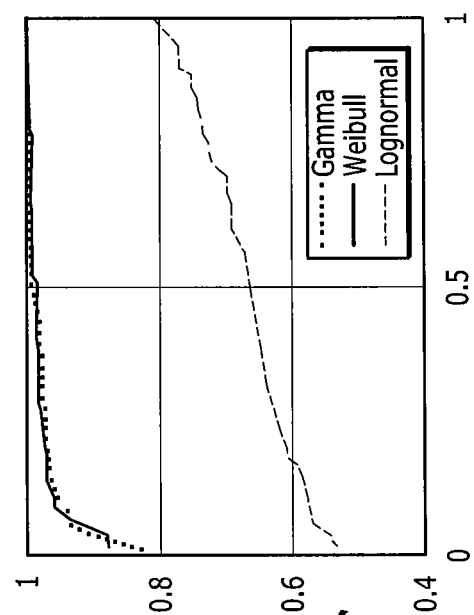

To justify the five-day limit, the predictability of the median and the 10th percentile are examined for varying days of availability. Using the Navigator CGM data from JDRF study, each of the 54 subject's glucose data were sliced into 35-day segments and the median and 10th percentile were calculated. These values were known as "truth." From the segment preceding the truth, various numbers of days were used to estimate the median glucose and the 10th percentile. These values were called "predictions." FIG. 29 shows how the median uncertainty increases as the number of days of glucose readings is reduced. Likewise, FIG. 30 shows the 10.sup.th percentile uncertainty increase. In both plots, estimates for all TOD periods and all subjects have been combined. The curve of open circles 196 is the mean of the differences, and the curves of black circles and lines 198 are the plus-and-minus standard deviation of the differences. It will be noted that the uncertainty at 1 day used for prediction 200 and 202 is much wider than the uncertainty at 35 days used for prediction 204 and 206.

In the glucose median difference plot, the standard deviation represents the uncertainty of the predicted median in terms of mg/dL. The uncertainty increases as the number of days of data collected decreases. The choice of the minimum number of days balances the measurement uncertainty with the costs of collecting a number of days of data. The FIG. 29 shows that there is very little improvement in the prediction certainty beyond 14 days. The figure also shows that for any duration of less than four days, the measurement uncertainty increases very rapidly. Five days was chosen as a minimum number of days for clinical relevance as it represents a reasonable compromise between prediction certainty and restrictions in GCM availability. The uncertainty at five days is no more than twice the minimum uncertainty, and valid glucose readings over five days should be easily collected during a sensor wear of one week.

Many of the same features are evident in the glucose 10th percentile difference plot of FIG. 30. The measurement uncertainty increases as the number of days decreases. Again, there is little improvement after 14 days. Again, there is a rapid increase in the spread for small numbers of days and a 5-day minimum seems like a good compromise.

The data sufficiency rules are designed to utilize all of the valid data available, which will result in the most accurate percentile estimates most of the time.

Alternate Embodiment of Control Grid

This describes an alternate way to construct the lines on the Control Grid. The Control Grid has three grades of hypoglycemic ("hypo") risk: high, medium, and low, separated by two lines. There are three grades of glucose variability: high, medium, and low, also separated by two lines. This new variant of the Control Grid defines the boundary lines between medium and low in the same way as the boundary lines between high and medium.

Figure 59:
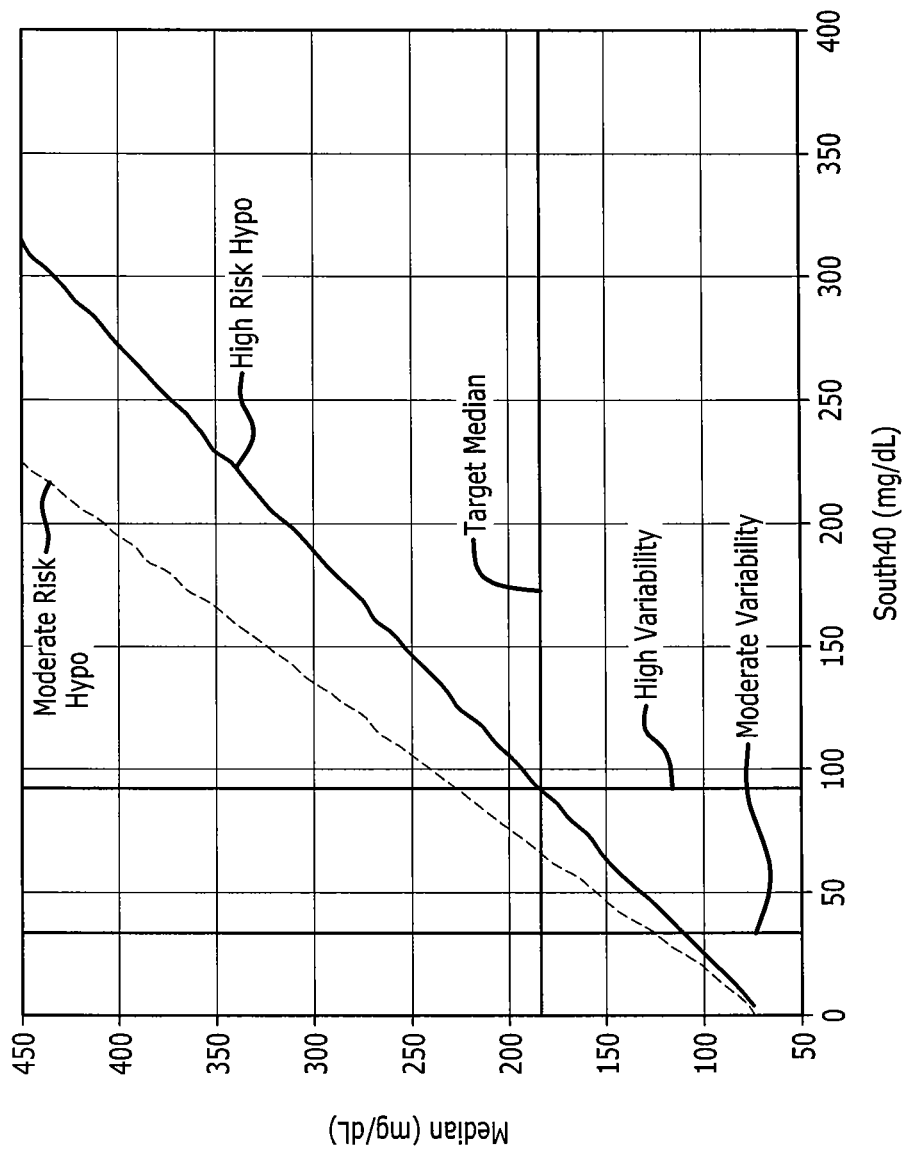
FIG. 59 shows the main control grid lines.

At the present time, the Control Grid is defined by five major lines as shown in FIG. 59. These are:

1. Target median line (horizontal)—It is desirable that the subject's median glucose value be below this line.

2. High risk hypo line—A Control Grid position below this line indicates an excessive risk of hypoglycemia. All points on this line have a constant value of our hypoglycemic risk metric: the area under the hypo threshold of 70 mg/dL.

3. Extreme variability line (vertical)—Placed at the intersection of the target median line and the high risk hypo line. A Control Grid position to the right of this line indicates excessive variability in glucose value, Excessive variability makes it impossible to be below the target median and not be exposed to excessive risk of hypoglycemia.

4. Moderate risk hypo line—A Control Grid position above this line indicates that there is no significant risk of hypo, and that the insulin dosage can safely be increased. This line is chosen such that its distance from the high risk hypo line is a linearly increasing function of South40. Thus, the moderate risk line and the high risk line form a cone. The actual position of the moderate line is chosen to keep the number of hazardous errors to 10% or less, with 95% confidence. A hazardous decision is defined as calculating the Control Grid position to be above the moderate risk hypo line while the "true" Control Grid position is below the high risk hypo line. In this case, the estimate would indicate that the subject's average glucose could safely be decreased, but in reality, the subject's risk of hypoglycemia is already too large.

5. Moderate variability line (vertical)—Placed to the left of the extreme variability line at a position that seemed reasonable based on collected data and based on comments from our medical collaborator.

Figure 60:
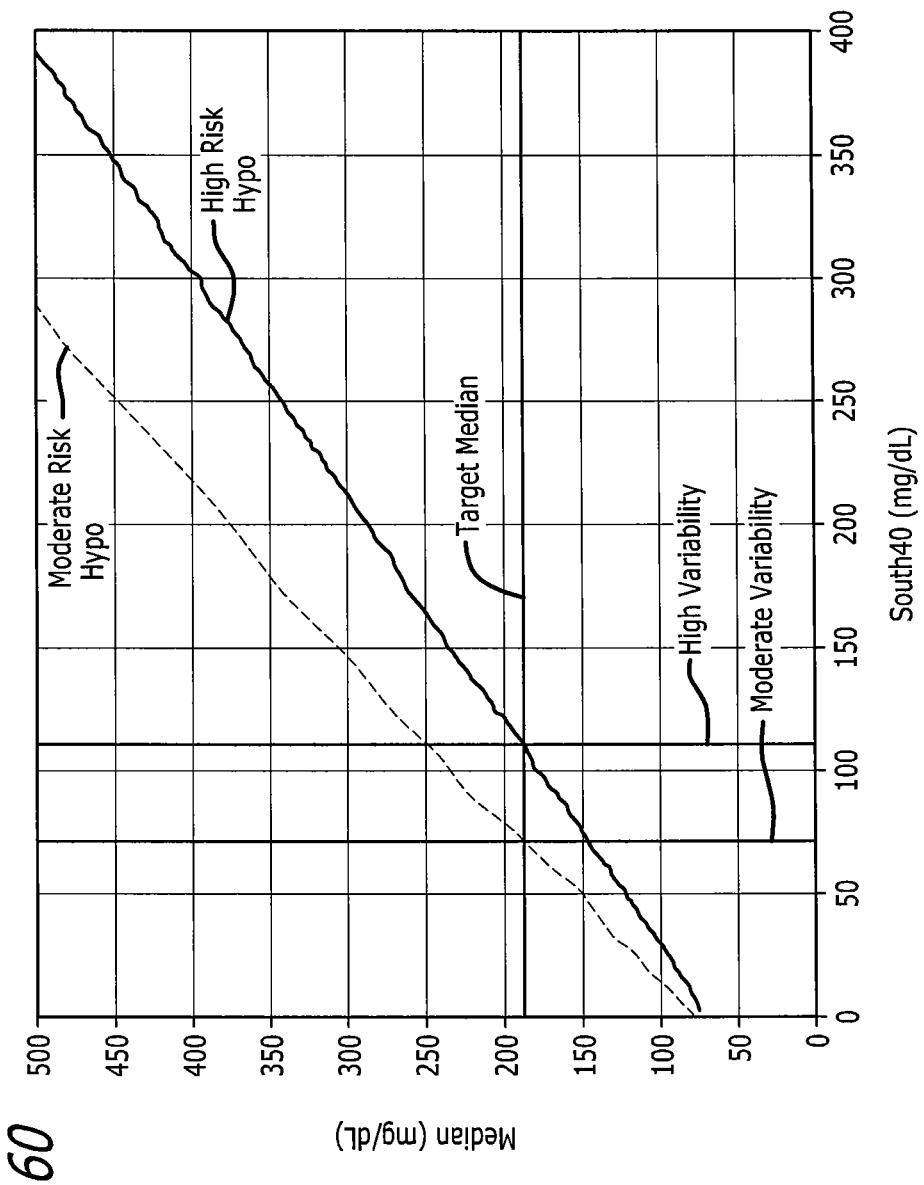
FIG. 60 is a view of an alternate embodiment of the control grid.

In the alternate embodiment, as shown in FIG. 60, the way the moderate hypo risk line and the moderate variability line are calculated is different. In particular, the moderate risk hypo line has been made to be a true hypo line, like the high risk hypo line. The moderate risk can be defined by a constant value of the hypo metric (a smaller value than the high risk hypo line). Furthermore, the location of the moderate line can be chosen to satisfy the same requirement as before; i.e., that there is 95% confidence that no more than 10% of our estimates are hazardous errors. In addition, the moderate variability line can be placed at the intersection of the target median line and the moderate hypo risk line. A Control Grid position to the right of the moderate variability line makes it impossible to be below target glucose with negligible risk of hypoglycemia.

Both changes discussed above will simplify the construction and interpretation of the Control Grid, instead of the two hypo risk lines and the two variability lines being constructed and placed in unique ways, there are now two pairs of lines: one hypo risk line and one variability line in each pair. The hypo risk line shows a constant level of hypo risk across the Control Grid. The associated variability line is placed at the intersection of the hypo risk line and the median target line. Thus, it marks the maximum amount of glucose variability that is compatible with being at target and not being exposed to the associated level of hypoglycemic risk.

Improvement in Glucose Data Quality

Improving the quality of glucose data retrieved from a monitor can result in more accurate and successful management of a subject's diabetes affliction. A more robust analysis of the glucose median and glucose variability can be made. In the past, glucose data has been collected and analyzed unconditionally. This led to biases in the glucose data as certain conditions (e.g. times of day) were over or under-represented. This then led to inaccurate analysis as the collected sample, upon which the analysis was based, was not truly representative of the population of data for the patient.

In addressing this problem the gaps in glucose data scans of the patient should be considered. A retrospective analysis of data should be made to identify gaps in the data scans. Glucose data should be uploaded and analyzed for such gaps in the scans. Once those gaps have been identified, one or more reminder schedules are made that can reduce the gaps. Suggestions are provided to the HCP in the management system of the patient's diabetes. This information is also sent to the patient's self-monitor of blood glucose ("SMBG") instrument or system, or the patient's on-demand meter in order to set up the optimal scan reminders for the near future.

As an example, an evaluation is made of glucose data for data gaps due to historical scan patterns relative to simple high level time concepts. Examples of time concepts include the day of the week (e.g. Monday), the time of day (e.g. morning), and basic meal markers (e.g. dinner). From that evaluation, a determination of the ideal reminder times relative to any of the high level concepts that correspond to the most frequent data gaps are made. As an example, suppose a scan gap is identified that corresponds to a particular day of the week, such as Saturday. Also, suppose the best scan time as determined by the previous sensor glucose ("SG") data is around 10:00 a.m. on Saturday. This information would be stored in the patient's computer aided decision support ("CADS") system. One or more sets of these conditions (e.g. "3 hours after dinner"), with each new set being a lower priority condition from the prior set would be stored and programmed into the management system.

Figure 61:
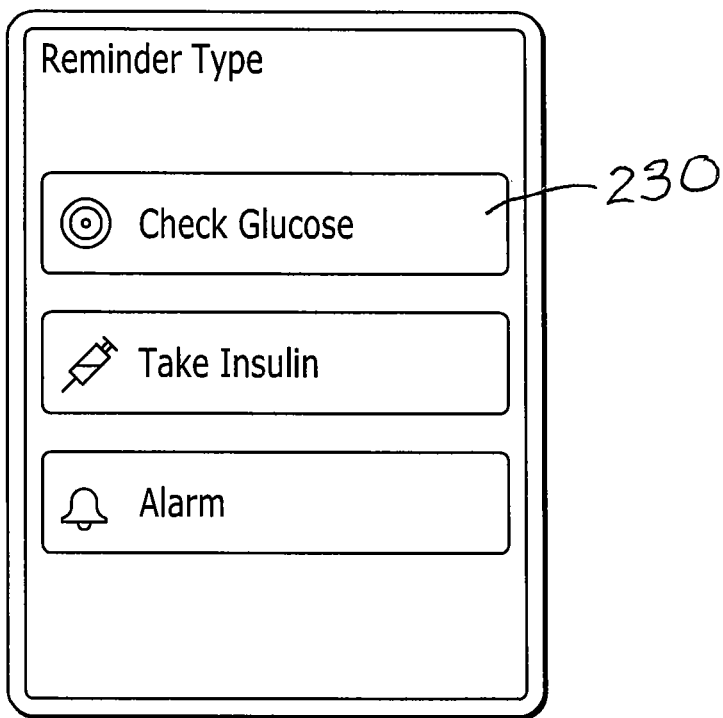
FIG. 61 shows a remainder type menu in the on-demand reader screen.

The HCP informs the patient of these common time gaps and when to best perform glucose data scans to address the gap for the next visit. The option to upload this information back to the Reader or Insulinx meter is given, and using the information as suggested reminder settings would be considered. For example, the patient may add a new reminder, and would choose a "Check Glucose" 230 type of reminder as shown in FIG. 61.

Figure 62:
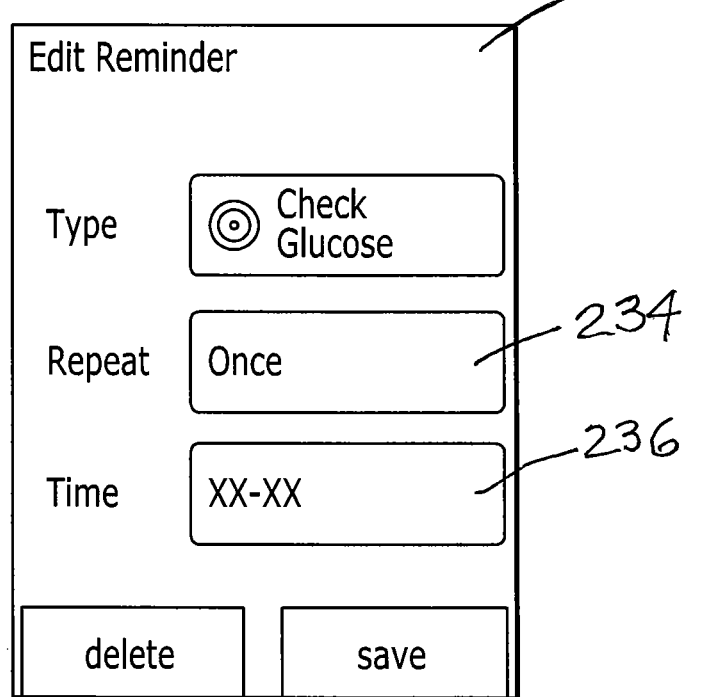
FIG. 62 shows an edit reminder menu in the on-demand reader screen.

FIG. 62 shows the Edit Reminder menu 232 in the on-demand-Reader screen for accomplishing the incorporation of reminders into his/her glucose management program. Then, the "Repeat" 234 and "Time" 236 fields would be pre-populated based on the highest priority condition.

Gamma distribution test—The quality of fit to a Gamma (or any other) distribution can be determined by a number of standard tests, such as the Kolmogorov-Smirnov, Anderson-Darling, or Chi-Square test. The threshold above which the fit is considered good is most likely a function of the number of data points, and must be found empirically.

Regarding further consideration as to reminders of glucose data scan gaps, such reminders could be raised at predefined intervals/fixed times of day (e.g. 7 AM, 3 PM, 11 PM) to ensure full coverage. Reminders could also be raised whenever a gap is imminent (i.e. when an uncaptured data point is about to be overwritten).

Progress is evaluated on a consistent basis. If a certain number of scans per time of day are requested (e.g. 4 morning, 4 midday, 4 evening, 4 night), the progress toward this goal would be indicated with checkboxes for each requested scan. Progress could also be further subdivided into how many readings in each time bin (e.g. hour) either numerically or graphically (e.g. bars or lines).

Data interpolation to improve therapy related metrics is also performed to result in data quality improvement. Some of the SG based artifact detection systems and methods already perform some form of interpolation as long as the gap is no longer than thirty minutes. Filling these gaps can improve the accuracy of metrics that count discrete events. Examples include a metric that tracks the distribution of durations of hypo events below a pre-determined threshold, and a metric that tracks the time interval between prior hypo recovery and the onset of the subsequent hypo event.

The above-described management of glucose data and presentation of analyses and measures, as well as obtaining more robust data and providing other results of analysis and management of the glucose data is carried out by the system and method shown in FIG. 20. For example, the CGM analysis program 136 is broad in nature and may provide the Advanced Daily Patterns (ADP) report 100, the glucose measure tables 108, and the control grids 28A, as well as perform the other data calculations and provide other results.

Appendix A—Glucose Distribution Model

The mathematical basis for the present methodology is to treat the glucose data as a statistical distribution. The lognormal, Gamma, and Weibel distributions are logical choices because, like glucose values, none allow zero or negative values, none restricts the maximum value, all have a single peak, and all are skewed toward high glucose values.

The formulas for these distributions are:

$$\ln N(x; \mu, \sigma) = \frac{1}{\sqrt{2\pi}\,\sigma x} e^{-\frac{1}{2}\left(\frac{\ln(x)-\mu}{\sigma}\right)^2}$$

$$G(x; a, b) = \frac{1}{b\Gamma(a)}\left(\frac{x}{b}\right)^{a-1} e^{-x/b}$$

$$W(x; a, b) = \frac{a}{b}\left(\frac{x}{b}\right)^{a-1} e^{-(x/b)^a}$$

where "a" is the shape factor and "b" is the scale factor. Both the Gamma distribution and Weibull distribution undergo drastic shape changes for $\alpha \le 1$. The shape factor is restricted to values greater than 1.

The lognormal distribution drops off rapidly (proportional to $\exp(-x^2)$ on both sides of its peak value. This is known as a "thin tailed distribution." In contrast, the Gamma has fat tails on both sides of its peak. The Weibull has a fat tail on the low side. The tail on the high side depends on the value of the shape factor. To choose from these three distributions, data from the 40-Day Home Use Study were used. The study consists of 125 subjects using Navigator for (up to) 40 days.

Only processed (10-minute) data are available. The first 20 days are masked; the second 20 days are unmasked.

For this analysis, the study data was split into four categories according to whether the data was masked or not, and what time of day the data was taken. Daytime consists of all data taken from 8 am to 10 pm. The remainder is nighttime.

For each subject, all data in a category are fit to the three distributions and $R^2$ is calculated to determine the goodness of fit. FIG. 31A through 31D shows four plots, where the $R^2$ values have been sorted from low to high across subjects to allow easy comparison of the distributions over all subjects. The abscissa of the plots is the subject where 1 corresponds to all subjects. The ordinate is $R^2$ for the fit for each subject. Thus, a better fitting distribution will rise more quickly towards unity because there are fewer fits with small values of $R^2$. FIGS. 31A through 31D show the $R^2$ of 125 subjects for three distributions. The lognormal distribution is shown to be a much worse fit than the Gamma or the Weibull, thus it is eliminated from further consideration.

Figure 32:
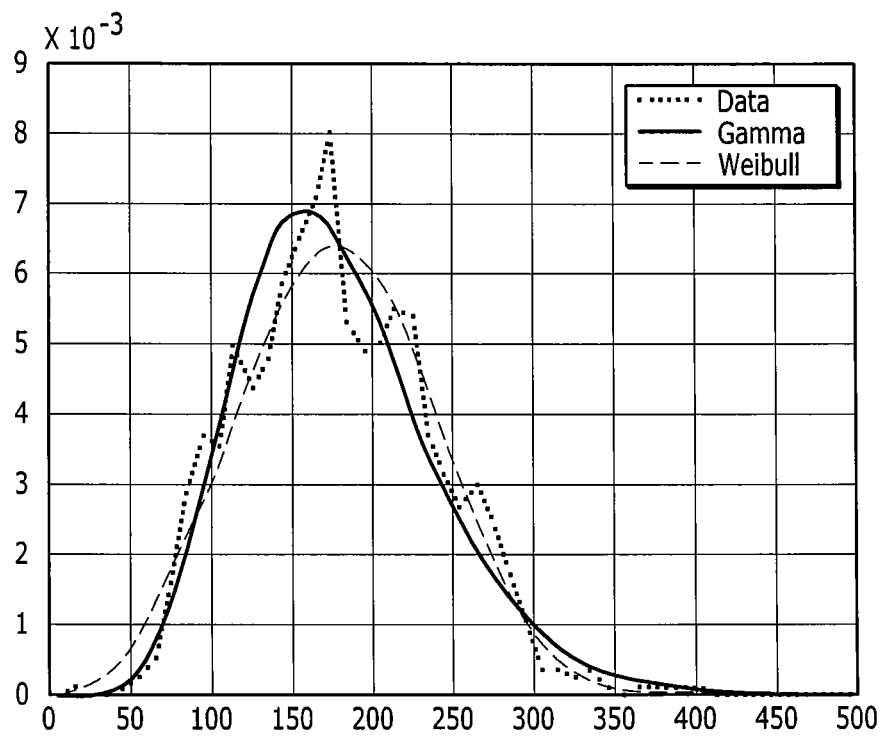
FIG. 32 is a plot of Gamma and Weibull distributions versus a histogram of data.

FIG. 32 shows the Gamma and Weibull distributions versus a histogram of data. In FIG. 32, the Gamma and Weibull distributions are shown overlaying the data histogram for a specific subject; the plots and the $R^2$ values show that both distributions models fit the data well. The Gamma distribution was selected over the Weibull distribution for representing glucose because the Gamma distribution is mathematically simpler, especially the argument of the exponential. The details of the Gamma fit can be examined more closely by using a quantile-quantile (QQ) plot. In this type of plot, a good fit to the data shows up as a good fit to a straight line.

Figure 33:
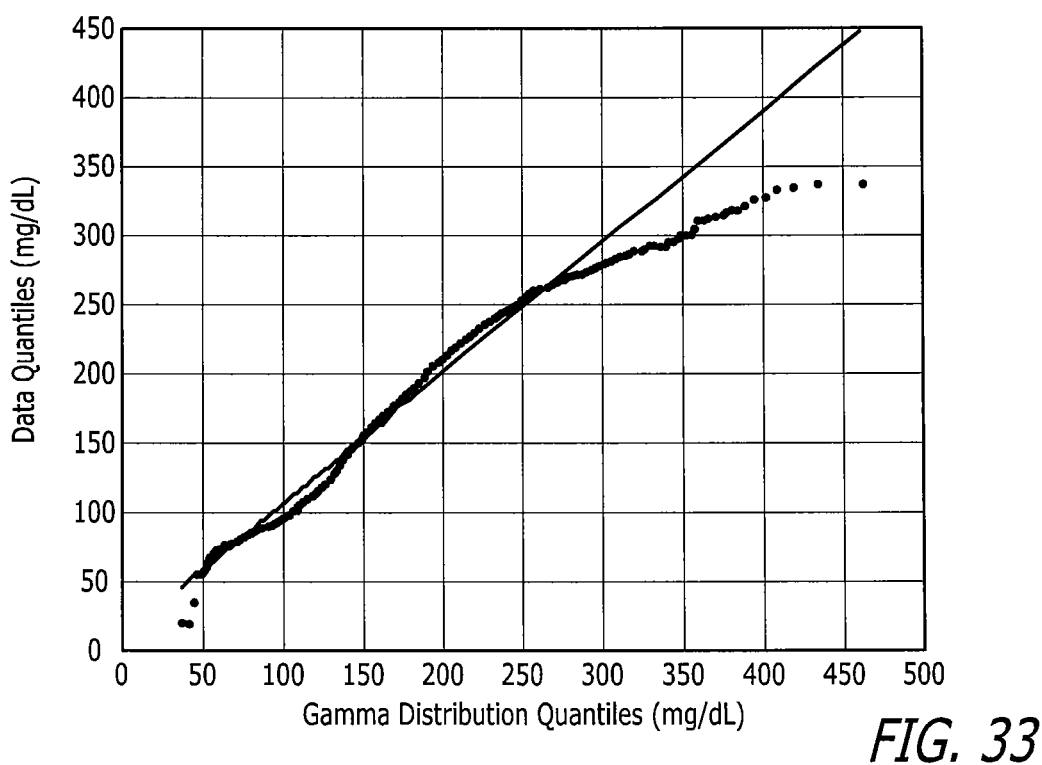
FIG. 33 is a QQ plot for Gamma distribution.
Figure 34:
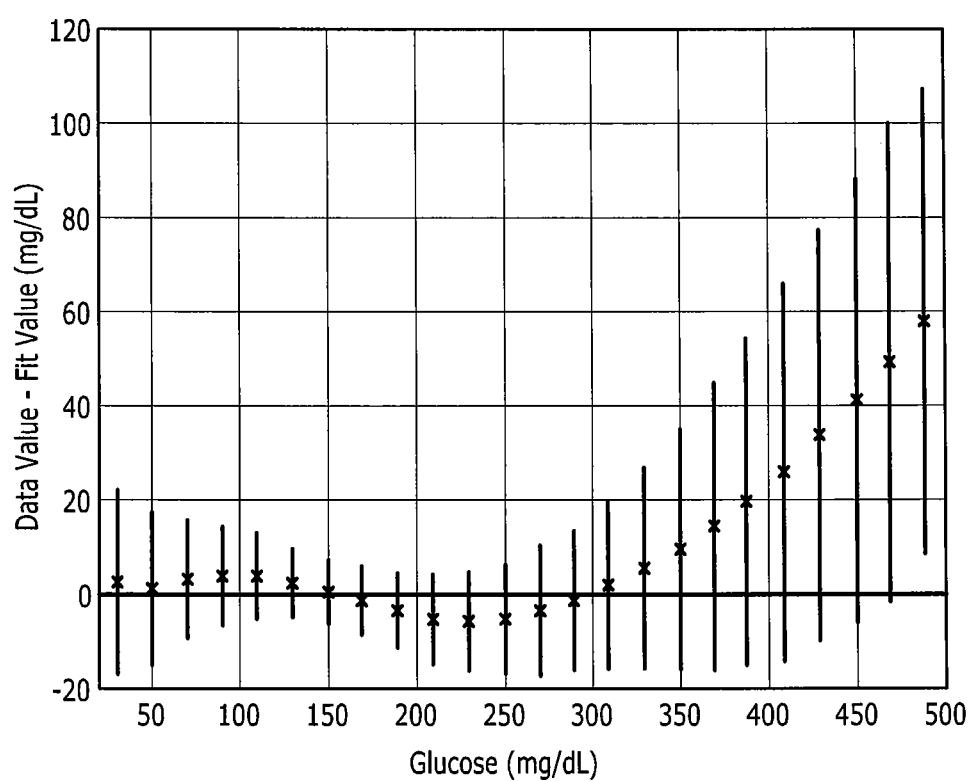
FIG. 34 is a chart of mean±2 standard deviations of the difference between the Gamma and the data.

FIG. 33 shows the QQ plot for Gamma distribution. FIG. 33 shows that the Gamma distribution fit for a single subject. Note that the fit at the low end is better than the fit at the high end. This is typical. FIG. 34 shows the distributions of the differences between the data and the distribution versus glucose value for all subjects.

FIG. 34 shows the Mean±2 standard deviations of difference between the Gamma and the data. Note that at large values of glucose, the bulk of the residuals are positive. This indicates a systematic mismatch between the Gamma distribution and the data. A good fit at low glucose values is important because extreme low glucose events are both dangerous and relatively rare. Thus, the ability to model the low end of the glucose range accurately is important.

The Gamma distribution model is only used for predetermining the Hypoglycemia Risk Curves that are fixed in the present methodology. Specifically, on a median vs. S40 graph, a curve can be defined where the fixed area of the distribution model below 70 mg/dL can be achieved for various values of median and S40. This approach is further described elsewhere in this document with regard to defining Hypo Risk Curves (Appendix E). It is important to point out that, for the present methodology, the distribution model is not used to determine median or S40 estimates for each individual patient/period data set. Because of the concern that parametric estimation of percentiles may introduce additional bias, and because with CG data we'd expect a large number of glucose values to make a good estimate, estimates of median and S40 are determined non-parametrically, directly from the data.

Appendix B—Bias Correction for Median and S40 Estimates

To determine the best estimate of median and S40 from a population of glucose data, it is important to determine under what conditions there may be bias in these estimates, and to compensate for this bias. Bias may be a function of:

The number of days of data collected,
The time of day, and
The duration of the time zone.

One year of unmasked JDRF data was used to estimate bias. Data from each subject was sliced into 21-day segments and into five time zones. All 21 days of data (in each time zone) were used to calculate the "true" values. The estimated values were calculated using durations ranging from one day to 20 days. The boundaries of the time zones were varied to provide different numbers of hours in a time zone, from 3 hours to 12 hours.

Figure 35:
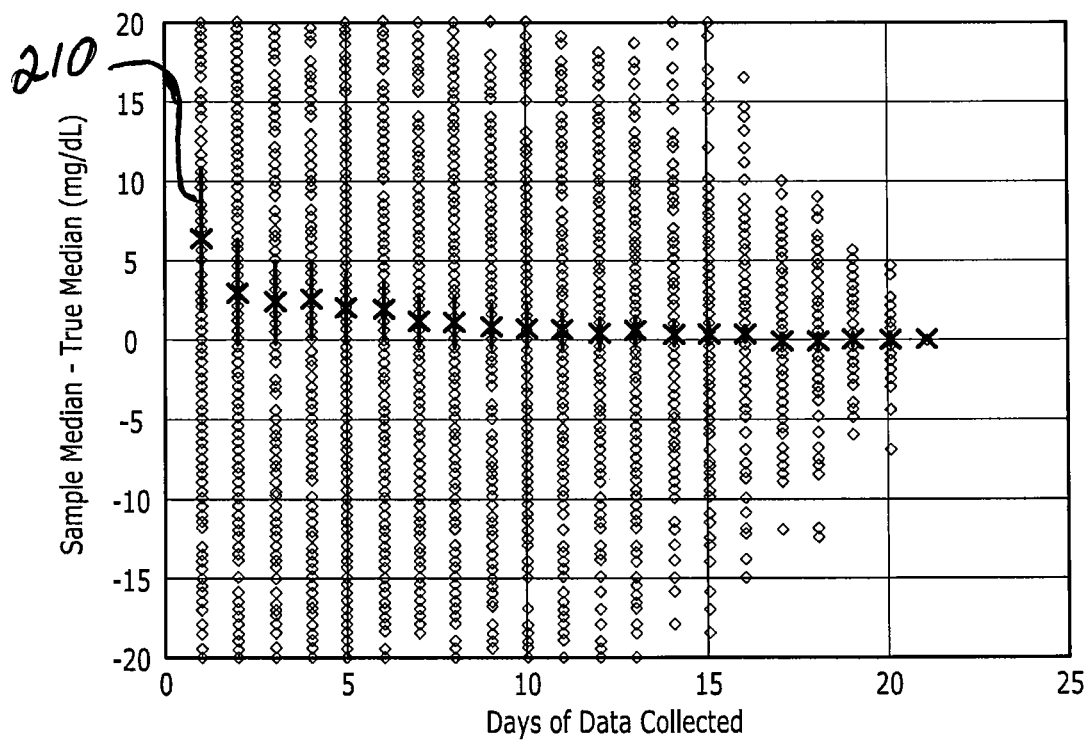
FIG. 35 shows a median bias with an expanded vertical scale.
Figure 36:
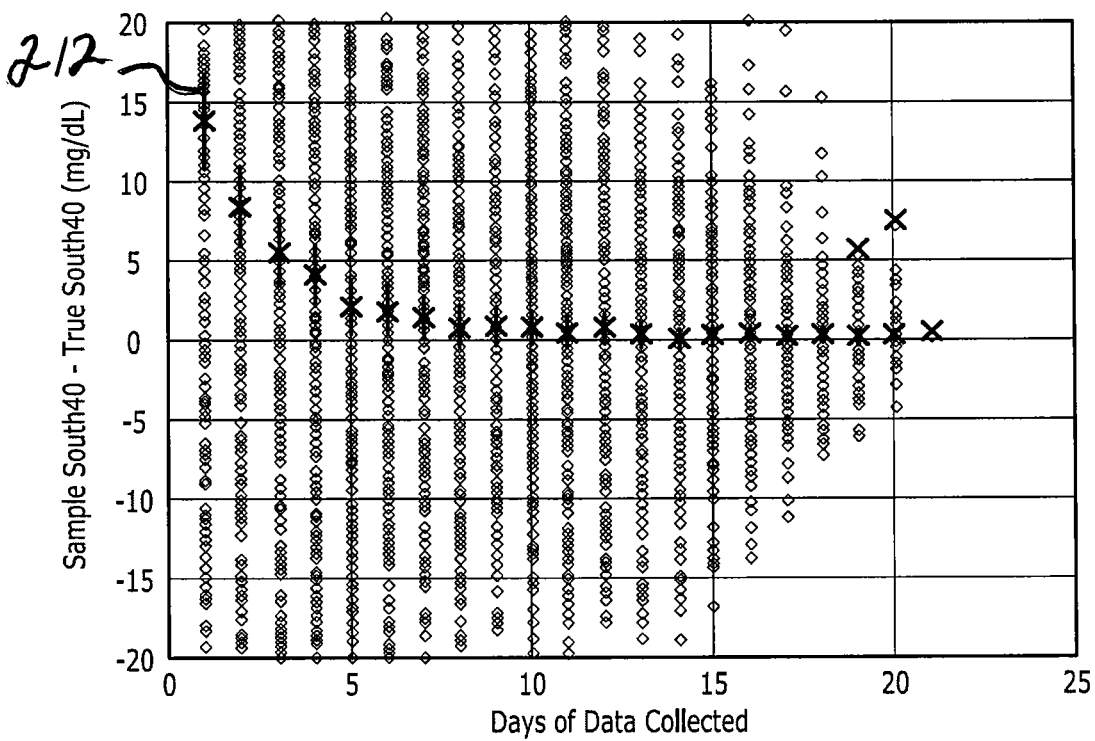
FIG. 36 shows a negative S40 bias with an expanded vertical scale.

FIGS. 35 and 36 show the significance of the nonzero values of the median and negative South40 bias, respectively. The average value is an "x." The "X" bar 210 and 212 spans ±2 standard errors around the average. The y-axis has been expanded so the error bars are more apparent.

The error bar is approximately equivalent to a 95% confidence interval. When this bar includes zero, then any nonzero average value should be considered not statistically significant. In FIG. 35, for the median this occurs for all collection durations greater than one day. Even for a one day collection period, the average is a small fraction of the median value, so the present methodology does not include compensation for median bias.

FIG. 36 shows that the S40 bias is, on the other hand, statistically significant at collection durations greater than five days. In addition, the bias values are a much larger fraction of the typical S40 value.

Figure 37:
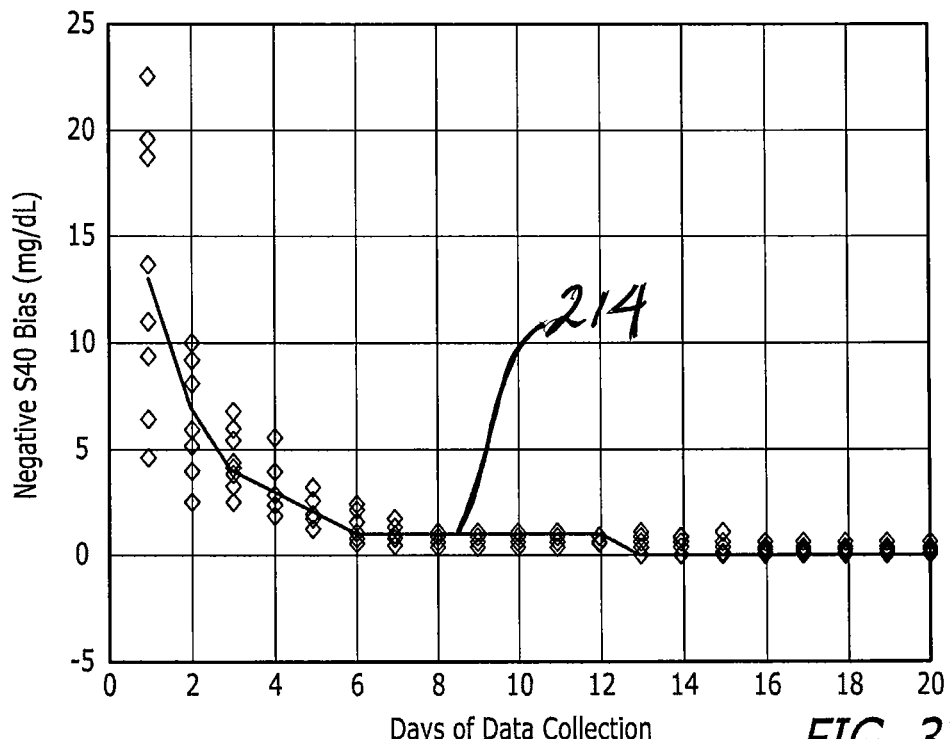
FIG. 37 presents the average over a number of hours in the post-breakfast time zone to make bias a function only of the number of days of data collected.

The S40 estimate bias values in FIG. 36 were smoothed over the number of hours in a time-of-day period as shown by the black line 214 in FIG. 37. This was done for each time-of-day period.

FIG. 37 shows the average over number of hours in the post-breakfast time zone to make bias a function only of number of days of data collected. The S40 bias results for different time-of-day periods and for different durations are gathered in the table below. The table elements in columns 2-6 are the number of mg/dL to add to the calculated S40 value.

| Days | PostBed | PreBF | PostBF | PostL | PostD |
|------|---------|-------|--------|-------|-------|
| 1    | 21      | 27    | 13     | 17    | 18    |
| 2    | 10      | 12    | 7      | 8     | 7     |
| 3    | 5       | 7     | 4      | 4     | 5     |
| 4    | 2       | 5     | 3      | 3     | 3     |
| 5    | 1       | 3     | 2      | 2     | 2     |
| 6    | 1       | 2     | 1      | 2     | 2     |
| 7    | 1       | 2     | 1      | 1     | 2     |
| 8-12 | 1       | 1     | 1      | 1     | 1     |
| 13   | 1       | 1     | 0      | 1     | 1     |
| 14   | 1       | 1     | 0      | 1     | 0     |
| 15   | 1       | 1     | 0      | 0     | 0     |
| 16   | 0       | 0     | 0      | 0     | 0     |

Appendix C—Hypoglycemia Definition

Hypoglycemia can be defined many ways—however, it is necessary for the development of a decision guidance method to settle on a mathematical definition. The metric chosen for use in the present methodology is the so-called AU70 metric, defined as:

a) Sum of all differences (70 mg/dL—Reading) for all Readings below 70 mg/dL,
  b) Divided by total number of readings.
Alternate possible measures of hypoglycemia:
  Fraction of time below 70 mg/dL. This is also known as "time below range." This measure is attractive because it is commonly used and, therefore, easily explained. However, the fractional metric has deficiencies compared to the AU70 metric that are explained further below.
  Low Blood Glucose Index (LBGI) developed by Boris Kovatchev and William Clarke [2]. Glucose values are transformed via a complicated function that makes the risk of malglycemia symmetric across a large range of sugar concentrations. This metric has the advantage of not needing a hypoglycemic threshold. A disadvantage is that it's less intuitive than the other metrics presented here.

The plots in this appendix were produced using data from the following studies: GLADIS, 40-Day Home Use, IDC Observational, JDRF Baseline, JDRF Control, and IDC Healthy. All data was masked. Data from each subject was split in daytime (8 am to 10 pm) and fasting (10 pm to 8 am). This produces two Control Grid locations for each subject.

The following plots show the median-variability plot locations of diabetics (mauve) and non-diabetics (healthy) along with curves of constant hypoglycemic risk ("Hypo Risk Curves") for the three hypoglycemia metrics. The Hypo Risk Curves for all metrics have strong similarities. The Hypo Risk Curves for "Fraction" and AU70 converge near 70 mg/dL at the left edge of the Control Grid. The Hypo Risk Curves for LBGI don't completely converge, but there is no explicit hypo threshold for this hypoglycemia definition. Curves for all metrics tend to fan out with increasing South40.

There are some differences in detail, especially at the left edge. The LBGI curves show marked curvature upward. The AU70 curves show less, and the Fraction curves are virtually straight or even bent slightly in the other direction. This detail is important when the location of the healthy subjects (healthy dots) is taken into account. There is a tendency for the AU70 curves to bend underneath the healthy subjects, which is desirable because healthy subjects do not, by definition, have excessive hypoglycemic risk. While the LBGI curves have this same type of curvature, the lines hit the axis at higher values than the Area lines and thus do not miss the healthy subjects.

Figure 38:
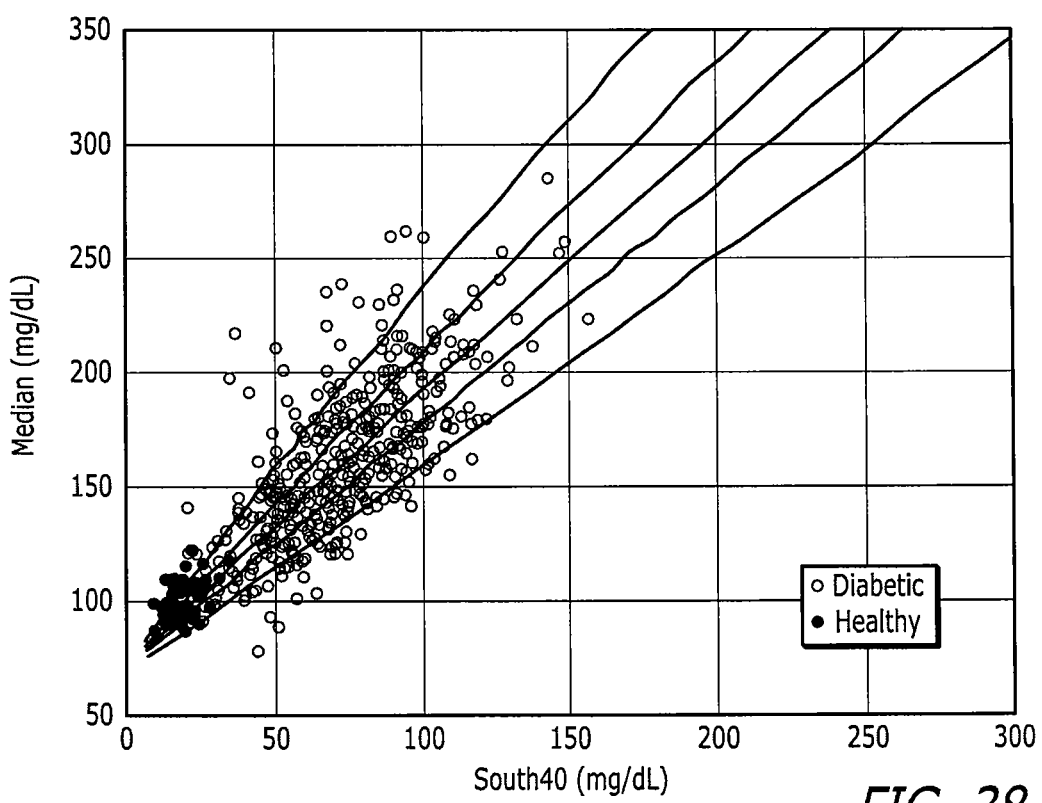
FIG. 38 shows curves of constant hypoglycemic risk using fraction under threshold as the definition of hypoglycemia.
Figure 39:
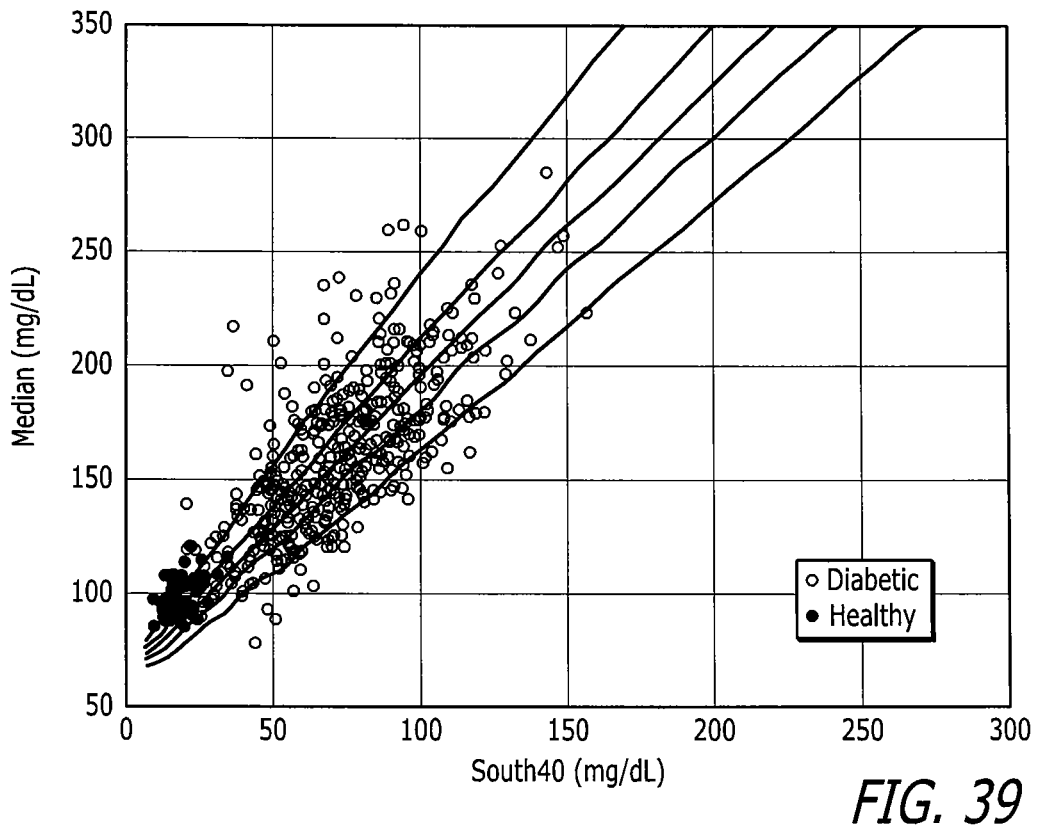
FIG. 39 shows curves of constant hypoglycemic risk using AU70 (area under 70) as the definition of hypoglycemia.
Figure 40:
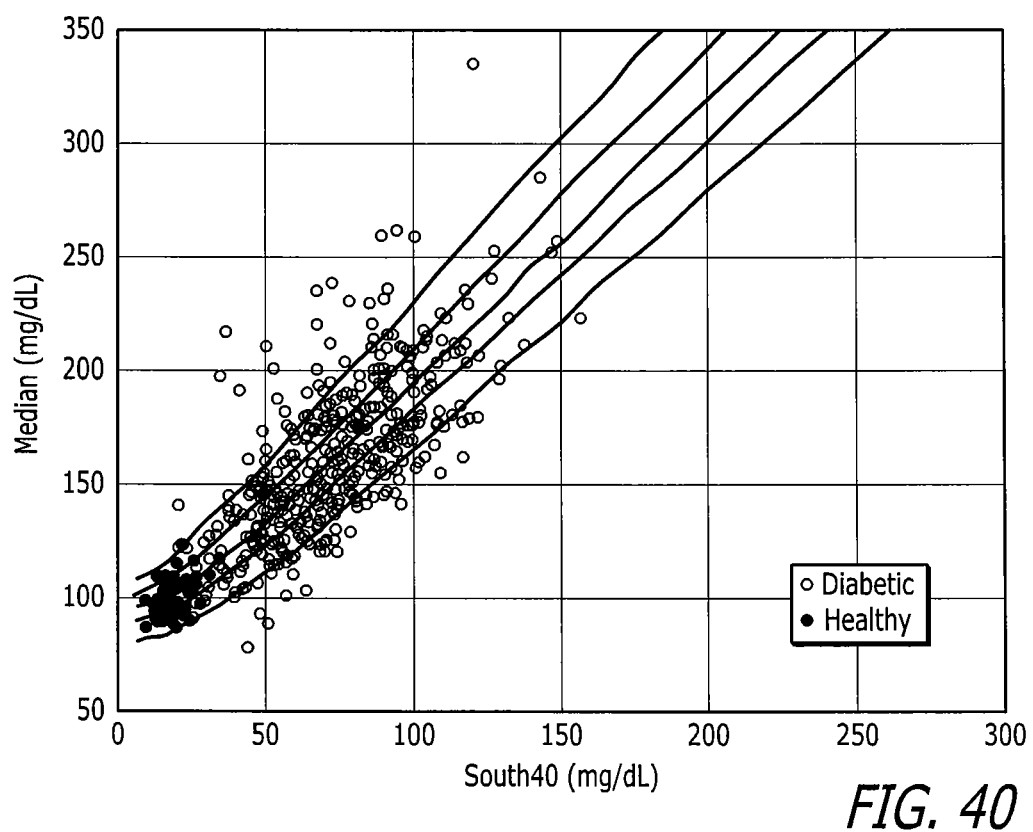
FIG. 40 presents curves of constant hypoglycemic risk using LBGI (low blood glucose index) as the definition of hypoglycemia.

FIG. 38 shows curves of constant hypoglycemic risk using fraction under threshold as the definition of hypoglycemia. FIG. 39 shows curves of constant hypoglycemic risk using AU70 as the definition of hypoglycemia. FIG. 40 shows curves of constant hypoglycemic risk using LBGI as the definition of hypoglycemia.

There are some differences in detail, especially at the left edge of the plots. The LBGI curves show marked curvature upward. The AU70 curves show less, and the Fraction curves are virtually straight or even bent slightly in the other direction. This detail is important when the location of the healthy subjects (healthy dots) is taken into account. There is a tendency for the AU70 curves to bend underneath the healthy subjects, which is desirable because healthy subjects do not, by definition, have excessive hypoglycemic risk. While the LBGI curves have this same type of curvature, the lines hit the axis at higher values than the Area lines and thus do not miss the healthy subjects. Therefore, the AU70 metric was chosen for the methodology primarily because it appears to handle low median and variability data in the most reasonable way.

Appendix D—Determination of Hypo Risk Curves

A particular population of glucose data can be modeled by a Gamma distribution. This distribution is uniquely defined by the median and South40 determined from the data population.

The median and South40 metrics define a point on the median-variability plot. Each point on this plot has an associated value for the AU70 metric determined by:

$$A = \int_0^{70} (70-G) \text{Gamma}(G;a,b) dG;$$

Here, Gamma (G; a, b) is Gamma distribution, G is the glucose value in mg/dL, and a and b are the Gamma distribution shape and scale parameters. The parameters a and b uniquely specify the Gamma distribution. For the present method, specifying the median and the South40 also similarly specifies the Gamma distribution uniquely.

Figure 41:
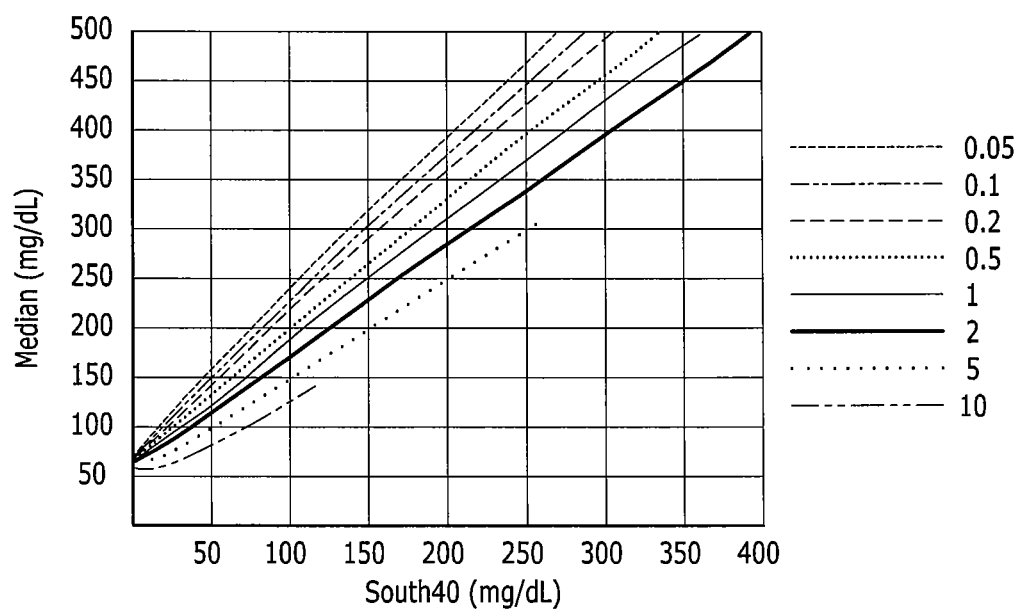
FIG. 41 shows curves of constant AU70 on the median-variability plane.

A curve made up of points associated with constant AU70 value can be determined analytically using the above equation. This curve is called the "Hypo Risk Curve" and each curve is associated with a particular Low Glucose Allowance setting (that is, a particular AU70 value). FIG. 41 shows 8 hypo risk curves on a median-variability plot, each associated with a different AU70 value.

FIG. 42 shows curves of constant AU70 on the median-variability plane. For the present methodology, three different Hypo Risk Curves are predefined as described above, one for each Low Glucose Allowance setting. In FIGS. 42 to 44, the three different Hypo Risk Curves overlay median-variability planes containing median and S40 points calculated using data from the first two weeks of the JDRF study. The data was sorted into five different time-of-day periods. The point is represented as a solid "O" if the AU70 calculated using the patient/period data exceeds the Low Glucose Allowance at the medium setting; otherwise, the point is represented as an open "O." Note that points are only included if 10 glucose readings were available across at least 5 days to calculate the median and variability metrics. These figures illustrate how well the hypo risk curve divides the median-variability plot into zones of high risk and low risk for hypoglycemia.

FIGS. 42 to 44 show hypo risk performance for pre-breakfast with an LGA=large, medium, and small, respectively.

Hypoglycemia detection performance of the Hypo Risk Curves is estimated in terms of sensitivity and specificity as follows. Given a theoretically derived curve of constant AU70 that separates acceptable hypo risk (above the curve) and excessive hypo risk (below the curve), the population of median-variability plane points is split into four groups. First, the population is split into points with excessive measured hypoglycemia, where
  Measured AU70≥AU70 associated with the Hypo Risk Curve,
and points with acceptable measured hypoglycemia. In the above figures, this is represented as solid and open points, respectively. This indicates the true system state. Second, the population is split into points where the system alarms,
  Location on the median-variability plane ≥Hypo Risk Curve,
and points where it doesn't. This represents the detector. In the above figures, these points are respectively below 222 and above 220 the Hypo Risk Curve 224.

Now the four groups of points are defined
Detection: point shows excessive measured hypoglycemia and the detector alarms (solid point below the line).
Missed detection: point shows excessive measured hypoglycemia and the detector does not alarm (open point above the line).
False alarm: point shows acceptable measured hypoglycemia and the detector alarms (open point below the line).
True negative: point shows acceptable measured hypoglycemia and the detector does not alarm (open point above the line).

In general, it is desirable to have as few missed detections and false alarms as possible.
The sensitivity is defined as:

$$\frac{\text{Detections}}{\text{Detections} + \text{Missed detections}} = \frac{\text{Detections}}{\text{All points with excessive measured hypo}}$$

The specificity is defined as:

$$\frac{\text{True negatives}}{\text{True negatives} + \text{False alarms}} = \frac{\text{True negatives}}{\text{All points with acceptable measured hypo}}$$

The table below summarizes the sensitivity and specificity results for each time-of-day period and LGA setting (Large=1.94; Medium=0.83; Small=0.35)

| LGA setting | TOD Period | Sensitivity % | Specificity % |
|---|---|---|---|
| Large | Pre-breakfast | 97 | 92 |
| | Post-breakfast | 91 | 93 |
| | Post-lunch | 94 | 93 |
| | Post-dinner | 86 | 94 |
| | Post-bedtime | 97 | 94 |
| Mediun | Pre-breakfast | 92 | 77 |
| | Post-breakfast | 88 | 89 |
| | Post-lunch | 90 | 81 |
| | Post-dinner | 90 | 78 |
| | Post-bedtime | 90 | 83 |
| Small | Pre-breakfast | 91 | 65 |
| | Post-breakfast | 90 | 71 |
| | Post-lunch | 92 | 63 |
| | Post-dinner | 95 | 65 |
| | Post-bedtime | 89 | 71 |

Appendix E—Variability Metric Comparison

Two alternate variability formulas are compared to the S40 in terms of the ability to estimate the risk of hypoglycemia:
1. Interquartile range (IQR), the difference of the $75^{th}$ and $25^{th}$ percentiles, and
2. The difference of the $90^{th}$ percentile and the $10^{th}$ percentile, colloquially known as the "mid80."

Note that both of these alternative measures for variability are symmetric around the median, whereas the S40 measure is only concerned with variability below the median. The hypothesis behind using S40 is that because the glucose population distributions are more accurately modeled by a Gamma distribution at low glucose values, excluding variability measurement above the mean will provide a more accurate estimate of hypoglycemic risk.

Figure 45:
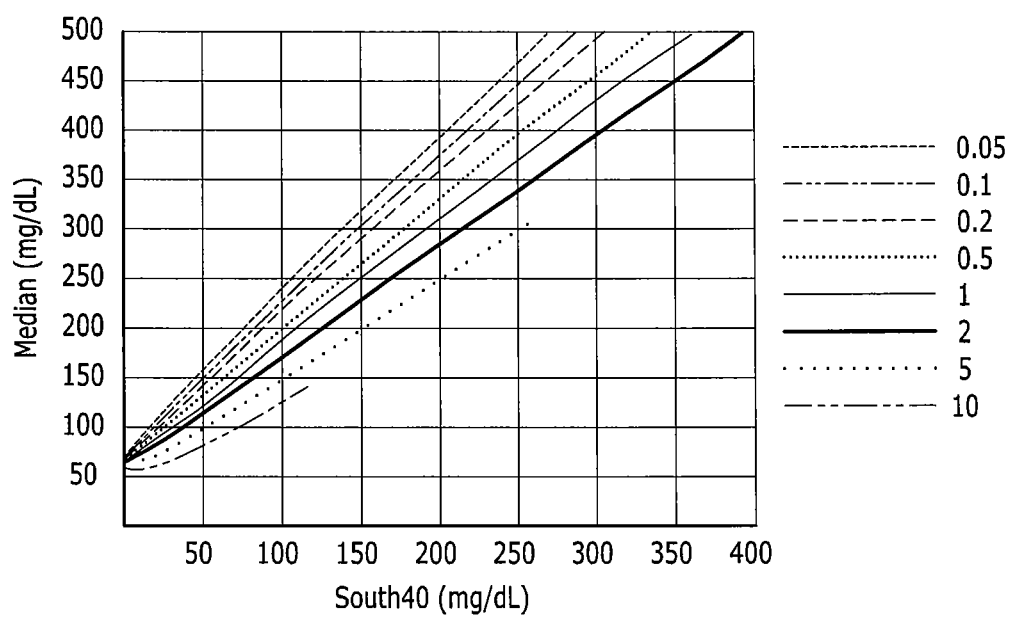
FIG. 45 presents curves of constant AU70 for South40 (measure of variability, discussed below); with the associated AU70 value is shown on each curve.
Figure 46:
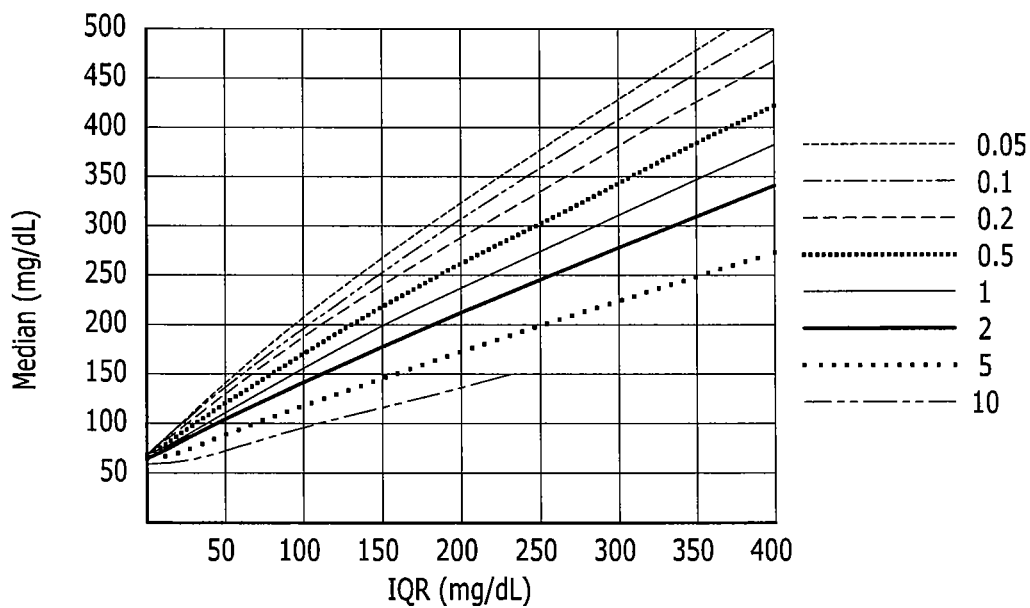
FIG. 46 presents curves of constant AU70 for IQR (interquartile range); with the associated AU70 value shown on each curve.
Figure 47:
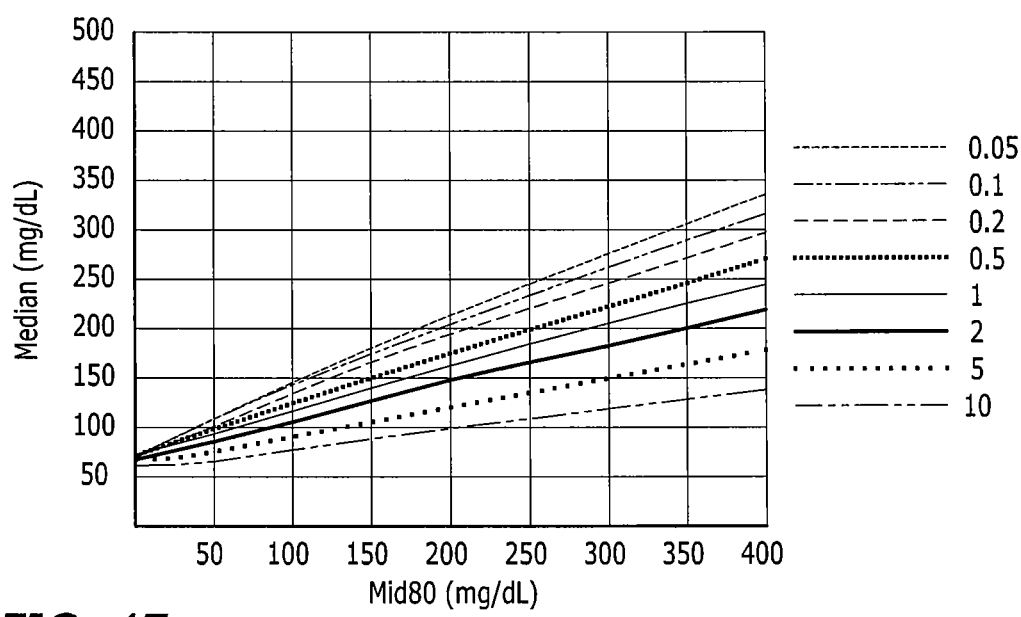
FIG. 47 presents curves of constant AU70 for Mid80, with the associated AU70 value shown on each curve.
Figure 48:
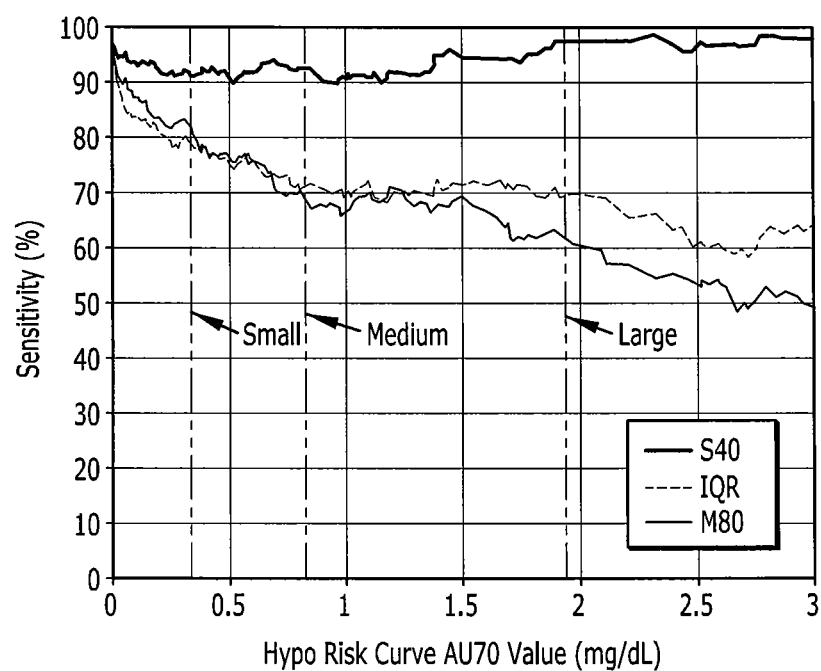
FIG. 48 shows a hypo risk curve AU70 value in mg/dL.

This comparison involves calculating sensitivity and specificity at various values of hypo risk. The following three figures show curves of constant AU70 on the median-variability plane for the three different variability axes.
FIG. 45 shows curves of constant AU70 for South40. The associated AU70 value is shown on each curve.
FIG. 46 shows curves of constant AU70 for IQR. The associated AU70 value is shown on each curve.
FIG. 47 shows curves of constant AU70 for Mid80. The associated AU70 value is shown on each curve.

All three sets of curves have similar characteristics. The Mid80 lines (FIG. 47) have a larger x-axis extent. This is understandable as Mid80 is always larger than south40 or IQR. IQR (FIG. 46) has a larger extent along the abscissa than south40, but it also spreads faster in the vertical direction than the other two.

To evaluate which measure of variability is better at estimating hypo risk, the respective sensitivity and specificities are compared. The first two weeks of the JDRF data set was used for this analysis; the analysis method is described in Appendix D. There are 443 subjects using various types of masked CGM devices. Each subject's data was split into five time-of-day periods.

Figure 49:
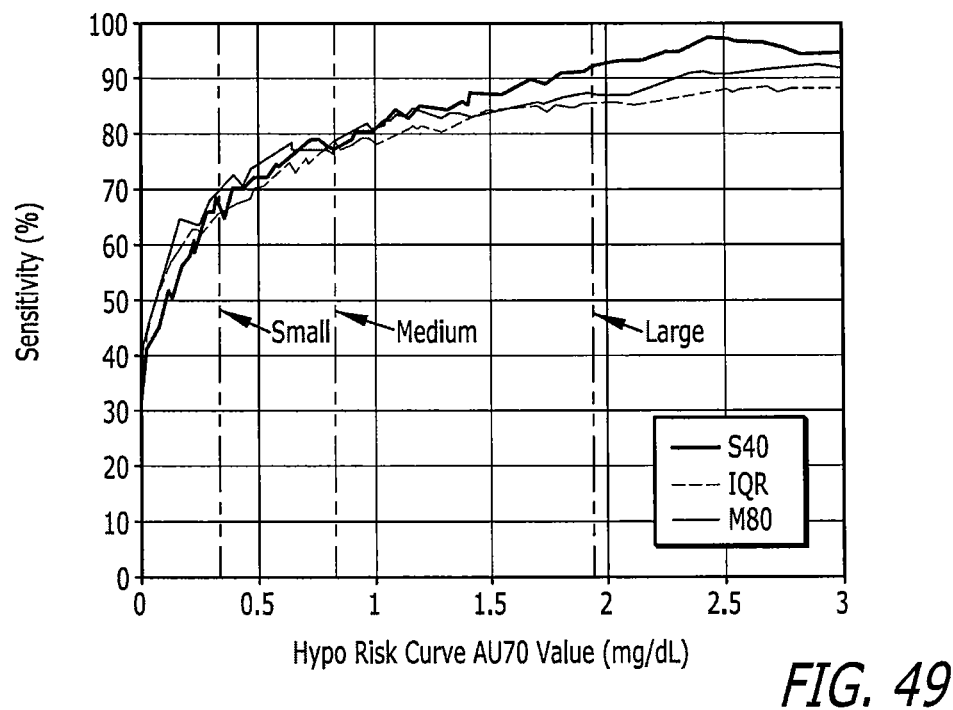
FIG. 49 shows the sensitivity and specificity of the pre-breakfast time-of-day period, with the LGA settings shown as vertical dashed lines for reference.

To determine sensitivities and specificities when the S40 variability is replace with IQR or Mid 80, both the Hypo Risk Curves, and the location and color of the points on the median-variability plane need to be recalculated. The next plot FIG. 49 shows the sensitivity and specificity comparisons for the pre-breakfast time-of-day period, plotted as a function of the AU70 value of the Hypo Risk Curve, from 0 to 3. It can be seen from the figure that the sensitivity is substantially superior when the S40 metric is used to represent variability and the specificity is slightly better.

Appendix F—Low Glucose Allowance Setting Definition

A different Hypo Risk Curve can be determined for any value of AU70. One difficulty is that there is no established clinical guidance on a minimum value of AU70 that would be considered "excessive" or "problematic." Therefore, the present methodology was designed to provide the clinician the ability to adjust the Hypo Risk Curve AU70 value; this is referred to as the Low Glucose Allowance (LGA) setting.

The LGA setting values were determined using the first two weeks of JDRF CGM data, the first 20 days of 40-Day Home use data, the first 20 days of Gladis data, and all 30 days of IDC Observational Data. All of these data are masked.

Figure 50:
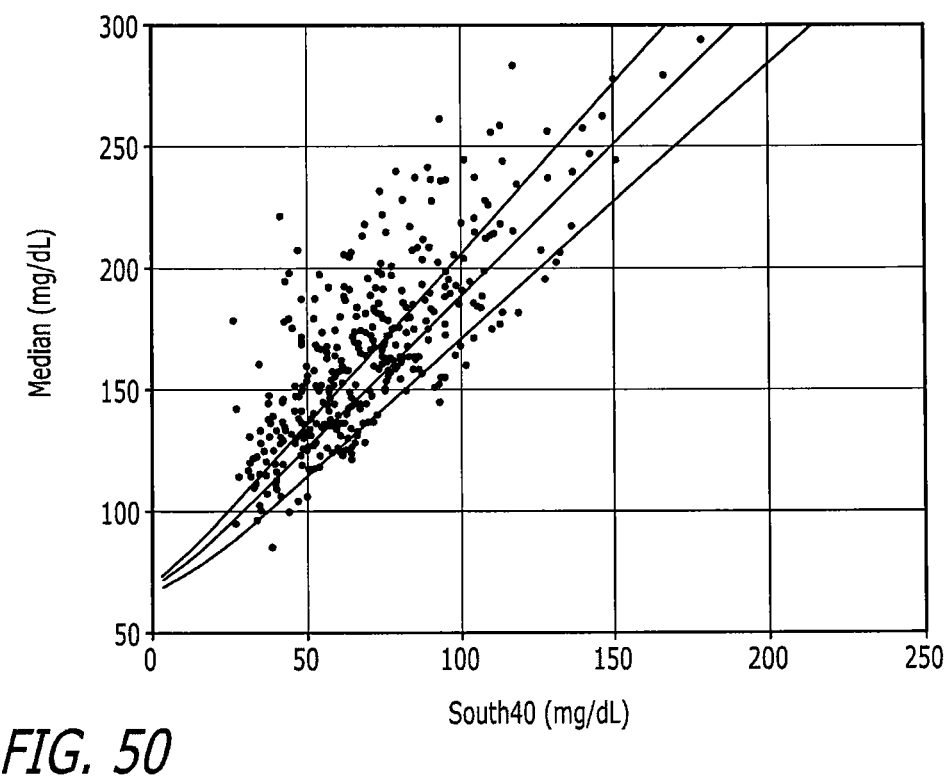
FIG. 50 presents hypo risk curves and post-lunch median-variability points.
Figure 51:
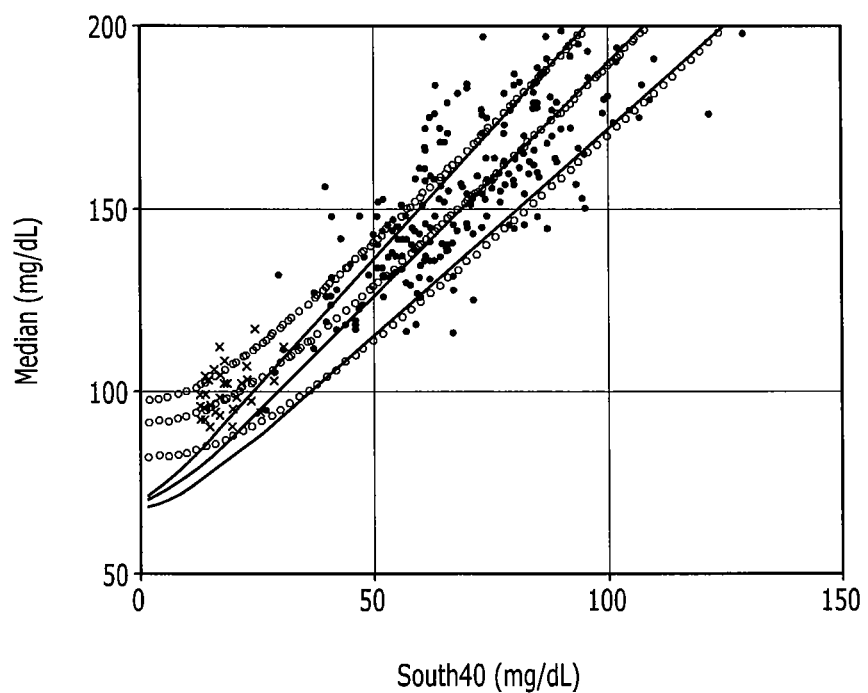
FIG. 51 presents hypo risk curves for each LGA setting and corresponding approximate LBGI curves.

FIG. 50 shows hypo risk curves and post-lunch median-variability points. Median-variability points, one point per subject-period, were calculated for each of the three post-meal time-of-day periods. These results are shown for the Post-Lunch period in FIG. 50. Also, Median-variability points were calculated for a single overnight time-of-day period (that Bedtime and Pre-Breakfast periods were combined). Next, three Hypo Risk Curves were determined empirically for each TOD period such that a) the lowest curve (LGA=Large) separates the 10% "highest hypo risk" points from the rest of the points, b) the middle curve (LGA=Medium) separates the 30% "highest hypo risk" points, and c) the top curve (LGA-Small) separates the 50% "highest hypo risk" points. These curves are shown in FIG. 50 for the Post-Lunch TOD period. The table below shows the AU70 value that corresponds to each curve.

| LGA | Overnight | PostBreakfast | PostLunch | PostDinner |
|---|---|---|---|---|
| Small | 0.55 | 0.31 | 0.35 | 0.45 |
| Medium | 1.34 | 0.85 | 0.83 | 0.97 |
| Large | 3.15 | 1.85 | 1.94 | 1.94 |

One observation is that the AU70 numbers are much larger for the Overnight period compared to the other time-of-day periods. This illustrates that the population was experiencing more hypo risk overnight than during the day.

For the present method, a single column of the LGA was chosen to represent all time periods. The PostLunch values were selected because the Medium (default) AU70 setting is the smallest, and the smallest LGA values are the most conservative in terms if estimating hypo risk.

The final AU70 values are shown in the table below.

| Low Glucose Allowance Setting | AU70 Value |
|---|---|
| Large | 1.94 |
| Medium | 0.83 |
| Small | 0.35 |

The default LGA setting used in the present method is the Medium setting. The reasonableness of this setting was evaluated by having two clinical experts review the ADP report, with the LGA at the Medium setting, for 26 different patients with a broad range of glucose characteristics, to ensure that the analysis results are appropriate; specifically, that each result shown in the GCM table is consistent with corresponding therapy changes that should either reduce excessive hypoglycemia or should safely reduce overall glucose levels without causing excessive hypoglycemia. In practice, judgment of the physician will be used to determine if the LGA should be set to a more conservative setting (Small) or a more aggressive setting (Large) with regard to therapy to reduce glucose levels.

Figure 52:
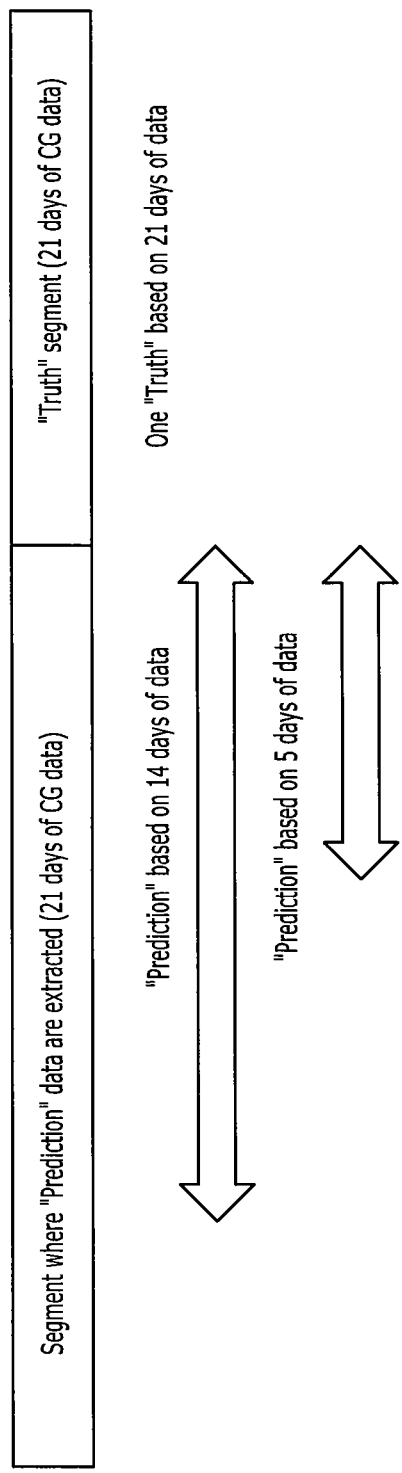
FIG. 52 illustrates the control grid positions of "truth" and "prediction" pairing.

LBGI is another metric used to evaluate hypo risk from glucose data. It is informative to compare the LGA setting values with the LBGI risk threshold, described in [2], that demarcates moderate and high risk (2.5). FIG. 52 below shows curve of equal LBGI value overlaying the Hypo Risk Curves at the LGA values.

FIG. 52 shows hypo risk curves for each LGA setting and corresponding approximate LBGI curves. The LBGI curves are approximately the same as the Hypo Risk Curves in the area where most of the median-variability points lie. The LBGI values that approximately equate to the LGA AU70 values are shown in the table below:

| Low Glucose Allowance Setting | AU70 | LBGI |
|---|---|---|
| Large | 1.94 | 3.5 |
| Medium | 0.83 | 1.60 |
| Small | 0.35 | 0.86 |

Note that the moderate-to-high risk LBGI threshold, 2.5, falls between the Medium and Large LGA settings.

Appendix G—Low Glucose Allowance Threshold Comparison to Report Severe Hypoglycemia For the three possible settings of the LGA, it is interesting to examine how these relate to reported severe hypoglycemia ("SH"). SH was documented in the JDRF-CGM trial, where SH was defined as when the patient at a minimum required assistance to deal with a hypoglycemic episode. Note that only detection sensitivity is appropriate to evaluate here; since SH are rare events over the span of CG data that are provided by the JDRF trial, specificity will be extremely low for all methods, and essentially meaningless.

In this analysis, results from the present methodology are compared to the Low Blood Glucose Index (LBGI) method developed by Kovatchev [2]. These methods were applied to the 14 days of CG preceding the SH events. 48 of the 89 reported SH episodes had all five periods of the day with hypoglycemia forecasts available, and were therefore evaluated by both methods. The detection sensitivity was evaluated by having at least one "Red" forecast of hypoglycemia for the present method and compared to the LBGI "High Risk" (>2.5) forecasts.

The performance of the SH event detection by the present and LBGI methods are shown in Table G3. The detection sensitivity of having at least one "Red" forecast of hypoglycemia by the LLG method was 83% at the default LGA setting ("Medium"), which is comparable to the LBGI "High" result of 79%. The effect of the Low Glucose Allowance setting on the present method can be seen as the detection sensitivity increased to 96% for the more sensitive "Small" setting, and decreased to 44% for the less sensitive "Large" setting.

TABLE G3

Detection sensitivity comparison for LLG and LBGI for 48 severe hypoglycemia events.

| Low Glucose Allowance Setting | Number of "Red" Forecasts (At least 1 of 5 periods of the day) | Number of "High" LBGI Forecasts |
|---|---|---|
| Small | 46 (96%) | 38 (79%) |
| Medium | 40 (83%) | |
| Large | 21 (44%) | |

The SH detection performance was further examined by generating the SH histogram as a function of the distance below:
- The AU70 Hypo Risk Curves
- The LBGI Hypo Risk Curves (values taken from the LBGI table in Appendix F)
- The AU70 Moderate Risk Curves (Appendix H) It was found that these histograms are very similar for all TOD periods. Decreasing the LGA shifts the curve to the right, as expected. The LBGI-inspired curves closely match the AU70 curves. The moderate hypo lines detect over 90% of SH episodes at all LGA settings.

Appendix H—Moderate Hypoglycemia Risk Curve Derivation

The "Moderate" Hypoglycemia Risk Curve supplements the "High" Hypo Risk Curve in order to create a "Moderate" hypo risk zone on the Control Grid. For the patient who has a median-variability point located in the zone defined by these two curves, there is a 10 to 50% chance that the patient is at risk of excessive hypoglycemia. Clinical judgment is required to determine if therapy modifications should be made to reduce hypo risk; however, any steps to lower glucose levels further should be considered with extreme caution.

The size of the buffer zone is driven by a) the natural variation in glucose profile from period to period, and b) uncertainty associated with estimating glucose median and S40 metrics with limited data. The latter source of uncertainty is much less a factor when the metrics are estimated with periodic and frequent CG data, as compared with sparse self-monitored blood glucose (SMBG) data; however, the present method does take into account the possibility of low sample size in determining the appropriate Moderate Risk Curve. The result is that more data will shrink the moderate hypo risk zone; in other words, more data equates to more certainty in the glucose metrics, which may result in the ability to safely make more aggressive treatment decisions. Note that for large amounts of data, however, additional data has diminishing benefit.

For the present method, the Moderate Risk Curves are developed such that the chance of calculating a low hypo risk when the subsequent time period indicates excessive hypo risk is less than 10% with a confidence level of 95%. The JDRF data set was used: 54 subjects with one year's worth of unmasked data. Development was done using the first ⅔ of the subjects, the remainder was used to check the results.

For each of the five default time-of-day (TOD) periods, the development set was sliced into 21-day segments. The Control Grid position for each TOD period was calculated based on 21 days of data. These Control Grid positions make up what is referred to here as the "truth." In the immediately preceding 21-day period, various numbers of days of data were collected and the Control Grid positions calculated. These are referred to here as "predictions." When multiplied by the number of hours in the time-of-day-period, this gives rise to the number of hours of data collected. This construct is illustrated in FIG. 52. The data used for predictions were taken just prior to the data segment for the corresponding truth. The result of this analysis is a collection of Control Grid truths with a number of associated Control Grid predictions from the immediately preceding period, each of different length.

FIG. 52 illustrates the "truth" and "prediction" pairing. The design goal for the Moderate Risk Curve is that, with a confidence level of 95%, less than 10% of the predictions indicate "no hypo risk" (that is, above the Moderate Hypo Curve) when the truth indicates "excessive hypo risk" (that is, below the Hypo Risk Curve). Note that the truth Control Grid positions that are far from the Hypo Risk Curve will have the effect of over-optimistically achieving this requirement; for instance, a truth that is located in the upper left corner of the Control Grid will be easy to detect as "no hypo risk." Likewise, a truth located in the bottom-right corner of the Control Grid is easily detected as "high hypo risk." The truth Control Grid positions that are the most difficult to evaluate for hypo risk, and therefore the most meaningful for the design on the Moderate Risk Curve, are those close to the Hypo Risk Curve. Therefore, to remove the impact of this effect, each prediction Control Grid position will be vertically adjusted by the vertical distance that its associated truth Control Grid position is from the Hypo Risk Curve. Now these vertically-adjusted predictions are associated with truths that are exactly located at the "excessive" hypo risk threshold.

Figure 53:
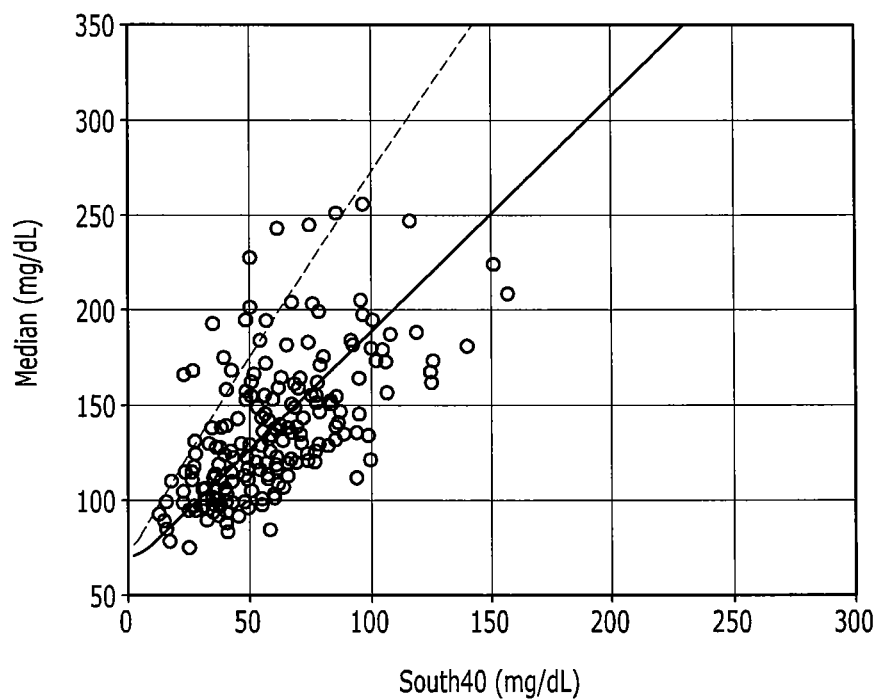
FIG. 53 shows a post-breakfast TOD period using twelve hours (equivalent to three days of data for a four-hour TOD period) of data to make the prediction, with the LGA setting at medium.
Figure 54:
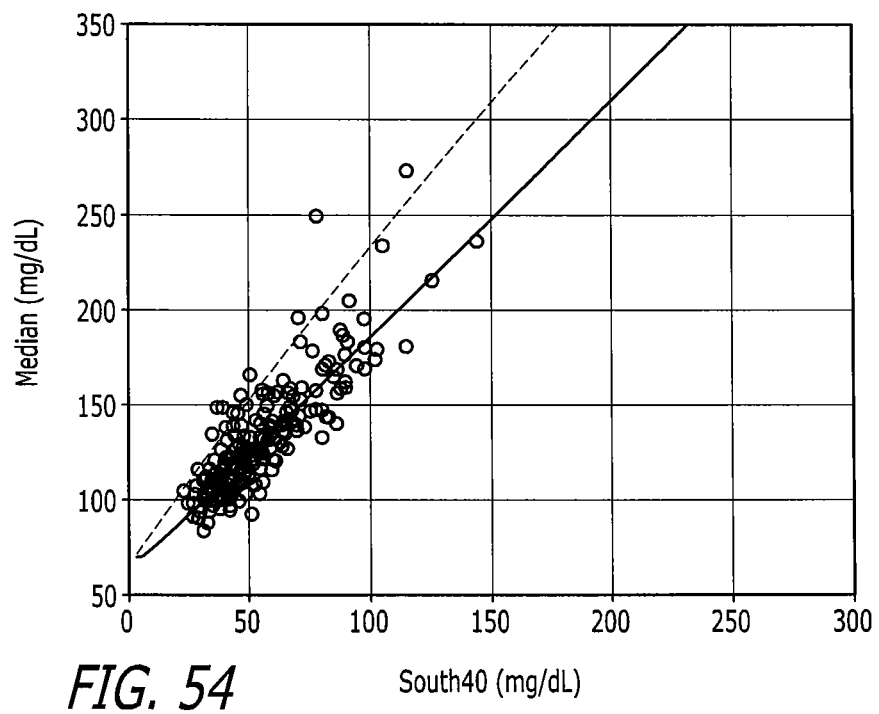
FIG. 54 presents a post-breakfast TOD period using forth hours (equivalent of ten days of data for a four-hour TOD period) of data to make the prediction, with the LGA setting at medium.

As for the Hypo Risk Curves, the Moderate Risk Curves are curves of equal AU70 value based on the assumption of a Gamma distribution. A specific Moderate Risk Curve is determined for each combination of a) the five TOD periods, b) the prediction data lengths varying from 1 to 21 days, and c) the three LGA settings. For each combination of conditions, the Moderate Risk Curve is empirically determined from the set of vertically-adjusted predications, such that, with a confidence level of 95%, less than 10% of the vertically-adjusted predictions indicate "no hypo risk" (that is, above the Moderate Hypo Curve). Note that to achieve a level of confidence of 95%, the Moderate Risk Curve should be positioned so that some number less than 10% of the predictions are above the curve. FIGS. 53 and 54 show examples of this empirical fit.

FIG. 53 shows the post-breakfast TOD period using 12 hours (equivalent to 3 days of data for a 4 hour TOD period) of data to make the prediction. The LGA setting is Medium. In the figure, the Hypo Risk Curve is the black line, and the Moderate Risk Curve is the dashed line. There are about 200 predictions, so to achieve the requirement only 13 predictions can be above the Moderate Risk Curve. To achieve the requirement, this particular Moderate Risk Curve is associated with an AU70 value of 0.0035.

FIG. 54 shows the post-breakfast TOD period using 40 hours (equivalent of 10 days of data for a 4 hour TOD period) of data to make the prediction. The LGA setting is Medium. In FIG. 54, the combination of conditions only differs for that of FIG. 53 in that the period of data used for the prediction is extended from 3 days to 10 days. Note that with more data for the prediction, the Moderate Risk Curve is closer to the Hypo Risk Curve, resulting in a smaller moderate hypo risk zone. This illustrates the benefit of having more data available for the prediction. For example, for Control Grid point located just above the Moderate Risk Curve in FIG. 54, the additional data results in increased confidence that there is no hypo risk—the same point in FIG. 53 would be located in the buffer zone and there would be less confidence that there was no hypo risk.

Figure 55:
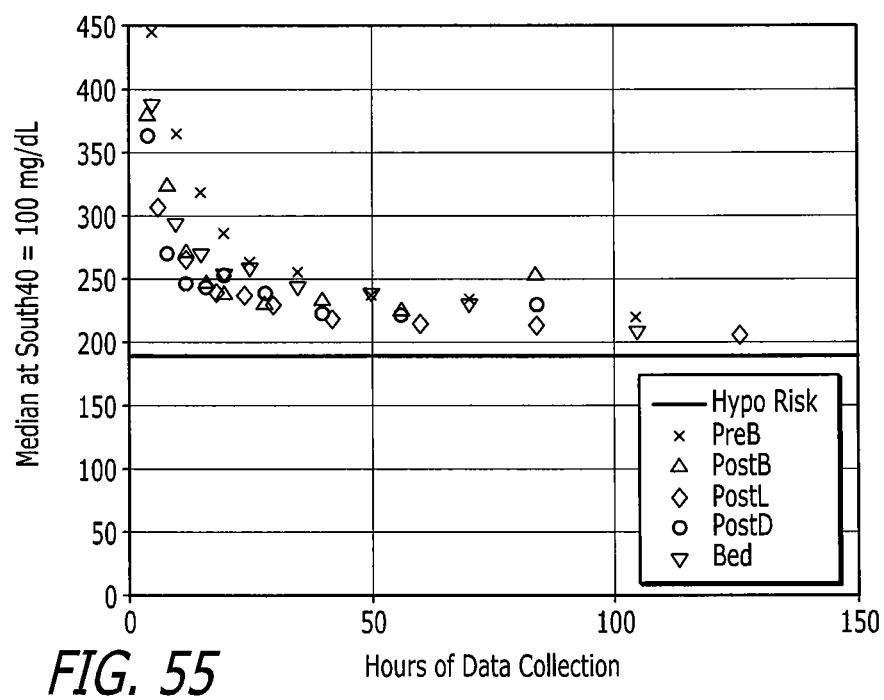
FIG. 55 shows a vertical position of moderate risk curve at S40=100 mg/dL, versus hours of data collection with the LGA setting at medium.

The above calculation is repeated for all combinations of conditions. FIG. 55 illustrates how the Moderate Risk Curve varies across the amount of data available for the prediction and for different TOD periods. Specifically, each Moderate Risk Curve is represented by its ordinate value at the S40 value of 100. This allows one plot to show all Moderate Risk Curves for a given Low Glucose Allowance setting.

FIG. 55 shows the vertical position of the Moderate Risk Curve at S40=100 mg/dL, versus hours of data collection. The LGA setting is Medium. The plot shows again that the Moderate Risk Curve approaches the Hypo Risk Curve as the amount of data collected increases. Note that if there is more than 10 days (40 hours) of data collected for the prediction, further reduction in the moderate hypo risk zone size is small.

The data shown in FIG. 55 are the basis for the Moderate Risk Curves used in the present method. The derivation is as follows:

Smooth curves are fits to the data shown in FIG. 55. Two curves are fit: one for the two overnight TOD periods and one for the three post-meal TOD periods. The smoothed curves are fit by eye and by staying generally above the time zone values. This is a conservative choice; it makes the moderate hypo risk zone a little larger. These fitted curves are shown in FIG. 56.

Every Moderate Risk Curve can be uniquely defined by its value at S40=100. Table H1 shows this value for the smoothed curves in (a) for each possible condition. Each Moderate Risk Curve is based on assumption of a Gamma distribution, constrained by the Curve passing through the value in the table.

Figure 56:
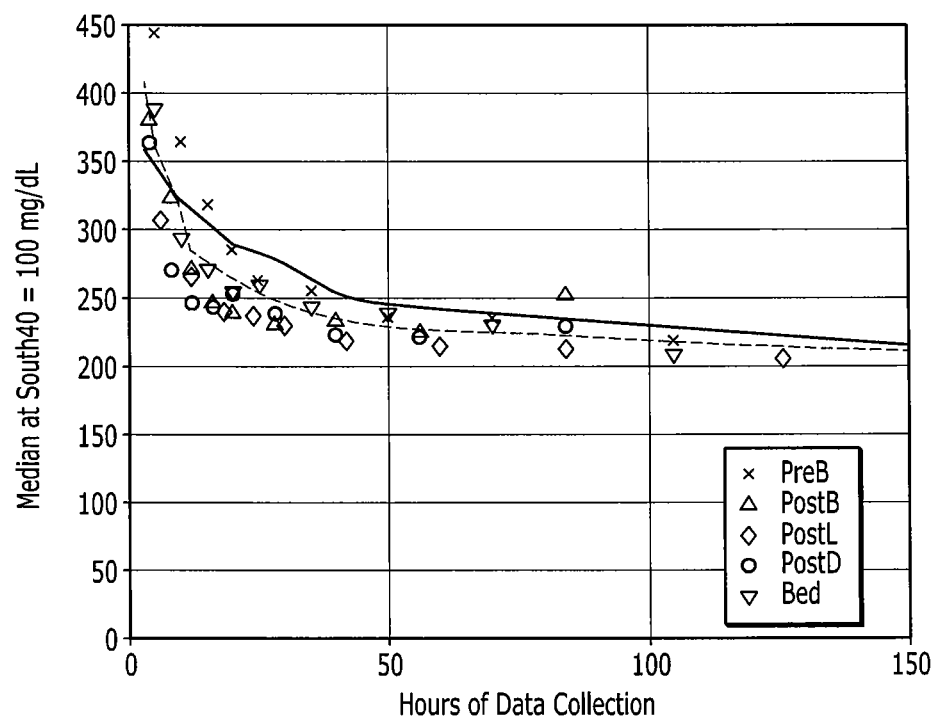
FIG. 56 is the same as FIG. 55 with smooth curves added for overnight (solid) and post-meal (dashed) TOD periods.

FIG. 56 is the Same FIG. 55 with Smooth Curves Added for Overnight (Solid) and Post-Meal (Dashed) TOD Periods.

TABLE H1

Moderate Risk Curve values at
South40 = 100 mg/dL, in units of mg/dL.

| Hrs of Data Collected | Low Hypo Allowance | | Medium Hypo Allowance | | High Hypo Allowance | |
| --- | --- | --- | --- | --- | --- | --- |
| | Fasting | Post-meal | Fasting | Post-meal | Fasting | Post-meal |
| 3 | 400 | 430 | 360 | 410 | 340 | 390 |
| 5 | 380 | 390 | 350 | 360 | 320 | 335 |
| 8 | 355 | 365 | 330 | 335 | 300 | 300 |
| 12 | 345 | 310 | 315 | 285 | 290 | 270 |
| 20 | 320 | 290 | 290 | 265 | 270 | 235 |
| 30 | 305 | 265 | 275 | 245 | 250 | 220 |
| 40 | 290 | 255 | 255 | 235 | 230 | 215 |
| 50 | 275 | 250 | 245 | 230 | 220 | 210 |
| 100 | 250 | 245 | 230 | 220 | 205 | 200 |
| 150 | 240 | 230 | 215 | 210 | 195 | 190 |

Using the remaining ⅓ of the JDRF data, the calculated Moderate Risk Curves were checked to determine if the design goal was met; with a confidence level of 95%, less than 10% of the predictions indicate "no hypo risk." For 18 subjects, the hypo risk prediction performance was checked across default TOD periods, all LGA setting values, and a range of prediction period duration values from 3 hours to 150 hours. The result was 95.4% correct hypo risk predictions, which exceeds the 95% confidence level. The second check was rerun with 8 different TOD schedules with 8 different TOD durations, resulting in 95.7% correct hypo risk prediction.

To simplify the software implementation, the Moderate Risk Curves are defined as hyperbolic functions with specific parameters that define each curve. For every Moderate Risk Curve defined in Table H1, a hyperbolic function is fit. The hyperbolic function has the advantage that it is defined by 5 parameters that can be stored in software rather than storing each entire curve (at 1 value per 2 mg/dL S40 increment, this would be hundreds of values per curve, instead of 5).

Figure 57:
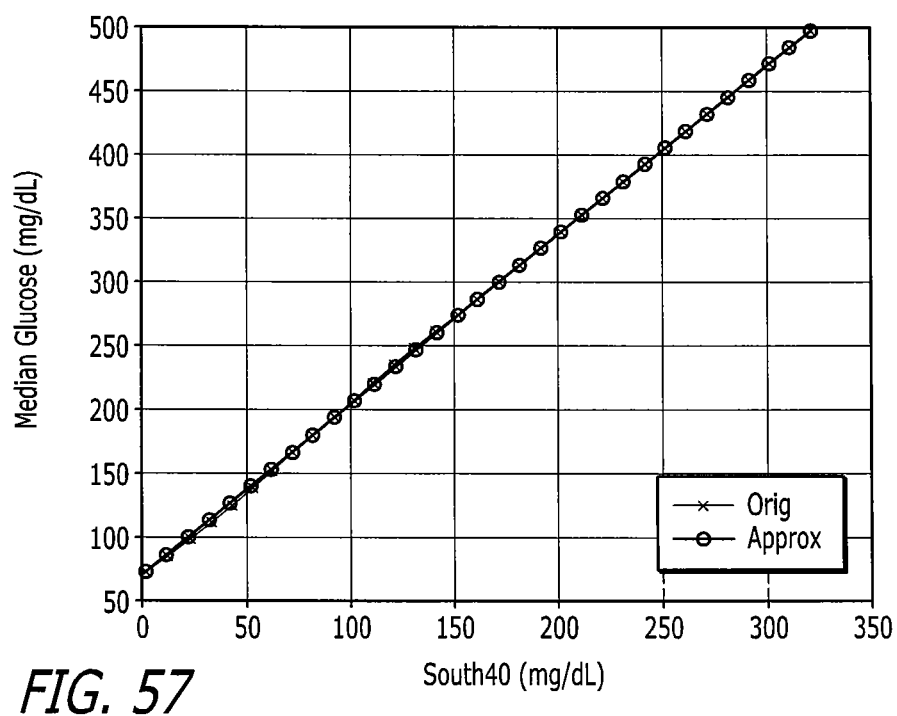
FIG. 57 is an original moderate risk curve (lighter weight) and approximate hyperbolic function (heavier weight) lines—worst case.
Figure 58:
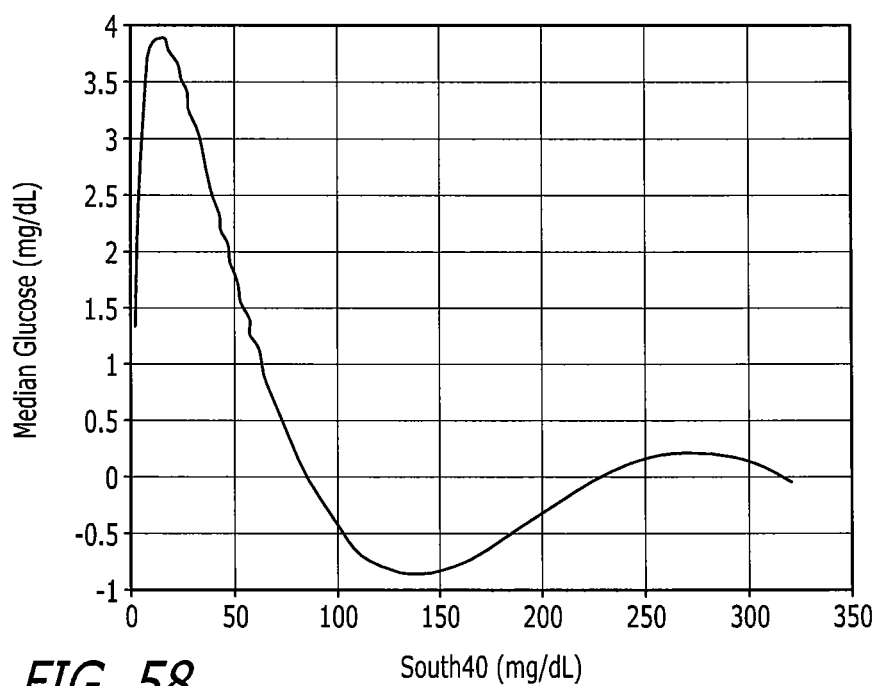
FIG. 58 shows the residual of the original moderate risk curve vs. approximate hyperbolic function—worst case.

The worst of all of these hyperbolic approximations is shown in FIG. 57, where this worst fit is shown to be good with an IV of 0.997. FIG. 58 shows the residual of this worst fit. For S40 values greater than 70 mg/dL, the fit is within +/−1 mg/dL. For S40 values below 70 mg/dL, the Hyperbolic function can be up to 4 mg/dL more than the determined Moderate Risk Curve; however, this approximation will cause the moderate risk zone to be slightly larger and is therefore conservative from a hypo risk perspective.

FIG. 57 shows the original Moderate Risk Curve (thin line) and approximate hyperbolic function (heavy line) lines—worst case. FIG. 58 shows the residual of the original Moderate Risk Curve vs. approximate hyperbolic function—worst case In the present description, the terms component, module, device, may refer to any type of logical or functional process or blocks that may be implemented in a variety of ways. For example, the functions of various blocks can be combined with one another into any other number of modules. Modules can be implemented as a software program stored on a tangible memory (e.g., random access memory, read only memory, CD-ROM memory, hard disk drive, or others) to be read by a processor, or central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. The modules can be implemented using special purpose instructions (SIMD instructions or others), field programmable logic arrays, or any mix thereof or others which provides the desired level performance and cost.

As disclosed herein, implementations and features of the invention may be implemented through computer-hardware, software, and/or firmware. For example, the systems and methods disclosed herein may be embodied in various forms including, for example, a data processor, such as a computer that also includes a data base, digital electronic circuitry, firmware, software, or in combinations of them. Further, while some of the disclosed implementations describe components such as software, systems and methods consistent with the innovations herein may be implemented with any combination of hardware, software, and/or firmware. Moreover, the above-noted features and other aspects and principles of the innovations herein may be implemented in various environments. Such environments and related applications may be specially constructed for performing the various processes and operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Further implementations and/or variations may be provided in addition to those set forth herein. For example, the present invention may be directed to various combinations and sub-combinations of the features disclosed in the detailed description of preferred embodiments.

While the system and method have been described in terms of what are presently considered to be specific embodiments, they need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A system for monitoring glucose of a patient during pregnancy, the system comprising:
 a continuous glucose monitor configured to be worn by the patient and to collect glucose measurements, the continuous glucose monitor comprising a sensor configured to sense an interstitial glucose level; and a computing device in wireless communication with the continuous glucose monitor to receive the glucose measurements, wherein the computing device comprises:

a processor coupled with non-volatile, non-transitory memory, the non-volatile, non-transitory memory storing a glucose data processing program that, when executed by the processor, causes the processor to:

adjust a predetermined hypoglycemia threshold, wherein the predetermined hypoglycemia threshold comprises a first number of glucose measurements below a predetermined low glucose level, for determining a hypoglycemia risk level to provide an adjusted hypoglycemia threshold based on patient-specific criteria, wherein the patient-specific criteria comprises a pregnant condition of the patient, wherein the adjusted hypoglycemia threshold comprises a second number of glucose measurements below the predetermined low glucose level, wherein the second number of glucose measurements below the predetermined low glucose level is greater than the first number of glucose measurements below the predetermined low glucose level; and determine the hypoglycemia risk level based on a comparison of the glucose measurements collected by the continuous glucose monitor to the adjusted hypoglycemia threshold, and a display configured to display a visualization of the hypoglycemia risk level.

2. The system of claim 1, wherein the glucose data processing program, when executed by the processor, further causes the processor to determine a treatment recommendation based on the glucose measurements.

3. The system of claim 1, wherein the predetermined low glucose level is 70 mg/dL.

4. The system of claim 1, wherein the visualization comprises the hypoglycemia risk level for each of a plurality of time periods.

5. The system of claim 1, wherein the display is a touch screen display configured to receive input from the patient.

6. The system of claim 1, wherein the computing device comprises a mobile telephone.

7. The system of claim 1, wherein the visualization of the hypoglycemia risk level comprises an indication of high, moderate, or low risk.

8. A method for monitoring glucose of a patient during pregnancy, the method comprising:

collecting glucose measurements from the patient by a sensor of a continuous glucose monitor, wherein the glucose measurements are indicative of an interstitial glucose level;

communicating wirelessly the glucose measurements to a computing device;

executing a glucose data processing program by a processor of the computing device;

adjusting a predetermined hypoglycemia threshold, wherein the predetermined hypoglycemia threshold comprises a first number of glucose measurements below a predetermined low glucose level, for determining a hypoglycemia risk level in the glucose data processing program to provide an adjusted hypoglycemia threshold based on patient-specific criteria, wherein the patient-specific criteria comprises a pregnant condition of the patient, wherein the adjusted hypoglycemia threshold comprises a second number of glucose measurements below the predetermined low glucose level, wherein the second number of glucose measurements below the predetermined low glucose level is greater than the first number of glucose measurements below the predetermined low glucose level;

determining, by the glucose data processing program, the hypoglycemia risk level based on a comparison of the glucose measurements collected by the continuous glucose monitor to the adjusted hypoglycemia threshold; and displaying a visualization of the hypoglycemia risk level on a display of the computing device.

9. The method of claim 8, wherein the predetermined low glucose level is 70 mg/dL.

10. The method of claim 8, further comprising displaying a treatment recommendation based on the glucose measurements collected by the continuous glucose monitor.

11. The method of claim 8, further comprising displaying a plot of the glucose measurements collected by the continuous glucose monitor.

12. The method of claim 8, further comprising displaying the hypoglycemia risk level for each of a plurality of time periods.

13. The method of claim 8, wherein the computing device comprise a mobile telephone.

14. The method of claim 8, further comprising:

determining a trend in the glucose measurements collected by the continuous glucose monitor, and displaying the trend.

15. The method of claim 8, further comprising transmitting the glucose measurements collected by the continuous glucose monitor to a cloud computing system via the computing device.

16. The method of claim 8, wherein the visualization of the hypoglycemia risk level comprises an indication of high, moderate, or low risk.

17. A system for monitoring glucose of a patient during pregnancy, the system comprising:

a continuous glucose monitor configured to be worn by the patient and to collect glucose measurements, the continuous glucose monitor comprising a sensor configured to sense an interstitial glucose level; and a computing device in wireless communication with the continuous glucose monitor to receive the glucose measurements, wherein the computing device comprises:

a processor coupled with non-volatile, non-transitory memory, the non-volatile, non-transitory memory storing a glucose data processing program that, when executed by the processor, causes the processor to:

determine a hypoglycemia risk level based on the glucose measurements collected by the continuous glucose monitor, wherein the hypoglycemia risk level is determined based on a comparison of the glucose measurements to an adjustable hypoglycemia threshold, wherein the adjustable hypoglycemia threshold is changed from a first hypoglycemia threshold comprising a first number of glucose measurements below a predetermined low glucose level, to a second hypoglycemia threshold comprising a second number of glucose measurements below the predetermined low glucose level based on patient-specific criteria, wherein the second number is greater than the first number, and wherein the patient-specific criteria comprises a pregnant condition of the patient, a display configured to display a visualization of the hypoglycemia risk level determined from the comparison of the glucose measurements to the second hypoglycemia threshold.

18. The system of claim 17, wherein the hypoglycemia risk level comprises one of high, moderate, or low risk.

* * * * *